US008354407B2

(12) United States Patent
Djung et al.

(10) Patent No.: US 8,354,407 B2
(45) Date of Patent: Jan. 15, 2013

(54) 2-ANILINO-4-(HETEROCYCLIC)AMINO-PYRIMIDINES

(75) Inventors: Jane Far-Jine Djung, Furlong, PA (US); Adam Golebiowski, Madison, CT (US); Jack A. Hunter, Loveland, OH (US); Gary P. Schrum, Maineville, OH (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 537 days.

(21) Appl. No.: 12/465,704

(22) Filed: May 14, 2009

(65) Prior Publication Data

US 2009/0227586 A1 Sep. 10, 2009

Related U.S. Application Data

(63) Continuation of application No. 11/762,394, filed on Jun. 13, 2007, now abandoned.

(60) Provisional application No. 60/813,956, filed on Jun. 15, 2006.

(51) Int. Cl.
| | |
|---|---|
| *C07D 239/48* | (2006.01) |
| *C07D 413/06* | (2006.01) |
| *C07D 413/14* | (2006.01) |
| *A61K 31/505* | (2006.01) |
| *A61K 31/5355* | (2006.01) |
| *A61P 9/04* | (2006.01) |

(52) U.S. Cl. .......... 514/235.8; 514/275; 544/122; 544/323

(58) Field of Classification Search ............ 514/235.8, 514/275; 544/122, 323
See application file for complete search history.

(56) References Cited

U.S. PATENT DOCUMENTS

| | | | |
|---|---|---|---|
| 2,437,683 A | 3/1948 | Curd et al. | |
| 2,443,305 A | 6/1948 | Curd et al. | |
| 5,958,935 A | 9/1999 | Davis et al. | |
| 6,518,286 B1 | 2/2003 | Baxter et al. | |
| 6,846,827 B1* | 1/2005 | Cumming | 514/256 |
| 6,943,172 B2 | 9/2005 | Nagarathnam et al. | |
| 7,122,542 B2 | 10/2006 | Singh et al. | |
| 7,514,445 B2* | 4/2009 | Freyne et al. | 514/272 |
| 2004/0186118 A1 | 9/2004 | Bryant et al. | |
| 2005/0090493 A1 | 4/2005 | Breault et al. | |
| 2005/0209231 A1 | 9/2005 | Wu et al. | |
| 2007/0293525 A1 | 12/2007 | Djung et al. | |
| 2008/0194605 A1 | 8/2008 | Heinrich et al. | |
| 2011/0071158 A1* | 3/2011 | Sapountzis et al. | 514/252.14 |
| 2011/0105472 A1* | 5/2011 | Greul et al. | 514/212.07 |
| 2011/0130401 A1* | 6/2011 | Sapountzis et al. | 514/235.8 |
| 2011/0144107 A1* | 6/2011 | Chatterjee et al. | 514/235.5 |
| 2011/0201602 A1* | 8/2011 | Geuns-Meyer et al. | 514/227.8 |
| 2011/0207734 A1* | 8/2011 | Palani et al. | 514/235.8 |
| 2011/0212077 A1* | 9/2011 | Noronha et al. | 424/130.1 |

FOREIGN PATENT DOCUMENTS

| | | |
|---|---|---|
| DE | 825 263 | 7/1949 |
| DE | 833 651 | 7/1949 |
| DE | 23 42 881 | 1/1975 |
| EP | 0945 442 A1 | 9/1999 |
| EP | 0945 443 A1 | 9/1999 |
| EP | 1 571 146 A1 | 7/2005 |
| FR | 2 244 520 | 4/1975 |
| GB | 592928 | 6/1943 |
| GB | 587550 | 9/1944 |
| GB | 1092571 | 5/1965 |
| WO | 97/19065 A1 | 5/1997 |
| WO | 99/50250 A1 | 10/1999 |
| WO | 00/58305 A1 | 10/2000 |
| WO | 02/04429 A1 | 1/2002 |
| WO | 03/018021 A1 | 3/2003 |
| WO | 03/018022 A1 | 3/2003 |
| WO | 03/026664 A1 | 4/2003 |
| WO | 03/026665 A1 | 4/2003 |
| WO | 03/026666 A1 | 4/2003 |
| WO | 03/032994 A2 | 4/2003 |
| WO | 03/032997 A1 | 4/2003 |
| WO | 03/037891 A1 | 5/2003 |
| WO | 2003/040141 A1 | 5/2003 |
| WO | 03/094920 A1 | 11/2003 |
| WO | 2004/048343 A1 | 6/2004 |
| WO | WO 2004/089286 | * 10/2004 |
| WO | 2005/003103 A2 | 1/2005 |
| WO | 2005/013996 A2 | 2/2005 |
| WO | 2005/016893 A2 | 2/2005 |
| WO | 2005/068437 A1 | 7/2005 |
| WO | 2006/074057 A2 | 7/2006 |
| WO | 2006/108487 A1 | 10/2006 |

(Continued)

OTHER PUBLICATIONS

Cumming, et al., (I) Bioorganic & Medicinal Chemistry Letters (2004), 14(21), 5389-5394.*
Adrian, et al., Nature Chemical Biology (Feb. 2006), 2(2), 95-102.*
Curd, Francis, H.S., and Rose, F.L.; Synthetic Antimalarials. Part I; Some Derivatives of Arylamino and Aryl Substituted Pyrimidines; Journal of the Chemical Society, pp. 343-351[1946].
Curd, Francis, H.S., et al; Synthetic Antimalarials, Part II; 2-Substituted-anilino-4-amino-alkylamino-6-methylpyrimidines; Journal of the Chemical Society, pp. 351-357 [1946].
Arvanitis, Elena A., et al; Solid Phase Synthesis of 2,4-Diaminopyrimidines via Lewis Acid-Mediated Aromatic Nucleophilic Substitution; Journal of Combinatorial Chemistry, 2004, 6, pp. 414-419.

(Continued)

*Primary Examiner* — James O Wilson
*Assistant Examiner* — Cecilia M Jaisle
(74) *Attorney, Agent, or Firm* — Michael P. Morris; Usha R. Patel; David A. Dow

(57) ABSTRACT

The present invention relates to 2-arylamino-4-(heterocyclic) aminopyrimidines inhibitors which are inhibitors and therefore inhibit Protein Kinase C-alpha (PKC-α). The PKC-α inhibitors of the present invention are important for improving myocardial intracellular calcium cycling, resulting in improved myocardial contraction and relaxation performance and thereby slowing the progression of heart failure. The present invention further relates to compositions comprising said 2-arylamino-4-(heterocyclic)amino-pyrimidines and to methods for controlling, abating, or otherwise slowing the progression of heart failure.

11 Claims, No Drawings

FOREIGN PATENT DOCUMENTS

| | | | |
|---|---|---|---|
| WO | WO 2006/124874 | * | 11/2006 |
| WO | 2006/133426 | A2 | 12/2006 |
| WO | 2007/009524 | A1 | 1/2007 |
| WO | 2007144769 | A2 | 12/2007 |
| WO | 2007146977 | A1 | 12/2007 |
| WO | 2007147125 | A2 | 12/2007 |
| WO | 2007147133 | A1 | 12/2007 |
| WO | 2010106097 | A1 | 9/2010 |
| WO | 2010136559 | A1 | 12/2010 |

OTHER PUBLICATIONS

Sanghavi, D., et al; Synthesis and study of 2-arylamino-4-(substituted amino)-6-methylpyrimidines as possible antimalarial agents: Document No. 96:122747; Bulletin of Haffkine Institute (1980) 8 (3), 95-101.

Coats, E., et al; Correlation Analysis of pyrimidine folic acid antagonists as antibacterial agents Document No. 92:34951 European Journal of Medicinal Chemistry (1979), 14, 3, 261-70.

Edward C. Dempsey, et al., "Protein Kinase C Isozymes and the Regulation of Diverse Cell Responses", American Journal of Physiology Lung Cell Molecular Physiology, vol. 279, p. 429, 2000.

Daria Mochly-Rosen, et al., "Localization of Protein Kinases by Anchoring Proteins: A Theme in Signal Transduction", Science, vol. 268, p. 247, 1995.

Jeffery D. Molkentin, et al., "Cytoplasmic Signaling Pathways That Regulate Cardiac Hypertrophy", Annual Review of Physiology, vol. 63, p. 391, 2001.

* cited by examiner

2-ANILINO-4-(HETEROCYCLIC)AMINO-PYRIMIDINES

RELATED APPLICATIONS

This application is a continuation of U.S. application Ser. No. 11/762,394 filed Jun. 13, 2007, which claims benefit of U.S. provisional application No. 60/813,956, filed Jun. 15, 2006, the entirety of which is incorporated herewith by reference.

FIELD OF THE INVENTION

The present invention relates to 2-arylamino-4-(heterocyclic)aminopyrimidines which are inhibitors of Protein Kinase C-alpha (PKC-α). The PKC-α inhibitors of the present invention are important for improving myocardial intracellular calcium cycling, resulting in improved myocardial contraction and relaxation performance and thereby slowing the progression of heart failure. The present invention further relates to compositions comprising said 2-arylamino-4-(heterocyclic)amino-pyrimidines and to methods for controlling, abating, or otherwise slowing the progression of heart failure.

BACKGROUND OF THE INVENTION

Many biologically active substances, for example, hormones, neurotransmitters and peptides are known to exert functions via intracellular mediators such as, cyclic adenosine monophosphate (cAMP), cyclic guanosine monophosphate (cGMP), diacylglycerol (DAG) and calcium. In many cases, these mediators activate or inactivate intracellular kinases or phosphatases that are important in protein phosphorylation/dephosphorylation, and thus play important roles in regulating cellular processes and functions. The protein kinase C (PKC) family of calcium and/or lipid-activated serine-threonine kinases function downstream of nearly all membrane-associated signal transduction pathways.[1] Approximately 12 different isozymes comprise the PKC family, which are broadly classified by their activation characteristics. The conventional PKC isozymes (PKCα, βI, βII, and γ) are calcium- and lipid-activated, while the novel isozymes (ε, θ, η, and δ) and atypical isozymes (ζ, ι, υ, and μ) are calcium independent but activated by distinct lipids.[2] For example, stimulation of Gαq-coupled G-protein coupled receptors (GPCR) can activate phospholipase C (PLC) which in turn mediates hydrolysis of inositol phospholipids resulting in the generation of inositol 1,4,5-triphosphate ($IP_3$) and DAG. $IP_3$ and DAG can activate the different isoforms of PKC by mobilizing calcium (calcium sensitive enzymes) or by directly activating PKC, respectively. Once activated, PKC isozymes translocate to discrete subcellular locations through direct interactions with docking proteins termed RACKs (Receptor for Activated C Kinases), which permit specific substrate recognition and subsequent signal transduction.[3]

Alterations in PKC activity has been suggested to contribute to human diseases, inter alia, diabetes, numerous forms of cancer, microalbinuria, endothelial dysfunction, cerebrovascular disease, stroke, coronary heart disease, cardiovascular disease and sequela (e.g. arrhythmia, sudden death, increased infarct size, congestive heart failure, angina), myocardial ischemic states, hypertension, lipid disorders, ischemia-reperfusion injury, atherosclerosis, peripheral artery/vascular disease, microvascular complications of diabetes (neuropathy, nephropathy, retinopathy), restenosis, renal disease, blood coagulation disorders, inflammatory diseases and heart failure and inhibition of PKC in these settings could be used to treat or prevent human disease. Lending support to the modulation of PKC in cardiac disease, PKC activation has been associated with cardiac hypertrophy, dilated cardiomyopathy, ischemic injury and mitogen stimulation.

Heart disease is the leading cause of death in industrialized nations. Historically heart failure (HF) has been a product of hypertension, coronary heart disease, genetic disorders, valvular deformities, diabetes or cardiomyopathy. While the root cause of heart failure is multifaceted, it uniformly is marked by impaired diastolic and/or systolic function and can be accompanied by chamber enlargement which ultimately manifest in symptomatic heart failure (fatigue, pulmonary edema, circulatory congestion, etc.)

The risk of death due to heart failure is 5-10% annually in patients with mild symptoms of heart failure, and increases to 30-40% annually in patients with advanced heart failure, with a 50% overall mortality rate at 5 years. The current mainstays of heart failure therapy are drugs that act on the renin-angiotensin-aldosterone system (ACEI, ARB, aldosterone inhibitor), diuretics, digoxin and β-adrenergic receptor blockers. Despite the fact that multiple drug classes are used to treat heart failure patients, new cases of heart failure are growing at over 10% per year.

Patients with acute decompensated heart failure (ADHF) are a treatment challenge to physicians and can present with volume overload and/or diminished cardiac output. Initial treatments for ADHF patients include intravenous diuretics, vasodilators, natriuretic peptides and inotropic agents. Despite the widespread use of these agents, long-term safety and benefit of these drugs have been questioned. In the case of inotropes, drugs that increase cardiac output and cardiac contractility without increasing myocardial oxygen consumption or heart rate are desirous. Despite the available treatments for patients with ADHF, hospital readmission rates are approximately 50% within 6 months and mortality is approximately 20-40% at 1 year.

The primary function of the heart is to generate and sustain an arterial blood pressure necessary to provide adequate perfusion of organs. It has, therefore, become an area of intense investigation to decipher the mechanism(s) which initiate and contribute to the development of heart failure rather than relying on a means for treating the symptoms of heart failure alone. At the cardiomyocyte (cardiac contractile cells) level, impaired calcium cycling is a hallmark of heart failure as is the basis of contractile abnormalities. Calcium plays a key role in regulating kinases, phosphatases and transcription factors believed to influence the remodeling process indicating that both acute and sustained alterations in intracellular calcium levels may have profound effect on cardiac function and remodeling (i.e., changes in wall thickness or chamber volume). This theory would support the proposition that the development of new therapies addressing the slowing and preventing of the disease progression, would be perhaps more effective against heart failure than palliation of heart failure.

Therefore, there is a limited means to treat patients with various forms and stages of heart failure and there is incentive to develop novel, safe and effective treatments to prevent or treat patients with symptoms of heart failure, acute exacerbation of heart failure and chronic heart failure and other cardiovascular diseases. An agent that has benefits in the treating acute exacerbations of heart failure as well as treating chronic heart failure is desirous.

1. Molkentin et al. (2001) *Annu. Rev. Physiol.* 63:391-426.
2. Dempsey et al. (2000) *Am. J. Physiol. Lung Mol. Physiol.* 279:247-251.
3. Mochly-Rosen, D. (1995) *Science* 268:247-251.

SUMMARY OF THE INVENTION

The present invention meets the aforementioned needs in that it has been found that certain 2-arylamino-4-(heterocyclic)aminopyrimidines are effective for inhibiting Protein Kinase C-alpha (PKC-α) thereby improving myocardial contraction and relaxation performance and slowing the progression of heart failure.

The present invention encompasses four major aspects each of which have their own separate categories, aspects, iterations, and specific iterative examples. The major aspects of the present invention include:

i) novel compositions of matter which are effective in inhibiting PKC-α;

ii) compositions or pharmaceutical compositions (matrices) comprising said compositions of matter;

iii) methods for treating, preventing, controlling, abating, or alleviating one or more of the causes of progressive heart failure which is affected by administration of a PKC-α antagonist, whether administered alone or in a composition or within a pharmaceutical composition (matrix); and iv) a process for preparing the PKC-α inhibitors of the present invention.

The first aspect of the present invention as a whole, relates to compounds, which include all enantiomeric and diastereomeric forms and pharmaceutically acceptable salts thereof, said compounds having the formula:

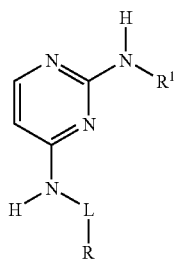

wherein R is a substituted or unsubstituted heterocyclic unit containing from 3 to 7 atoms;

L is a linking group having the formula:

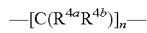

—[C($R^{4a}R^{4b}$)]$_n$— each $R^{4a}$ and $R^{4b}$ is independently chosen from:
i) hydrogen; or
ii) $C_1$-$C_4$ linear, branched, or cyclic alkyl;
the index n is from 0 to 4; and
$R^1$ is substituted or unsubstituted phenyl having the formula:

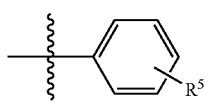

$R^5$ is hydrogen or one or more independently chosen substitutes for hydrogen.

The second major aspect of the present invention relates to compositions comprising:

a) an effective amount of one or more compounds according to the present invention; and b) one or more acceptable excipients.

The third major aspect of the present invention relates to methods of use. As described herein below, the PKC-α inhibitors of the present invention are important for improving myocardial contraction and relaxation performance and thereby slowing the progression of heart failure and their administration to humans is, therefore, an effective treatment for humans suffering from acute heart failure.

The fourth major aspect of the present invention relates to a process for preparing the PKC-α inhibitors of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The present invention addresses several unmet medical needs, inter alia:

1) improving cardiac contraction/relaxation parameters in heart failure patients, leading to reduction of symptoms; and 2) attenuating adverse cardiac remodeling in heart failure patients, ultimately providing prolonged patient survival.

These and other unmet medical needs are resolved by the PKC-α inhibitors of the present invention, which are capable of blocking Protein Kinase C-alpha from impairing sarcoplasmic reticulum $Ca^{2+}$ uptake. By providing heart failure patients with a PKC-α inhibitor, it is believed the patients will derive an improvement in cardiac function, thus resulting in improved myocardial contraction and relaxation performance and could result in slowing the progression to heart failure.

The following chemical hierarchy is used throughout the specification to describe and enable the scope of the present invention and to particularly point out and distinctly claim the units which comprise the compounds of the present invention. The term "hydrocarbyl" stands for any carbon atom-based unit (organic molecule), said units optionally containing one or more organic functional group, including inorganic atoms comprising salts, inter alia, carboxylate salts, quaternary ammonium salts. Within the broad meaning of the term "hydrocarbyl" are the classes "acyclic hydrocarbyl" and "cyclic hydrocarbyl" which terms are used to divide hydrocarbyl units into cyclic and non-cyclic classes.

As it relates to the following definitions, "cyclic hydrocarbyl" units may comprise only carbon atoms in the ring (hydrocarbyl and aryl rings) or may comprise one or more heteroatoms in the ring (heterocyclic and heteroaryl). For "hydrocarbyl" rings the lowest number of carbon atoms in a ring are 3 carbon atoms; cyclopropyl. For "aryl" rings the lowest number of carbon atoms in a ring are 6 carbon atoms;

phenyl. For "heterocyclic" rings the lowest number of carbon atoms in a ring is 1 carbon atom; diazirinyl, epoxy. For "heteroaryl" rings the lowest number of carbon atoms in a ring is 1 carbon atom; 1,2,3,4-tetrazolyl.

A. Substituted and Unsubstituted $C_1$-$C_{20}$ Acyclic Hydrocarbyl:

For the purposes of the present invention the term "substituted and unsubstituted $C_1$-$C_{20}$ acyclic hydrocarbyl" encompasses 3 categories of units:

1) $C_1$-$C_{20}$ linear or branched alkyl, non-limiting examples of which include, methyl ($C_1$), ethyl ($C_2$), n-propyl ($C_3$), iso-propyl ($C_3$), n-butyl ($C_4$), sec-butyl ($C_4$), iso-butyl ($C_4$), tert-butyl ($C_4$), and the like; substituted $C_1$-$C_{20}$ linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), 3-carboxypropyl ($C_3$), and the like.

2) $C_2$-$C_{20}$ linear or branched alkenyl, non-limiting examples of which include, ethenyl ($C_2$), 3-propenyl ($C_3$), 1-propenyl (also 2-methylethenyl) ($C_3$), isopropenyl (also 2-methylethen-2-yl) ($C_3$), buten-4-yl ($C_4$), and the like; substituted $C_2$-$C_{20}$ linear or branched alkenyl, non-limiting examples of which include, 2-chloroethenyl (also 2-chlorovinyl) ($C_2$), 4-hydroxybuten-1-yl ($C_4$), 7-hydroxy-7-methyloct-4-en-2-yl ($C_9$), 7-hydroxy-7-methyloct-3,5-dien-2-yl ($C_9$), and the like.

3) $C_2$-$C_{20}$ linear or branched alkynyl, non-limiting examples of which include, ethynyl ($C_2$), prop-2-ynyl (also propargyl) ($C_3$), propyn-1-yl ($C_3$), and 2-methyl-hex-4-yn-1-yl ($C_7$); substituted $C_2$-$C_{20}$ linear or branched alkynyl, non-limiting examples of which include, 5-hydroxy-5-methylhex-3-ynyl ($C_7$), 6-hydroxy-6-methylhept-3-yn-2-yl ($C_8$), 5-hydroxy-5-ethylhept-3-ynyl ($C_9$), and the like.

B. Substituted and Unsubstituted $C_1$-$C_{20}$ Cyclic Hydrocarbyl:

For the purposes of the present invention the term "substituted and unsubstituted $C_1$-$C_{20}$ cyclic hydrocarbyl" encompasses 5 categories of units:

1) The term "carbocyclic" is defined herein as "encompassing rings comprising from 3 to 20 carbon atoms, wherein the atoms which comprise said rings are limited to carbon atoms, and further each ring can be independently substituted with one or more moieties capable of replacing one or more hydrogen atoms." The following are non-limiting examples of "substituted and unsubstituted $C_3$-$C_{20}$ carbocyclic rings" which encompass the following categories of units:

i) carbocyclic rings having a single substituted or unsubstituted hydrocarbon ring, non-limiting examples of which include, cyclopropyl ($C_3$), 2-methyl-cyclopropyl ($C_3$), cyclopropenyl ($C_3$), cyclobutyl ($C_4$), 2,3-dihydroxycyclobutyl ($C_4$), cyclobutenyl ($C_4$), cyclopentyl ($C_5$), cyclopentenyl ($C_5$), cyclopentadienyl ($C_5$), cyclohexyl ($C_6$), cyclohexenyl ($C_6$), cycloheptyl ($C_7$), cyclooctanyl ($C_8$), decalinyl ($C_{10}$), 2,5-dimethylcyclopentyl ($C_5$), 3,5-dichlorocyclohexyl ($C_6$), 4-hydroxycyclohexyl ($C_6$), and 3,3,5-trimethylcyclohex-1-yl ($C_6$).

ii) carbocyclic rings having two or more substituted or unsubstituted fused hydrocarbon rings, non-limiting examples of which include, octahydropentalenyl ($C_8$), octahydro-1H-indenyl ($C_9$), 3a,4,5,6,7,7a-hexahydro-3H-inden-4-yl ($C_9$), decahydroazulenyl ($C_{10}$); bicyclo [6.2.0]decanyl ($C_{10}$), decahydronaphthalenyl ($C_{10}$), and dodecahydro-1H-fluorenyl ($C_{13}$).

iii) carbocyclic rings which are substituted or unsubstituted bicyclic hydrocarbon rings, non-limiting examples of which include, bicyclo-[2.1.1]hexanyl, bicyclo[2.2.1] heptanyl, bicyclo[3.1.1]heptanyl, 1,3-dimethyl[2.2.1] heptan-2-yl, bicyclo[2.2.2]octanyl, and bicyclo[3.3.3] undecanyl.

2) The term "aryl" is defined herein as "units encompassing at least one phenyl or naphthyl ring and wherein there are no heteroaryl or heterocyclic rings fused to the phenyl or naphthyl ring and further each ring can be independently substituted with one or more moieties capable of replacing one or more hydrogen atoms." The following are non-limiting examples of "substituted and unsubstituted $C_6$-$C_{14}$ aryl rings" which encompass the following categories of units:

i) $C_6$ or $C_{10}$ substituted or unsubstituted aryl rings; phenyl and naphthyl rings whether substituted or unsubstituted, non-limiting examples of which include, phenyl ($C_6$), naphthylen-1-yl ($C_{10}$), naphthylen-2-yl ($C_{10}$), 4-fluorophenyl ($C_6$), 2-hydroxyphenyl ($C_6$), 3-methylphenyl ($C_6$), 2-amino-4-fluorophenyl ($C_6$), 2-(N,N-diethylamino)phenyl ($C_6$), 2-cyanophenyl ($C_6$), 2,6-di-tert-butylphenyl ($C_6$), 3-methoxyphenyl ($C_6$), 8-hydroxynaphthylen-2-yl ($C_{10}$), 4,5-dimethoxynaphthylen-1-yl ($C_{10}$), and 6-cyano-naphthylen-1-yl ($C_{10}$).

ii) $C_6$ or $C_{10}$ aryl rings fused with 1 or 2 saturated rings non-limiting examples of which include, bicyclo[4.2.0] octa-1,3,5-trienyl ($C_8$), and indanyl ($C_9$).

3) The terms "heterocyclic" and/or "heterocycle" are defined herein as "units comprising one or more $C_1$-$C_{20}$ rings having from 3 to 20 atoms wherein at least one atom in at least one ring is a heteroatom chosen from nitrogen (N), oxygen (O), or sulfur (S), or mixtures of N, O, and S, and wherein further the ring which comprises the heteroatom is also not an aromatic ring." The following are non-limiting examples of "substituted and unsubstituted $C_1$-$C_{20}$ heterocyclic rings" which encompass the following categories of units:

i) heterocyclic units having a single ring containing one or more heteroatoms, non-limiting examples of which include, diazirinyl ($C_1$), aziridinyl ($C_2$), urazolyl ($C_2$), azetidinyl ($C_3$), pyrazolidinyl ($C_3$), imidazolidinyl ($C_3$), oxazolidinyl ($C_3$), isoxazolinyl ($C_3$), isoxazolyl ($C_3$), thiazolidinyl ($C_3$), isothiazolyl ($C_3$), isothiazolinyl ($C_3$), oxathiazolidinonyl ($C_3$), oxazolidinonyl ($C_3$), hydantoinyl ($C_3$), tetrahydrofuranyl ($C_4$), pyrrolidinyl ($C_4$), 1-methylpyrrolidinyl ($C_4$), morpholinyl ($C_4$), 4-methylmorpholinyl ($C_4$), piperazinyl ($C_4$), 1-methylpiperazinyl ($C_4$), 1-acetylpiperazinyl ($C_4$), 1-methanesulfonylpiperazinyl ($C_4$), piperidinyl ($C_5$), 1-methylpiperidinyl ($C_5$), 2,2,6,6-tetramethyl-piperidinyl ($C_5$), dihydropyranyl ($C_5$), tetrahydropyranyl ($C_5$), piperidin-2-onyl (valerolactam) ($C_5$), 2,3,4,5-tetrahydro-1H-azepinyl ($C_6$), 2,3-dihydro-1H-indole ($C_8$), and 1,2,3,4-tetrahydroquinoline ($C_9$).

ii) heterocyclic units having 2 or more rings one of which is a heterocyclic ring, non-limiting examples of which include hexahydro-1H-pyrrolizinyl ($C_7$), 3a,4,5,6,7,7a-hexahydro-1H-benzo[d]imidazolyl ($C_7$), 8-azabicyclo [3.2.1]octyl ($C_7$), 3a,4,5,6,7,7a-hexahydro-1H-indolyl ($C_8$), 1,2,3,4-tetrahydroquinolinyl ($C_9$), and decahydro-1H-cycloocta[b]pyrrolyl ($C_{10}$).

4) The term "heteroaryl" is defined herein as "encompassing one or more $C_1$-$C_{20}$ rings comprising from 5 to 20 atoms wherein at least one atom in at least one ring is a heteroatom chosen from nitrogen (N), oxygen (O), or sulfur (S), or mixtures of N, O, and S, and wherein further at least one of the rings which comprises a heteroatom is an aromatic ring." The following are non-limiting examples of "substituted and unsubstituted $C_1$-$C_{20}$ heterocyclic rings" which encompass the following categories of units:

i) heteroaryl rings containing a single ring, non-limiting examples of which include, 1,2,3,4-tetrazolyl ($C_1$), [1,2,3]triazolyl ($C_2$), [1,2,4]triazolyl ($C_2$), triazinyl ($C_3$), thiazolyl ($C_3$), 1H-imidazolyl ($C_3$), oxazolyl ($C_3$), furanyl ($C_4$), thiopheneyl ($C_4$), pyrimidinyl ($C_4$), 2-phenylpyrimidinyl ($C_4$), pyridinyl ($C_5$), 3-methylpyridinyl ($C_5$), and 4-dimethylaminopyridinyl ($C_5$)

ii) heteroaryl rings containing 2 or more fused rings one of which is a heteroaryl ring, non-limiting examples of which include: 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-]pyrimidinyl ($C_6$), pyrido[2,3-]pyrimidinyl ($C_7$), 2-phenylbenzo[d]thiazolyl ($C_7$), 1H-indolyl ($C_8$), 4,5,6,7-tetrahydro-1-H-indolyl ($C_8$), quinoxalinyl ($C_8$), 5-methylquinoxalinyl ($C_8$), quinazolinyl ($C_8$), quinolinyl ($C_9$), 8-hydroxy-quinolinyl ($C_9$), and isoquinolinyl ($C_9$).

5) $C_1$-$C_6$ tethered cyclic hydrocarbyl units (whether $C_3$-$C_{10}$ carbocyclic units, $C_6$ or $C_{10}$ aryl units, $C_1$-$C_{10}$ heterocyclic units, or $C_1$-$C_{10}$ heteroaryl units) which connected to another moiety, unit, or core of the molecule by way of a $C_1$-$C_6$ alkylene unit. Non-limiting examples of tethered cyclic hydrocarbyl units include benzyl $C_1$-($C_6$) having the formula:

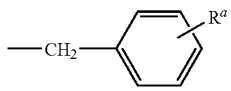

wherein $R^a$ is optionally one or more independently chosen substitutions for hydrogen. Further examples include other aryl units, inter alia, (2-hydroxyphenyl)hexyl $C_6$—($C_6$); naphthalen-2-ylmethyl $C_1$-($C_{10}$), 4-fluorobenzyl $C_1$-($C_6$), 2-(3-hydroxy-phenyl)ethyl $C_2$—($C_6$), as well as substituted and unsubstituted $C_3$-$C_{10}$ alkylenecarbocyclic units, for example, cyclopropylmethyl $C_1$-($C_3$), cyclopentylethyl $C_2$—($C_5$), cyclohexylmethyl $C_1$-($C_6$). Included within this category are substituted and unsubstituted $C_1$-$C_{10}$ alkylene-heteroaryl units, for example a 2-picolyl $C_1$-($C_6$) unit having the formula:

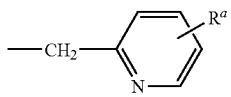

wherein $R^a$ is the same as defined above. In addition, $C_1$-$C_{12}$ tethered cyclic hydrocarbyl units include $C_1$-$C_{10}$ alkyleneheterocyclic units and alkylene-heteroaryl units, non-limiting examples of which include, aziridinylmethyl $C_1$-($C_2$) and oxazol-2-ylmethyl $C_1$-($C_3$).

For the purpose of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

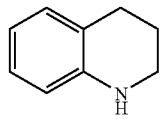

is, for the purposes of the present invention, considered a heterocyclic unit. 6,7-Dihydro-5H-cyclopentapyrimidine having the formula:

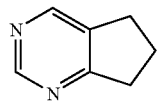

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

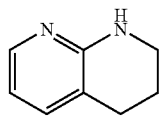

is, for the purposes of the present invention, considered a heteroaryl unit.

The term "substituted" is used throughout the specification. The term "substituted" is defined herein as "a hydrocarbyl moiety, whether acyclic or cyclic, which has one or more hydrogen atoms replaced by a substituent or several substituents as defined herein below." The units, when substituting for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety, or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacements includes cyano, and the like. The term substituted is used throughout the present specification to indicate that a hydrocarbyl moiety, inter alia, aromatic ring, alkyl chain; can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

The following are non-limiting examples of categories and examples herewith of units which can suitably substitute for hydrogen atoms on a cyclic or acyclic hydrocarbyl unit, described herein below as $R^5$ units, wherein in the non-limiting examples provided herein below, $R^{12}$ is hydrogen, $C_1$-$C_{10}$ linear or branched alkyl, $C_2$-$C_{10}$ linear or branched alkenyl, $C_2$-$C_{10}$ linear or branched alkynyl, and $C_6$ or $C_{10}$ aryl.

$R^5$ units according to the present invention may include the following substitutions either comprising $R^5$ itself or when $R^5$ comprises an $R^6$ unit which is bonded to the core phenyl unit by a linking unit:

i) —NHCOR$^{12}$; for example, —NHCOCH$_3$, —NHCOCH$_2$CH$_3$, —NHCOC$_6$H$_5$;

ii) —COR$^{12}$; for example, —COCH$_3$, —COCH$_2$CH$_3$, —COCH$_2$CH$_2$CH$_3$;

iii) —CO$_2$R$^{12}$; for example, —CO$_2$CH$_3$, —CO$_2$CH$_2$CH$_3$, —CO$_2$CH$_2$CH$_2$CH$_3$;

iv) —OCOR$^{12}$; for example, —OCOCH$_3$, —OCOCH$_2$CH$_3$, —OCOCH$_2$CH$_2$CH$_3$;

v) —C(=NH)NH$_2$;

vi) —NHC(=NH)NH$_2$;

vii) —N(R$^{12}$)$_2$; for example, —NH$_2$, —NHCH$_3$, —N(CH$_3$)$_2$, —NH(CH$_2$CH$_3$);

viii) —NHC$_6$H$_5$;

ix) C$_1$-C$_4$ linear, branched, or cyclic alkyl; for example, methyl, ethyl;

x) —CON(R$^{12}$)$_2$; for example, —CONH$_2$, —CONHCH$_3$, —CON(CH$_3$)$_2$;

xi) —CONHNH$_2$;

xii) —NHCN;

xiii) —CN;

xiv) halogen: —F, —Cl, —Br, and —I;

xv) —NHN(R$^{12}$)$_2$; for example, —NHNH$_2$, —NHNHCH$_3$, —NHN(CH$_3$)$_2$;

xvi) —OR$^{12}$; for example, —OH, —OCH$_3$, —OCH$_2$CH$_3$, —OCH$_2$CH$_2$CH$_3$;

xvii) —NO$_2$;

xviii) —CH$_m$X$_{3-m}$; wherein X is halogen, m is from 0 to 2; for example, —CH$_2$F, —CHF$_2$, —CF$_3$, —CCl$_3$, or —CBr$_3$; and xix) —SO$_2$N(R$^{12}$)$_2$; for example, —SO$_2$NH$_2$, —SO$_2$NHCH$_3$; —SO$_2$NHC$_6$H$_5$.

For the purposes of the present invention the terms "compound" and "analog" stand equally well for the novel compositions of matter described herein, including all enantiomeric forms, diastereomeric forms, salts, and the like, and the terms "compound" and "analog" are used interchangeably throughout the present specification.

The compounds of the present invention are 2-arylamino-4-(heterocyclicalkylene)-aminopyrimidines having the core scaffold:

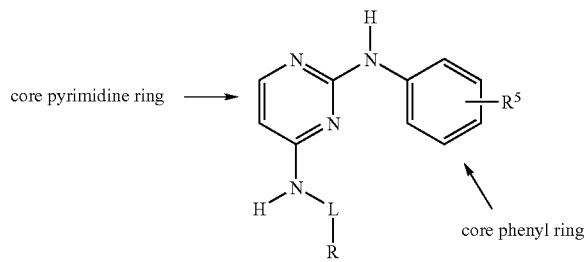

which includes a core pyrimidine ring and a core phenyl ring wherein R$^5$ represents one or more (from 1 to 5) optionally present, and independently selected, substitutes for hydrogen as outlined herein above and described in the categories, aspects, iterations, examples, and tables herein below. As it relates to particularly pointing out the subject matter of the present invention, the unit R$^1$ which contains the core phenyl ring, may be depicted throughout the specification and claims equally well by the following general formulae:

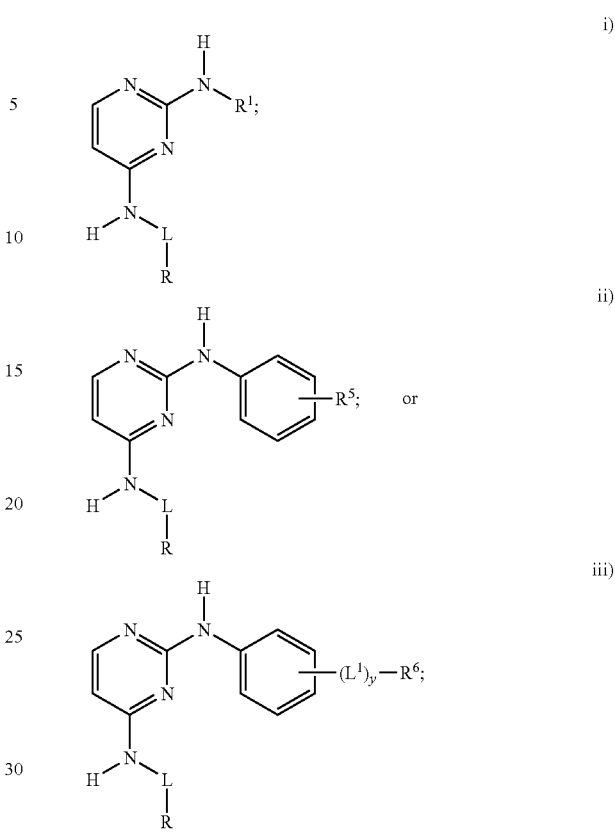

wherein R, R$^1$, R$^5$, R$^6$, L, L$^1$ and y are further described herein below.

R units are substituted or unsubstituted heterocyclic units containing from 3 to 7 atoms.

The first category of R units relates to heterocyclic units wherein the linking group L is bonded to a nitrogen atom, said units having the formula:

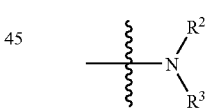

wherein R$^2$ and R$^3$ are taken together to form a heterocycle having from 3 to 7 atoms optionally substituted with one or more substituents.

The first aspect of category one of R units relates to C$_3$, C$_4$ and C$_5$ unsubstituted heterocycles. Non-limiting examples of this aspect includes units chosen from pyrrolidin-1-yl, pyrrolin-1-yl, imidazolidin-1-yl, imidazolin-1-yl, pyrazolidin-1-yl, pyrazolin-1-yl, piperidin-1-yl, piperazin-1-yl, and morpholin-4-yl.

The second aspect of category one of R units relates to C$_3$, C$_4$ and C$_5$ substituted heterocycles. Non-limiting examples of this aspect includes units chosen from 5,5-di-methyl-imidazolin-1-yl, 4-methylpiperazin-1-yl, 4-acetylpiperazin-1-yl, and 4-methane-sulfonyl-piperazin-1-yl.

The second category of R units relates to heterocyclic units wherein the linking group L is bonded to a carbon atom, the first aspect of said units having the formula:

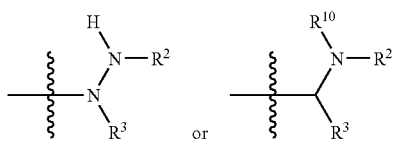

wherein $R^2$ and $R^3$ are taken together to form a heterocycle having from 3 to 7 atoms optionally substituted with one or more substituents; $R^{10}$ is methyl, ethyl, 1-propyl, 2-propyl, or phenyl.

One iteration of the first aspect of category two of R units relates to $C_3$, $C_4$ and $C_5$ substituted or unsubstituted heterocycles non-limiting examples of which include units chosen from pyrrolidin-2-yl, N-methyl-pyrrolidin-2-yl, N-methyl-pyrrolidin-2-one-5-yl, pyrrolin-2-yl, imidazolidin-2-yl, imidazolin-2-yl, pyrazolidin-2-yl, pyrazolin-2-yl, piperidin-2-yl, N-methylpiperidin-2-yl, morpholin-3-yl, and N-methylmorpholin-3-yl.

A further iteration of the first aspect of category two of R units relates to $C_3$, $C_4$ and $C_5$ substituted or unsubstituted heterocycles having a chiral center in the R units and wherein a particular enantiomer is selected, for example, one of the two enantiomeric R units having the formula:

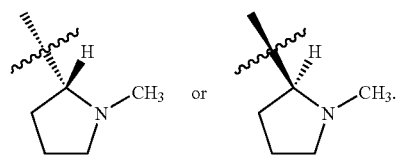

The second aspect of the second category of R units relates to heterocyclic units wherein the linking group L is bonded to a carbon atom, said units having the formula:

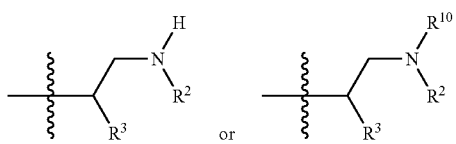

wherein $R^2$ and $R^3$ are taken together to form a heterocycle having from 3 to 7 atoms optionally substituted with one or more substituents; $R^{10}$ is methyl, ethyl, 1-propyl, 2-propyl, or phenyl. Non-limiting examples of this aspect includes pyrrolidin-3-yl, N-methyl-pyrrolidin-3-yl, piperidin-3-yl, N-methylpiperidin-3-yl, morpholin-2-yl, and N-methylmorpholin-2-yl.

The third aspect of the second category of R units relates to heterocyclic units wherein the linking group L is bonded to a carbon atom, said units having the formula:

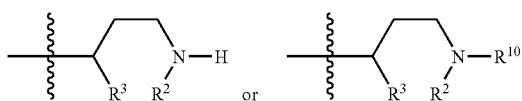

wherein $R^2$ and $R^3$ are taken together to form a heterocycle having from 3 to 7 atoms optionally substituted with one or more substituents; $R^{10}$ is methyl, ethyl, 1-propyl, 2-propyl, or phenyl. Non-limiting examples of this aspect include piperidin-4-yl, N-methylpiperidin-4-yl, and 2,2,6,6-tetramethyl-piperidin-4-yl.

$R^1$ is substituted or unsubstituted phenyl having the formula:

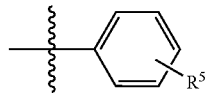

$R^5$ is hydrogen or one or more independently chosen substitutes for hydrogen, $R^5$ has the formula:

the index y has the value 0 when $L^1$ is absent, and the value 1 when $L^1$ is present;

$R^6$ is a unit chosen from:
  i) hydrogen;
  ii) halogen;
  iii) nitro;
  iv) hydroxy;
  v) amino or mono- or di-substituted ($C_1$-$C_4$ linear or branched alkyl)amino;
  vi) substituted or unsubstituted $C_1$-$C_4$ linear or branched alkyl;
  vii) substituted or unsubstituted $C_1$-$C_4$ linear or branched alkoxy;
  viii) substituted or unsubstituted phenyl;
  ix) substituted or unsubstituted $C_2$-$C_5$ heterocyclic;
  x) substituted or unsubstituted $C_3$-$C_9$ heteroaryl;
  xi) cyano; or
  xii) $CH_mX_{3-m}$ wherein X is halogen and m is from 0 to 2.

The first category of $R^1$ relates to substituted phenyl units wherein $L^1$ is absent (the index y is equal to 0) and $R^5$ comprises one or more substitutes for hydrogen each of which is independently chosen from:
  ii) halogen; —F, —Cl, —Br, and —I;
  iii) nitro; —$NO_2$;
  iv) hydroxy; —OH;
  v) amino or mono- or di-substituted ($C_1$-$C_4$ linear or branched alkyl)amino; inter alia, —$NH_2$, —$NH(CH_3)$, and —$N(CH_3)_2$;
  vi) substituted or unsubstituted $C_1$-$C_4$ linear or branched alkyl;
  vii) substituted or unsubstituted $C_1$-$C_4$ linear or branched alkoxy.

The first aspect of Category one of $R^1$ relates to units which are substituted by one or more units from groups (ii)-(vii). Non-limiting examples of this aspect include 3-chlorophenyl, 4-chlorophenyl, 3,4-dichlorophenyl, 3-chloro-4-methylphenyl, 3-chloro-4-fluorophenyl, 3,4-difluorophenyl, 3-trifluoromethylphenyl, 3-trifluoromethyl-4-chlorophenyl, 3-methoxyphenyl, 3-methylphenyl, 3-ethylphenyl, and 3-isopropylphenyl.

The second aspect of Category one of $R^1$ relates to units which are substituted by one or more halogen atom, for example, —F, —Cl, —Br, and —I. Non-limiting examples of this aspect include 2-fluorophenyl, 3-fluorophenyl, 4-fluorophenyl, 2,3-difluorophenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 2,3-dichlorophenyl, 2,4-dichlorophenyl, 2,5-dichlorophenyl, 2,6-dichlorophenyl, 2,3,4-trichlorophenyl, 2,3,5-trichlorophenyl, 2,3,6-trichlorophenyl, 2,4,5-trichlorophenyl, and 2,4,6-trichlorophenyl.

The third aspect of Category one of $R^1$ relates to units which are substituted by one or more $C_1$-$C_4$ linear or branched alkyl, for example, methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$). Non-limiting examples of this aspect include 2-methylphenyl, 4-methylphenyl, 2,3-dimethyl-phenyl, 2,4-dimethylphenyl, 2,5-dimethylphenyl, 2,6-dimethylphenyl, 3,4-dimethyl-phenyl, 2,3,4-trimethylphenyl, 2,3,5-trimethyl-phenyl, 2,3,6-trimethylphenyl, 2,4,5-trimethylphenyl, 2,4,6-trimethylphenyl, 2-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethyl-phenyl, 2,3,5-triethylphenyl, 2,3,6-triethylphenyl, 2,4,5-triethylphenyl, and 2,4,6-triethyl-phenyl.

The fourth aspect of Category one of $R^1$ relates to units which are substituted by one or more $C_1$-$C_4$ linear or branched alkoxy, for example, methoxy ($C_1$), ethoxy ($C_2$), n-propoxy ($C_3$), iso-propoxy ($C_3$), n-butoxy ($C_4$), sec-butoxy ($C_4$), iso-butoxy ($C_4$), and tert-butoxy ($C_4$). Non-limiting examples of this aspect include 2-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 2,3,4-trimethoxyphenyl, 2,3,5-trimethoxyphenyl, 2,3,6-trimethoxy-phenyl, 2,4,5-trimethoxyphenyl, and 2,4,6-trimethoxyphenyl.

The fifth aspect of Category one of $R^1$ relates to units which are substituted by one or more hydroxy units, non-limiting examples of this aspect include 2-hydroxy-phenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxy-phenyl, 2,3,4-trihydroxyphenyl, 2,3,5-trihydroxy-phenyl, 2,3,6-trihydroxyphenyl, 2,4,5-trihydroxyphenyl, and 2,4,6-trihydroxyphenyl.

Other aspects of Category one of $R^1$ include combinations of $R^5$ substituents which comprise substitute classes (ii)-(vii) not specifically exemplified herein.

The second category of $R^1$ relates to substituted core phenyl units wherein the index y is equal to 0 or 1 and $R^5$ comprises one or more substitutes for hydrogen each of which is independently chosen from units which comprise:
viii) substituted or unsubstituted phenyl; or
ix) substituted or unsubstituted $C_3$-$C_9$ heteroaryl units.

Substituted or unsubstituted phenyl units are present in the second category of $R^1$ when linked to the core phenyl units by way of a linking unit $L^1$.

The core $C_3$-$C_9$ heteroaryl rings of the second category of $R^1$ encompass the following non-limiting examples of substituted and unsubstituted rings: triazinyl ($C_3$), thiazoyl ($C_3$), 1H-imidazoyl ($C_3$), furanyl ($C_4$), thiophenyl ($C_4$), pyrimidinyl ($C_4$), 2-phenylpyrimidinyl ($C_4$), pyridinyl ($C_5$), 3-methylpyridinyl ($C_5$), 4-dimethylaminopyridinyl ($C_5$), 7H-purinyl ($C_5$), 9H-purinyl ($C_5$), 6-amino-9H-purinyl ($C_5$), 5H-pyrrolo[3,2-d]pyrimidinyl ($C_6$), 7H-pyrrolo[2,3-d]pyrimidinyl ($C_6$), pyrido[2,3-d]pyrimidinyl ($C_7$), 2-phenylbenzo[d]thiazolyl ($C_7$), 4,5,6,7-tetrahydro-1-H-indolyl ($C_9$), quinoxalinyl ($C_8$), 5-methylquinoxalinyl ($C_8$), quinazolinyl ($C_8$), 6,7-dihydro-5H-[1]pyridine ($C_8$), quinolinyl ($C_9$), 8-hydroxy-quinolinyl ($C_9$), and isoquinolinyl ($C_9$).

The first aspect of the second category of $R^1$ relates to units wherein the linking unit $L^1$ is absent (the index y is equal to 0), non-limiting examples of which include units chosen from: 2-(pyrimidin-2-yl)phenyl, 2-(pyrimidin-3-yl)phenyl, 2-(pyrimidin-4-yl)phenyl, 3-(pyrimidin-2-yl)phenyl, 3-(pyrimidin-3-yl)phenyl, 3-(pyrimidin-4-yl)phenyl, 4-(pyrimidin-2-yl)phenyl, 4-(pyrimidin-3-yl)phenyl, 4-(pyrimidin-4-yl)phenyl, 2-(pyridin-2-yl)phenyl, 2-(pyridin-3-yl)phenyl, 2-(pyridin-4-yl)phenyl, 3-(pyridin-2-yl)phenyl, 3-(pyridin-3-yl)phenyl, 3-(pyridin-4-yl)phenyl, 4-(pyridin-2-yl)phenyl, 4-(pyridin-3-yl)phenyl, and 4-(pyridin-4-yl)phenyl.

The second aspect of the second category of $R^1$ relates to units wherein $L^1$ is a unit having the formula:

$$-[CH_2]_j-$$

wherein the index j is equal to 1 or 2, non-limiting examples of which include units chosen from: 2-[(pyrimidin-2-yl)phenyl]methyl, 2-[(pyrimidin-3-yl)phenyl]methyl, 2-[(pyrimidin-4-yl)phenyl]methyl, 3-[(pyrimidin-2-yl)phenyl]methyl, 3-[(pyrimidin-3-yl)phenyl]methyl, 3-[(pyrimidin-4-yl)phenyl]methyl, 4-[(pyrimidin-2-yl)phenyl]methyl, 4-[(pyrimidin-3-yl)phenyl]methyl, 4-[(pyrimidin-4-yl)phenyl]methyl, 2-[(pyridin-2-yl)phenyl]methyl, 2-[(pyridin-3-yl)phenyl]methyl, 2-[(pyridin-4-yl)phenyl]methyl, 3-[(pyridin-2-yl)phenyl]methyl, 3-[(pyridin-3-yl)phenyl]methyl, 3-[(pyridin-4-yl)phenyl]-methyl, 4-[(pyridin-2-yl)phenyl]methyl, 4-[(pyridin-3-yl)phenyl]methyl, and 4-[(pyridin-4-yl)phenyl]methyl.

The third aspect of the second category of $R^1$ relates to units wherein $L^1$ is a unit having the formula:

$$-O[CH_2]_k-$$

wherein the index k is equal to 1 or 2, non-limiting examples of which include $R^5$ units chosen from: 2-(pyrimidin-2-yl)phenyl, 2-(pyrimidin-3-yl)phenyl, 2-(pyrimidin-4-yl)phenyl, 3-(pyrimidin-2-yl)phenyl, 3-(pyrimidin-3-yl)phenyl, 3-(pyrimidin-4-yl)phenyl, 4-(pyrimidin-2-yl)phenyl, 4-(pyrimidin-3-yl)phenyl, 4-(pyrimidin-4-yl)phenyl, 2-(pyridin-2-yl)phenyl, 2-(pyridin-3-yl)phenyl, 2-(pyridin-4-yl)phenyl, 3-(pyridin-2-yl)phenyl, 3-(pyridin-3-yl)phenyl, 3-(pyridin-4-yl)phenyl, 4-(pyridin-2-yl)phenyl, 4-(pyridin-3-yl)phenyl, and 4-(pyridin-4-yl)phenyl.

The fourth aspect of the second category of $R^1$ relates to units wherein $L^1$ is a unit having the formula:

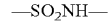

$$-SO_2NH-$$

and $R^5$ is a unit chosen from:
i) hydrogen;
ii) $C_1$-$C_4$ linear or branched alkyl;
iii) substituted or unsubstituted phenyl; and
iv) substituted or unsubstituted heteroaryl.

The first iteration of the fourth aspect of category two of $R^1$ units encompasses $R^5$ units which are chosen from:
i) hydrogen; or
ii) $C_1$-$C_4$ linear or branched alkyl.

Non-limiting examples of $R^1$ units encompassed within this iteration include: benzene-sulfonamide, N-methyl-benzenesulfonamide, N-ethyl-benzenesulfon-amide, N-(n-propyl)-benzenesulfonamide, N-(iso-propyl)-benzenesulfonamide, N-(n-butyl)-benzenesulfonamide, N-(sec-butyl)-benzenesulfonamide, N-(iso-butyl)-benzenesulfonamide, and N-(tert-butyl)-benzenesulfonamide.

The second iteration of the fourth aspect of category two of $R^1$ units encompasses $R^5$ units which are chosen from:
iii) substituted or unsubstituted phenyl; or
iv) substituted or unsubstituted heteroaryl.

Non-limiting examples of $R^1$ units encompassed within this iteration include: N-phenyl-benzene-sulfonamide, N-(pyrimidin-2-yl)-benzenesulfonamide, N-(pyrimidin-4-yl)-benzenesulfonamide, N-(pyrimidin-5-yl)-benzenesulfonamide, N-(pyridin-2-yl)-benzenesulfonamide, N-(pyridin-3-yl)-benzenesulfonamide, and N-(pyridin-4-yl)-benzenesulfonamide.

The fifth aspect of the second category of $R^1$ relates to units wherein $L^1$ is a unit having the formula:

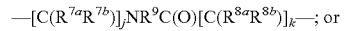

$$-[C(R^{7a}R^{7b})]_j NR^9 C(O)[C(R^{8a}R^{8b})]_k-; \text{ or}$$

$$-[C(R^{7a}R^{7b})]_j C(O)NR^9 [C(R^{8a}R^{8b})]_k-$$

wherein $R^{7a}$, $R^{7b}$, $R^{8a}$, $R^{8b}$, and $R^9$ are each independently hydrogen, methyl, or ethyl; the indices j and k are each independently from 0 to 3.

The first iteration of the fifth aspect of the second category of $R^1$ units relates to $R^1$ units wherein $R^6$ units are linked to the phenyl ring by way of a $L^1$ unit chosen from units having the formula:

i) —NH(CO)—;
ii) —NH(CO)CH$_2$—; and
iii) —C(O)NH—;

and $R^6$ comprises a unit chosen from:
viii) substituted or unsubstituted phenyl; or
x) substituted or unsubstituted C$_3$-C$_9$ heteroaryl.

Non-limiting examples of the first iteration of the fifth aspect of the second category of $R^1$ units includes substituted or unsubstituted phenyl units linked with amide bond linking units having the formula —C(O)NH— or —NH(CO)—. The following are examples of $R^5$ units which are amide bond-linked substituted or unsubstituted phenyl units substituted at the 3-position of the core phenyl ring:

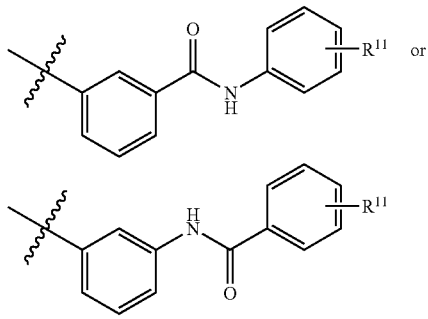

wherein $R^{11}$ comprises one or more of the $R^{12}$ substitutions for hydrogen as defined and exemplified herein above.

The third category of $R^1$ relates to substituted phenyl units wherein $L^1$ is absent (the index y is equal to 0) and $R^5$ comprises one or more substitutes for hydrogen each of which is independently chosen from units which comprise:
viii) substituted or unsubstituted C$_2$-C$_5$ heterocyclic units.

The core C$_2$-C$_5$ heterocyclic rings of the third category of $R^1$ encompass the following unsubstituted rings: aziridinyl (C$_2$), [1,2,3]triazolyl (C$_2$), [1,2,4]triazolyl (C$_2$), urazolyl (C$_2$), oxazolyl (C$_3$), azetidinyl (C$_3$), pyrazolidinyl (C$_3$), imidazolidinyl (C$_3$), oxazolidinyl (C$_3$), isoxazolinyl (C$_3$), oxazolyl (C$_3$) isoxazolyl (C$_3$), thiazolidinyl (C$_3$), thiazolyl (C$_3$), imidazolidinonyl (C$_3$), isothiazolyl (C$_3$), isothiazolinyl (C$_3$), oxathiazolidinonyl (C$_3$), oxazolidinonyl (C$_3$), hydantoinyl (C$_3$), tetrahydrofuranyl (C$_4$), pyrrolidinyl (C$_4$), tetrahydrothiophenyl (C$_4$), morpholinyl (C$_4$), piperazinyl (C$_4$), piperidinyl (C$_4$), dihydropyranyl (C$_5$), tetrahydropyranyl (C$_5$), and piperidin-2-onyl (valerolactam) (C$_5$). However, the C$_2$-C$_5$ heterocyclic rings described herein can be substituted with one or more units chosen from:

i) C$_1$-C$_4$ linear or branched alkyl, for example, methyl (C$_1$), ethyl (C$_2$), n-propyl (C$_3$), iso-propyl (C$_3$), n-butyl (C$_4$), sec-butyl (C$_4$), iso-butyl (C$_4$), and tert-butyl (C$_4$); or
ii) amino —NH$_2$, or mono- or di-[C$_1$-C$_4$ linear or branched alkyl]substituted amino, for example, —NH$_2$; —NHCH$_3$; —N(CH$_3$)$_2$; —NH(CH$_2$CH$_3$); —N(CH$_2$CH$_3$)$_2$; —N(CH$_3$)(CH$_2$CH$_3$); —NH(CH$_2$CH$_2$CH$_3$); —N[CH(CH$_3$)$_2$]$_2$; —N(CH$_2$CH$_2$CH$_3$)$_2$; —NH[CH(CH$_3$)$_2$]; —N(CH$_2$CH$_2$CH$_3$)[CH(CH$_3$)$_2$]; —N(CH$_3$)(CH$_2$CH$_2$CH$_3$); —N(CH$_2$CH$_3$)(CH$_2$CH$_2$CH$_3$); —N[C(CH$_3$)$_3$]$_2$; —N(CH$_3$)[CH(CH$_3$)$_2$]; —N(CH$_2$CH$_3$)[CH(CH$_3$)$_2$]$_2$; —NH[C(CH$_3$)$_3$]; —NH(CH$_2$CH$_2$CH$_2$CH$_3$); —N(CH$_2$CH$_2$CH$_2$CH$_3$)$_2$; —NH[CH$_2$CH(CH$_3$)$_2$]; —N[CH$_2$CH(CH$_3$)$_2$]$_2$; —NH[CH(CH$_3$)CH$_2$CH$_3$]; —N[CH(CH$_3$)CH$_2$CH$_3$]$_2$; —N(CH$_2$CH$_2$CH$_2$CH$_3$)[CH$_2$CH(CH$_3$)$_2$]; —N(CH$_2$CH$_2$CH$_2$CH$_3$)[C(CH$_3$)$_3$]; and —N(CH$_2$CH$_2$CH$_2$CH$_3$)[CH(CH$_3$)CH$_2$CH$_3$]

L is a linking unit having the formula:

wherein each $R^{4a}$ and $R^{4b}$ unit is independently chosen from:
i) hydrogen; or
ii) C$_1$-C$_4$ linear, branched, or cyclic alkyl; for example, methyl (C$_1$), ethyl (C$_2$), n-propyl(C$_3$), iso-propyl (C$_3$), cyclopropyl (C$_3$), n-butyl (C$_4$), iso-butyl (C$_4$), sec-butyl (C$_4$), and tert-butyl (C$_4$);

the index n is from 1 to 4. The index n indicates the number of units which comprise L linking units, for example, a linking unit having the formula —CH$_2$— (methylene) would have an index n equal to 1. A linking unit having the formula —CH$_2$CH$_2$— (ethylene) or the unit having the formula —CH(CH$_3$)CH$_2$— (1-methylethylene) each have an index n equal to 2.

The first category of L units relates to unsubstituted alkylene units chosen from:
i) —CH$_2$—, methylene;
ii) —CH$_2$CH$_2$—, ethylene;
iii) —CH$_2$CH$_2$CH$_2$—, propylene; and
iv) —CH$_2$CH$_2$CH$_2$CH$_2$—, butylene.

The first aspect of the first category of L units encompasses linking groups which are —CH$_2$CH$_2$CH$_2$—, propylene; as exemplified in the generic formula:

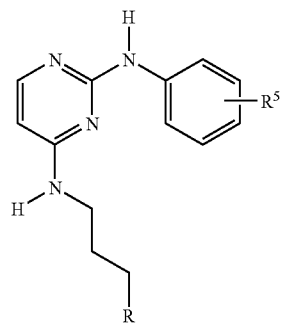

The second aspect of the first category of L units encompasses linking groups which are —CH$_2$CH$_2$—, ethylene.

The second category of L units relates to alkyl substituted alkylene units chosen from:
i) —CH(CH$_3$)CH$_2$—, 1-methylethylene;
ii) —CH$_2$CH(CH$_3$)—, 2-methylethylene;
iii) —CH(CH$_3$)CH$_2$CH$_2$—, 1-methylpropylene;
iv) —CH$_2$CH(CH$_3$)CH$_2$—, 2-methylpropylene; and
v) —CH$_2$C(CH$_3$)$_2$CH$_2$—, 2,2-dimethylpropylene.

The first aspect of the second category of L units encompasses linking groups which are —CH(CH$_3$)CH$_2$CH$_2$—, 1-methylpropylene; as exemplified in the generic formula:

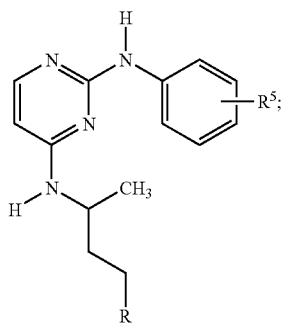

wherein the above formula encompasses both the R and the S enantiomers of the linking unit.

$L^1$ is a linking unit which when present provides $R^5$ units with the formula:

wherein y is equal to 1 when $L^1$ is present.

$L^1$ is a linking unit chosen from:
i) —[C($R^{7a}R^{7b}$)]$_j$—;
ii) —[C($R^{7a}R^{7b}$)]$_j$O[C($R^{8a}R^{8b}$)]$_k$—;
iii) —[C($R^{7a}R^{7b}$)]$_j$N$R^9$SO$_2$[C($R^{8a}R^{8b}$)]$_k$—;
iv) —[C($R^{7a}R^{7b}$)]$_j$SO$_2$N$R^9$[C($R^{8a}R^{8b}$)]$_k$—;
v) —[C($R^{7a}R^{7b}$)]$_j$N$R^9$C(O)[C($R^{8a}R^{8b}$)]$_k$—;
vi) —[C($R^{7a}R^{7b}$)]$_j$C(O)N$R^9$[C($R^{8a}R^{8b}$)]$_k$; or
vii) —[C($R^{7a}R^{7b}$)]$_j$SO$_2$N$R^9$[C($R^{7a}R^{7b}$)]$_k$—;

$R^{7a}$, $R^{7b}$, $R^{8a}$, $R^{8b}$, and $R^9$ are each independently hydrogen, methyl, or ethyl; the indices j and k are each independently from 0 to 3; the index y is 0 or 1.

The various categories, aspects, iterations, and examples of $L^1$ can be found in the definitions of $R^1$ and in the examples and tables described and listed herein below.

Synthesis Procedure

The compounds of the present invention can be prepared by the following general procedure, the formulator adjusting the reaction conditions as is necessary and which one skilled in the art will be able to accomplish without undo experimentation.

Step 1: Preparation of intermediate 2-(methylthio)pyrimidine-4(3H)-one. This compound can be used in the preparation of each analog encompassed by the present invention. The general procedure follows.

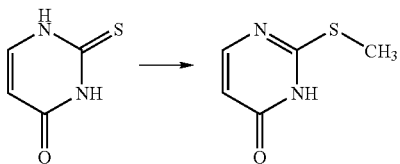

To a solution of sodium hydroxide (8 g, 200 mmol) in $H_2O$ (75 mL) at room temperature is added thiouridine (14.2 g, 100 mmol). The resulting mixture is stirred at room temperature for 20 minutes. Methyl iodide (6.86 mL, 110 mmol) in THF (10 mL) is added dropwise slowly and the mixture is stirred at room temperature for 18 hours. A white solid forms upon acidifying the mixture to pH 5 with glacial acetic acid. At this point the mixture is cooled in an ice bath and allowed to stand for approximately 2 hours after which the final product separates as a white solid and can be collected by filtration. First crop of crystals typically yields the desired product in an excess of 60% yield. $^1$H NMR (DMSO-$d_6$, 300 MHz): δ 2.45 (s, 3H), 6.07 (d, J=6.6 Hz, 1H), 7.85 (d, J=6.6 Hz, 1H).

Step 2: Formation of 2-anilino Intermediate.

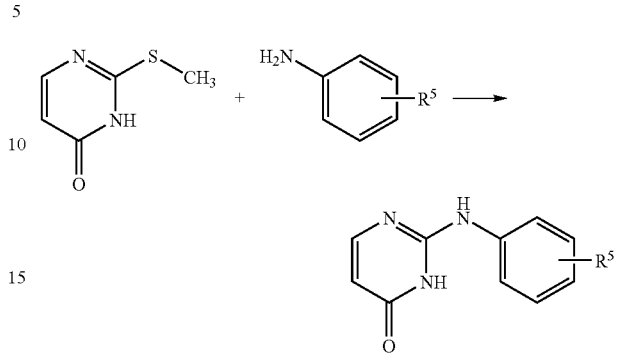

2-(Substituted or unsubstituted phenylamino)pyrimidin-4 (3H)-one: To a 2-(methyl-thio)pyrimidine-4(3H)-one (14.2 g, 100 mmol) in diglyme (60 mL) is added the substituted or unsubstituted aniline of choice (200 mmol). The resulting mixture is heated to reflux and stirred for approximately 18 hours. The product which typically forms as a solid upon cooling the mixture to room temperature, is washed with solvent (pentane, hexane, or isopentane). However, solvent can be added to the reaction mixture to induce crystallization if necessary.

Step 3. Formation of 4-chloro-2-anilino Intermediate.

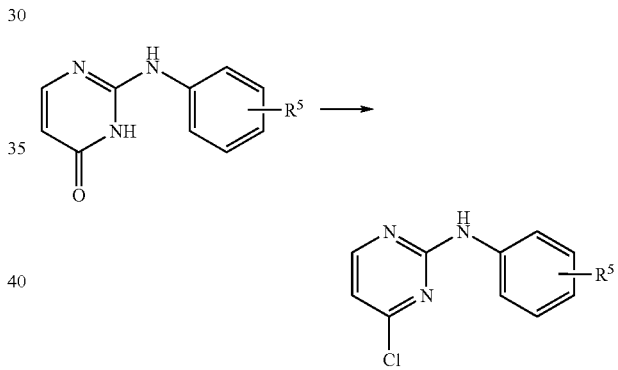

2-(Substituted or unsubstituted phenylamino)-4-chloropyrimidine: To a 2-(Substituted or unsubstituted phenylamino)pyrimidin-4(3H)-one (5.02 g, 22.6 mmol) and N,N-dimethyl-aniline (450 mL) is added of phosphorus oxychloride (450 mL). The resulting mixture is heated to reflux for 15 minutes, cooled to room temperature and concentrated in vacuo. The residue is neutralized to pH 7 with 1M NaOH (aqueous). The organic layer is extracted with EtOAc (3×250 mL). The combined organic layers are dried (MgSO$_4$) and concentrated in vacuo. The residue can be conveniently purified over silica (5% EtOAc in hexanes) to afford the desired compound.

Alternatively, the 4-chloro-2-anilino intermediate can be synthesized the following way:

2-(Substituted or unsubstituted phenylamino)-4-chloropyrimidine: To a 2-(substituted or unsubstituted phenylamino)pyrimidin-4(3H)-one (3.00 g, 13.5 mmol) in toluene (30 mL) is added N,N-dimethyl-aniline (3.57 mL, 28.4 mmol) and phosphorus oxychloride (1.24 mL, 13.5 mmol). The resulting mixture is heated to reflux for 15 minutes, cooled to room temperature and neutralized to pH 7 with 1M NaOH (aqueous). The organic layer is extracted with EtOAc (3×250 mL). The combined organic layers are dried (MgSO$_4$) and concentrated in vacuo. The residue can be conveniently purified over silica (5% EtOAc in hexanes) to afford the desired compound.

Step 4. Formation of Final Compounds (Analogs) of the Present Invention.

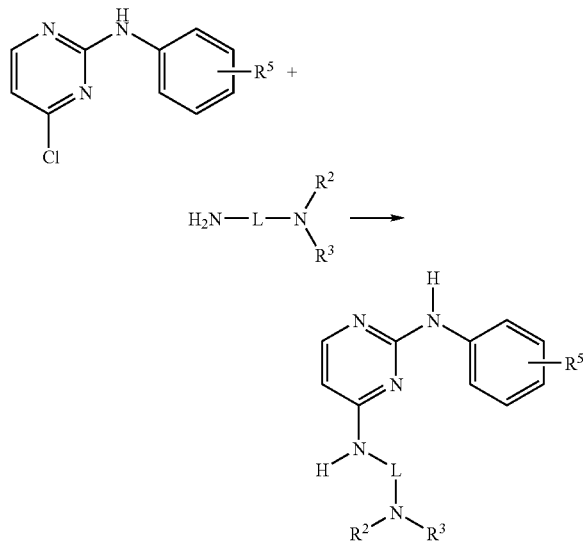

To the 2-(Substituted or unsubstituted phenylamino)pyrimidin-4(3H)-one formed in Step (2) (100 mmol) in THF (500 mL) is added diisopropylethylamine (200 mmol) followed by the desired diamine (200 mmol). The resulting mixture is heated to reflux for approximately 18 hours. The reaction is cooled to room temperature and concentrated in vacuo. The residue which forms is diluted with water and extracted with solvent. The combined organic layers are dried ($MgSO_4$) and concentrated in vacuo. This residue can be crystallized or purified over silica to afford the final compound.

Schemes I-IV herein below provide illustrative examples of the preparation of compounds encompassed by the various categories of the present invention.

The analogs (compounds) of the present invention are arranged into several categories to assist the formulator in applying a rational synthetic strategy for the preparation of analogs which are not expressly examplified herein. The arrangement into categories does not imply increased or decreased efficacy for any of the compositions of matter described herein.

Analog Categories

The compounds which comprise Category I of the present invention are 2,4-di-aminopyrimidines having the formula:

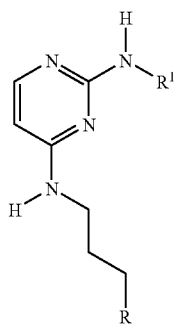

wherein linking group L is a propylene ($-CH_2CH_2CH_2-$) unit and R units are heterocyclic units attached to the core scaffold by way of a ring nitrogen atom. The first aspect of Category I encompasses $R^1$ units which are phenyl units substituted by one or more $R^5$ units chosen from:
  i) halogen; —F, —Cl, —Br, and —I;
  ii) nitro; —$NO_2$;
  iii) hydroxy; —OH;
  iv) amino or mono- or di-(substituted $C_1$-$C_4$ alkyl)amino; inter alia, —$NH_2$, —$NH(CH_3)$, and —$N(CH_3)_2$,
  v) substituted or unsubstituted $C_1$-$C_4$ linear or branched alkyl;
  vi) substituted or unsubstituted $C_1$-$C_4$ linear or branched alkoxy;
which are further exemplified herein below in Table I.

TABLE I

| No | R | $R^1$ |
|---|---|---|
| 1 | pyrrolidin-1-yl | 3-chlorophenyl |
| 2 | pyrrolin-1-yl | 3-chlorophenyl |
| 3 | imidazolidin-1-yl | 3-chlorophenyl |
| 4 | imidazolin-1-yl | 3-chlorophenyl |
| 5 | pyrazolidin-1-yl | 3-chlorophenyl |
| 6 | pyrazolin-1-yl | 3-chlorophenyl |
| 7 | piperidin-1-yl | 3-chlorophenyl |
| 8 | piperazin-1-yl | 3-chlorophenyl |
| 9 | 4-methylpiperazin-1-yl | 3-chlorophenyl |
| 10 | morpholin-4-yl | 3-chlorophenyl |
| 11 | pyrrolidin-1-yl | 4-chlorophenyl |
| 12 | pyrrolin-1-yl | 4-chlorophenyl |
| 13 | imidazolidin-1-yl | 4-chlorophenyl |
| 14 | imidazolin-1-yl | 4-chlorophenyl |
| 15 | pyrazolidin-1-yl | 4-chlorophenyl |
| 16 | pyrazolin-1-yl | 4-chlorophenyl |
| 17 | piperidin-1-yl | 4-chlorophenyl |
| 18 | piperazin-1-yl | 4-chlorophenyl |
| 19 | 4-methylpiperazin-1-yl | 4-chlorophenyl |
| 20 | morpholin-4-yl | 4-chlorophenyl |
| 21 | pyrrolidin-1-yl | 3,4-dichlorophenyl |
| 22 | pyrrolin-1-yl | 3,4-dichlorophenyl |
| 23 | imidazolidin-1-yl | 3,4-dichlorophenyl |
| 24 | imidazolin-1-yl | 3,4-dichlorophenyl |
| 25 | pyrazolidin-1-yl | 3,4-dichlorophenyl |
| 26 | pyrazolin-1-yl | 3,4-dichlorophenyl |
| 27 | piperidin-1-yl | 3,4-dichlorophenyl |
| 28 | piperazin-1-yl | 3,4-dichlorophenyl |
| 29 | 4-methylpiperazin-1-yl | 3,4-dichlorophenyl |
| 30 | morpholin-4-yl | 3,4-dichlorophenyl |
| 31 | pyrrolidin-1-yl | 3-chloro-4-methylphenyl |
| 32 | pyrrolin-1-yl | 3-chloro-4-methylphenyl |
| 33 | imidazolidin-1-yl | 3-chloro-4-methylphenyl |
| 34 | imidazolin-1-yl | 3-chloro-4-methylphenyl |
| 35 | pyrazolidin-1-yl | 3-chloro-4-methylphenyl |
| 36 | pyrazolin-1-yl | 3-chloro-4-methylphenyl |
| 37 | piperidin-1-yl | 3-chloro-4-methylphenyl |
| 38 | piperazin-1-yl | 3-chloro-4-methylphenyl |
| 39 | 4-methylpiperazin-1-yl | 3-chloro-4-methylphenyl |
| 40 | morpholin-4-yl | 3-chloro-4-methylphenyl |
| 41 | pyrrolidin-1-yl | 3-chloro-4-fluorophenyl |
| 42 | pyrrolin-1-yl | 3-chloro-4-fluorophenyl |
| 43 | imidazolidin-1-yl | 3-chloro-4-fluorophenyl |
| 44 | imidazolin-1-yl | 3-chloro-4-fluorophenyl |
| 45 | pyrazolidin-1-yl | 3-chloro-4-fluorophenyl |
| 46 | pyrazolin-1-yl | 3-chloro-4-fluorophenyl |
| 47 | piperidin-1-yl | 3-chloro-4-fluorophenyl |
| 48 | piperazin-1-yl | 3-chloro-4-fluorophenyl |
| 49 | 4-methylpiperazin-1-yl | 3-chloro-4-fluorophenyl |
| 50 | morpholin-4-yl | 3-chloro-4-fluorophenyl |
| 51 | pyrrolidin-1-yl | 3,4-difluorophenyl |
| 52 | pyrrolin-1-yl | 3,4-difluorophenyl |
| 53 | imidazolidin-1-yl | 3,4-difluorophenyl |
| 54 | imidazolin-1-yl | 3,4-difluorophenyl |
| 55 | pyrazolidin-1-yl | 3,4-difluorophenyl |
| 56 | pyrazolin-1-yl | 3,4-difluorophenyl |
| 57 | piperidin-1-yl | 3,4-difluorophenyl |
| 58 | piperazin-1-yl | 3,4-difluorophenyl |

TABLE I-continued

| No | R | R¹ |
|----|---|-----|
| 59 | 4-methylpiperazin-1-yl | 3,4-difluorophenyl |
| 60 | morpholin-4-yl | 3,4-difluorophenyl |
| 61 | pyrrolidin-1-yl | 3-$CF_3$-phenyl |
| 62 | pyrrolin-1-yl | 3-$CF_3$-phenyl |
| 63 | imidazolidin-1-yl | 3-$CF_3$-phenyl |
| 64 | imidazolin-1-yl | 3-$CF_3$-phenyl |
| 65 | pyrazolidin-1-yl | 3-$CF_3$-phenyl |
| 66 | pyrazolin-1-yl | 3-$CF_3$-phenyl |
| 67 | piperidin-1-yl | 3-$CF_3$-phenyl |
| 68 | piperazin-1-yl | 3-$CF_3$-phenyl |
| 69 | 4-methylpiperazin-1-yl | 3-$CF_3$-phenyl |
| 70 | morpholin-4-yl | 3-$CF_3$-phenyl |
| 71 | pyrrolidin-1-yl | 3-$CF_3$-4-Cl-phenyl |
| 72 | pyrrolin-1-yl | 3-$CF_3$-4-Cl-phenyl |
| 73 | imidazolidin-1-yl | 3-$CF_3$-4-Cl-phenyl |
| 74 | imidazolin-1-yl | 3-$CF_3$-4-Cl-phenyl |
| 75 | pyrazolidin-1-yl | 3-$CF_3$-4-Cl-phenyl |
| 76 | pyrazolin-1-yl | 3-$CF_3$-4-Cl-phenyl |
| 77 | piperidin-1-yl | 3-$CF_3$-4-Cl-phenyl |
| 78 | piperazin-1-yl | 3-$CF_3$-4-Cl-phenyl |
| 79 | 4-methylpiperazin-1-yl | 3-$CF_3$-4-Cl-phenyl |
| 80 | morpholin-4-yl | 3-$CF_3$-4-Cl-phenyl |
| 81 | pyrrolidin-1-yl | 3-methylphenyl |
| 82 | pyrrolin-1-yl | 3-methylphenyl |
| 83 | imidazolidin-1-yl | 3-methylphenyl |
| 84 | imidazolin-1-yl | 3-methylphenyl |
| 85 | pyrazolidin-1-yl | 3-methylphenyl |
| 86 | pyrazolin-1-yl | 3-methylphenyl |
| 87 | piperidin-1-yl | 3-methylphenyl |
| 88 | piperazin-1-yl | 3-methylphenyl |
| 89 | 4-methylpiperazin-1-yl | 3-methylphenyl |
| 90 | morpholin-4-yl | 3-methylphenyl |
| 91 | pyrrolidin-1-yl | 3-methoxyphenyl |
| 92 | pyrrolin-1-yl | 3-methoxyphenyl |
| 93 | imidazolidin-1-yl | 3-methoxyphenyl |
| 94 | imidazolin-1-yl | 3-methoxyphenyl |
| 95 | pyrazolidin-1-yl | 3-methoxyphenyl |
| 96 | pyrazolin-1-yl | 3-methoxyphenyl |
| 97 | piperidin-1-yl | 3-methoxyphenyl |
| 98 | piperazin-1-yl | 3-methoxyphenyl |
| 99 | 4-methylpiperazin-1-yl | 3-methoxyphenyl |
| 100 | morpholin-4-yl | 3-methoxyphenyl |
| 101 | pyrrolidin-1-yl | 3-ethylphenyl |
| 102 | pyrrolin-1-yl | 3-ethylphenyl |
| 103 | imidazolidin-1-yl | 3-ethylphenyl |
| 104 | imidazolin-1-yl | 3-ethylphenyl |
| 105 | pyrazolidin-1-yl | 3-ethylphenyl |
| 106 | pyrazolin-1-yl | 3-ethylphenyl |
| 107 | piperidin-1-yl | 3-ethylphenyl |
| 108 | piperazin-1-yl | 3-ethylphenyl |
| 109 | 4-methylpiperazin-1-yl | 3-ethylphenyl |
| 110 | morpholin-4-yl | 3-ethylphenyl |
| 111 | pyrrolidin-1-yl | 3-isopropylphenyl |
| 112 | pyrrolin-1-yl | 3-isopropylphenyl |
| 113 | imidazolidin-1-yl | 3-isopropylphenyl |
| 114 | imidazolin-1-yl | 3-isopropylphenyl |
| 115 | pyrazolidin-1-yl | 3-isopropylphenyl |
| 116 | pyrazolin-1-yl | 3-isopropylphenyl |
| 117 | piperidin-1-yl | 3-isopropylphenyl |
| 118 | piperazin-1-yl | 3-isopropylphenyl |
| 119 | 4-methylpiperazin-1-yl | 3-isopropylphenyl |
| 120 | morpholin-4-yl | 3-isopropylphenyl |

The compounds which comprise Category I of the present invention can be prepared by the procedure outlined herein below in Scheme I.

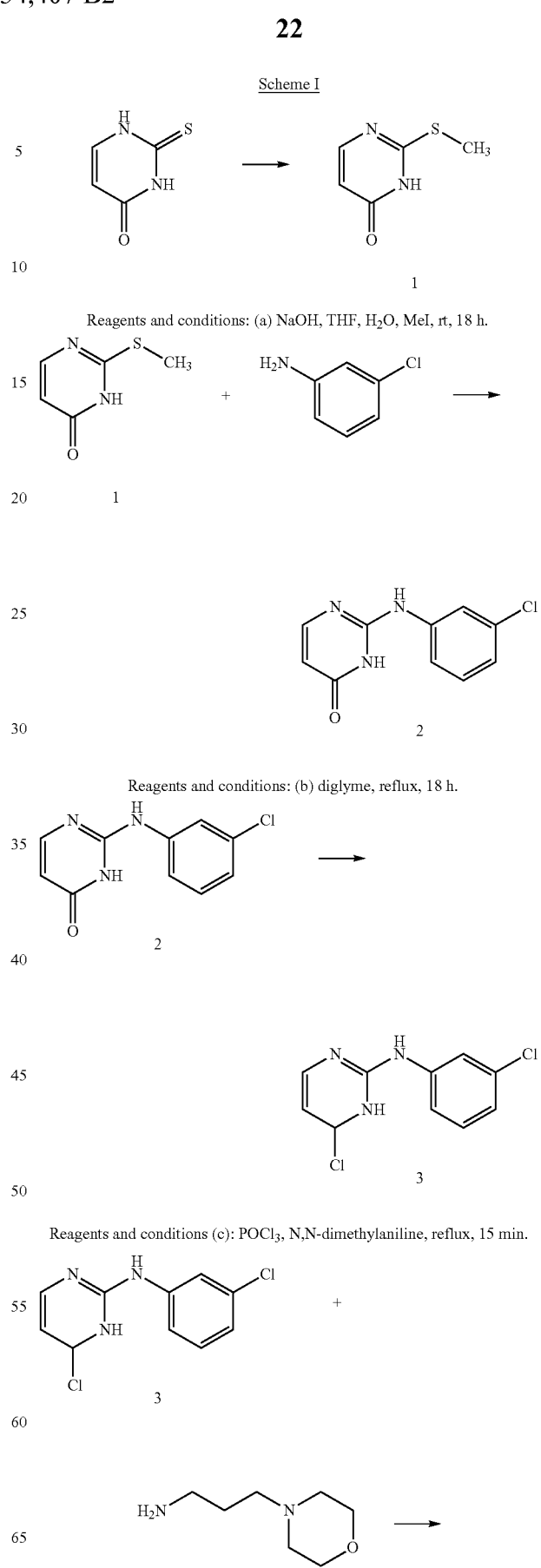

-continued

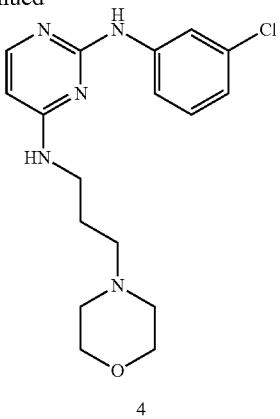

4

Reagents and conditions (d): DIPEA, THF, 80° C., 24 h

Example 1

N$^2$-(3-chlorophenyl)-N$^4$-(3-morpholin-4-yl-propyl)-pyrimidine-2,4-diamine (4)

Preparation of 2-(methylthio)pyrimidine-4(3H)-one (1): To a solution of sodium hydroxide (6.24 g, 156.07 mmol) in H$_2$O (55 mL) at room temperature is added thiouridine (10 g, 78.03 mmol). The resulting mixture is stirred at room temperature for 20 min. Methyl iodide (5.45 mL, 87.40 mmol) in THF (10 mL) is added dropwise slowly and the mixture is stirred at room temperature for 18 hours. A white solid forms upon acidifying the mixture to pH 5 with glacial acetic acid. The mixture is allowed to stand at 0° C. (ice bath) for 2 hours and filtered to afford 7.4 g (67% yield) of the desired compound. $^1$H NMR (DMSO-d$_6$, 300 MHz): δ 2.45 (s, 3H), 6.07 (d, J=6.6 Hz, 1H), 7.85 (d, J=6.6 Hz, 1H).

Preparation of 2-(3-chlorophenylamino)pyrimidin-4(3H)-one (2): To 2-(methylthio)pyrimidin-4(3H)-one, 1, (4.88 g, 34.37 mmol) in diglyme (20 mL) is added 3-chloroaniline (4.3 mL, 68.74 mmol). The resulting mixture is heated to reflux and stirred for 18 hours. A solid forms upon cooling the mixture to room temperature. The solid is washed with hexanes to afford 5.0 g (66% yield) of the desired compound. $^1$H NMR (DMSO-d$_6$, 300 MHz): δ 5.91 (d, J=5.7 Hz, 2H), 7.05 (d, J=7.5 Hz, 1H), 7.11 (br s, 1H), 7.32 (t, J=7.8, 15.9 Hz, 1H), 7.45 (d, J=7.8 Hz, 1H), 7.86 (d, J=4.5 Hz, 1H), 7.94 (s, 1H).

Preparation of 4-chloro-N-(3-chlorophenyl)pyrimidin-2-amine (3): To a 2-(substituted or unsubstituted phenylamino) pyrimidin-4(3H)-one (3.00 g, 13.5 mmol) in toluene (30 mL) is added N,N-dimethyl-aniline (3.57 mL, 28.4 mmol) and phosphorus oxychloride (1.24 mL, 13.5 mmol). The resulting mixture is heated to reflux for 15 minutes, cooled to room temperature and neutralized to pH 7 with 1M NaOH (aqueous). The organic layer is extracted with EtOAc (3×250 mL). The combined organic layers are dried (MgSO$_4$) and concentrated in vacuo. The residue is purified over silica (5% EtOAc in hexanes) to afford 2.0 g (61% yield) of the desired compound. $^1$H NMR (DMSO-d$_6$, 300 MHz): δ 7.06-7.04 (m, 2H), 7.34 (t, J=8.1, 1H), 7.65-7.61 (m, 1H), 7.93 (m, 1H), 8.50 (d, J=5.1 Hz, 1H), 10.26 (s, 1H).

Preparation of N$^2$-(3-chlorophenyl)-N$^4$-(3-morpholin-4-yl-propyl)-pyrimidine-2,4-diamine (4): To 4-chloro-N-(3-chlorophenyl)pyrimidin-2-amine, 3, (0.2 g, 0.84 mmol) in THF (4 mL) is added diisopropylethylamine (0.29 mL, 1.67 mmol) followed by 3-morpholino-propylamine (0.245 mL, 1.67 mmol). The resulting mixture was heated to reflux for 6 hours. Another 2 equivalents of 3-morpholinopropylamine (0.245 mL, 1.67 mmol) is added and the reaction heated to reflux and stirred for 18 hours. The resulting mixture is heated to reflux for 18 hours. The reaction is cooled to room temperature and concentrated in vacuo. The residue is diluted with 5 mL water and extracted with EtOAc (3×25 mL). The combined organic layers are dried (MgSO$_4$) and concentrated in vacuo. The residue is diluted with 5 mL water and extracted with EtOAc (3×25 mL). The combined organic layers are dried (MgSO$_4$) and concentrated in vacuo. This residue is purified over silica (6% MeOH in CH$_2$Cl$_2$ with 0.7% Et$_3$N) to afford 0.120 g (41% yield) of the desired compound. $^1$H NMR (DMSO-d$_6$, 300 MHz): δ 1.68-1.75 (m, 2H), 2.34-2.40 (m, 6H), 3.30-3.35 (m, 2H), 3.55-3.58 (m, 4H), 5.97 (d, J=5.7 Hz, 1H), 6.88 (d, J=7.2 Hz, 1H), 7.19-7.28 (m, 2H), 7.59 (d, J=7.2 Hz, 1H), 7.80 (br s, 1H), 8.13 (br s, 1H), 9.19 (br s, 1H). MS (ESI, pos. ion) m/z: 348 (M+1).

The following are non-limiting examples of compounds which comprise first aspect of Category I of the present invention, the characterization of which will assist the formulator in establishing the chemical formulae of compounds which are not specifically exemplified herein. Alternatively, these compounds may also be synthesized by the synthetic route or methods described later in Scheme II.

N$^2$-(3-Fluorophenyl)-N$^4$-(3-morpholin-4-yl-propyl)-pyrimidine-2,4-diamine: $^1$H NMR (CDCl$_3$, 300 MHz) δ 1.83 (q, J=6.3 Hz, 2H), 2.47-2.57 (m, 6H), 3.47 (bs, 2H), 3.78 (t, J=4.8 Hz, 1H), 5.88 (d, J=6.0 Hz, 1H), 6.68 (tt, J=3.3, 1.0 Hz, 1H), 7.12 (d, J=8.1 Hz, 1H), 7.20 (t, J=6.3 Hz, 1H), 7.70 (bs, 1H), 7.81 (dt, J=12.0, 2.4 Hz, 1H), 7.96 (d, J=5.4 Hz, 1H); HRMS calcd for C$_{17}$H$_{22}$FN$_5$O, 332.1887 m/z (M+H)$^+$; observed 332.1887 m/z.

N$^2$-(3-Nitrophenyl)-N$^4$-(3-morpholin-4-yl-propyl)-pyrimidine-2,4-diamine. Yield 96 mg (66%) $^1$H NMR (CDCl$_3$, 300 MHz): δ 1.87 (m, 2H), 2.54 (m, 6H), 3.59 (s, 2H), 3.77 (t, J=4.5 Hz, 4H), 5.94 (d, J=6.0 Hz, 1H), 6.37 (m, 1H), 7.42 (t, J=8.1 Hz, 1H), 7.67 (m, 1H), 7.81 (m, 1H), 7.91 (s, 1H), 7.97 (d, J=5.1 Hz, 1H). HRMS calcd for C17H22N6O3, 343.1882 m/z (M+H)$^+$; observed 343.1895 m/z.

N$^2$-(3-Bromophenyl)-N$^4$-(3-morpholin-4-yl-propyl)-pyrimidine-2,4-diamine. $^1$H NMR (CDCl$_3$, 300 MHz): δ 1.84 (m, 2H), 2.53 (m, 6H), 3.49 (bs, 2H), 3.78 (t, J=4.8 Hz, 4H), 5.88 (d, J=6.0 Hz, 1H), 6.318 (bs, 1H), 7.13 (m, 3H), 7.38 (d, J=7.2 Hz, 1H), 7.94 (d, J=4.8 Hz, 1H), 8.12 (s, 1H). HRMS calcd for C17H22N5OBr, 392.1086 m/z (M+H)$^+$; observed 392.1090 m/z.

N$^2$-(3-Aminophenyl)-N$^4$-(3-morpholin-4-yl-propyl)-pyrimidine-2,4-diamine. $^1$H NMR (CDCl$_3$, 300 MHz): δ 1.83 (m, 2H), 2.52 (m, 6H), 3.45 (m, 2H), 3.71 (bs, 2H), 3.79 (t, J=4.5 Hz, 4H), 5.83 (d, J=6.0 Hz, 1H), 6.12 (bs, 1H), 6.35 (m, 1H), 6.87 (s, 1H), 6.94 (m, 1H), 7.09 (t, J=8.1 Hz, 1H), 7.19 (t, J=2.4 Hz, 1H), 7.93 (d, J=6.0 Hz, 1H). HRMS calcd for C$_{17}$H$_{24}$N$_6$O, 329.2090 m/z (M+H)$^+$; observed 329.2085 m/z.

{3-[4-(3-Morpholin-4-yl-propylamino)-pyrimidin-2-ylamino]-phenyl}-methanol: $^1$H NMR (CDCl$_3$, 300 MHz) δ 1.72 (q, J=7.2 Hz, 2H), 2.30-2.41 (m, 6H), 3.30-3.38 (m, 2H), 3.58 (t, J=4.5 Hz, 4H), 4.45 (d, J=4.8 Hz, 2H), 5.10 (t, J=5.7 Hz, 1H), 5.92 (d, J=5.7 Hz, 1H), 6.83 (d, J=7.5 Hz, 1H), 7.16 (t, J=7.8 Hz, 2H), 7.62 (d, J=7.2 Hz, 1H), 7.80 (bs, 2H), 8.90 (s, 1H); HRMS calcd for C$_{18}$H$_{25}$N$_5$O$_2$, 344.2087 m/z (M+H)$^+$; observed 344.2084 m/z.

N$^2$-(3-Phenoxyphenyl)-N$^4$-(3-morpholin-4-yl-propyl)-pyrimidine-2,4-diamine. $^1$H NMR (DMSO-d6, 300 MHz): δ 1.62 (m, 2H), 2.31 (m, 6H), 2.52 (s, 2H), 3.56 (m, 4H), 5.92 (d, J=5.7 Hz, 1H), 6.51 (d, J=8.1 Hz, 1H), 6.99 (d, J=8.1 Hz, 2H), 7.10 (t, J=8.1 Hz, 1H), 7.21 (m, 2H), 7.37 (m, 2H), 7.80

(m, 1H), 9.10 (bs, 1H). HRMS calcd for $C_{23}H_{27}N_5O_2$, 406.2243 m/z $(M+H)^+$; observed 406.2252 m/z.

$N^2$-(3-Chlorophenyl)-$N^4$-[3-(4-methylpiperazin-1-yl)-propyl]-pyrimidine-2,4-diamine: $^1$H NMR (DMSO-$d_6$, 300 MHz): δ1.65-1.74 (m, 2H), 2.14 (s, 3H), 2.30-2.38 (m, 10H), 3.32-3.34 (m, 2H), 5.97 (d, J=5.7 Hz, 1H), 6.88 (d, J=7.8 Hz, 1H), 7.2 (t, J=8.1 Hz, 1H), 7.28 (br s, 1H), 7.69 (d, J=8.1 Hz, 1H), 7.80 (br s, 1H), 8.12 (br s, 1H), 9.19 (s, 1H). MS (ESI, pos. ion) m/z: 361 (M+1).

$N^2$-(4-(Benzyloxy)-3-chlorophenyl)-$N^4$-(3-pyrrolidin-1-yl-propyl)-pyrimidine-2,4-diamine. Yield 118 mg (46%) $^1$H NMR (CDCl$_3$, 300 MHz): δ 1.89 (m, 6H), 2.64 (m, 4H), 2.70 (t, J=6.6 Hz, 2H), 3.49 (m, 2H), 5.15 (s, 2H), 5.84 (d, J=5.7 Hz, 1H), 6.20 (s, 1H), 7.25 (m, 1H), 7.41 (m, 3H), 7.49 (m, 2H), 7.90 (m, 2H). HRMS calcd for $C_{24}H_{28}N_5OCl$, 438.2061 m/z $(M+H)^+$; observed 438.2077 m/z.

$N^2$-(3-Nitrophenyl)-$N^4$-(3-pyrrolidin-1-yl-propyl)-pyrimidine-2,4-diamine. $^1$H NMR (DMSO-d6, 300 MHz): δ 1.87 (m, 2H), 2.01 (m, 4H), 3.00 (m, 2H), 3.22 (m, 2H), 3.55 (m, 4H), 6.29 (d, J=6.6 Hz, 1H), 7.68 (t, J=8.4 Hz, 1H), 7.86 (d, J=7.2 Hz, 1H), 7.968 (m, 2H), 8.98 (s, 1H). HRMS calcd for $C_{17}H_{22}N_6O_2$, 343.1882 m/z $(M+H)^+$; observed 343.1895 m/z.

$N^2$-(3-Chlorophenyl)-$N^4$-(3-pyrrolidin-1-yl-propyl)-pyrimidine-2,4-diamine. $^1$H NMR (DMSO-d6, 300 MHz): δ 1.71 (m, 6H), 2.50 (m, 6H), 3.37 (m, 3H), 5.98 (d, J=5.7 Hz, 1H), 6.90 (d, J=9.0 Hz, 1H), 7.22 (t, J=8.1 Hz, 1H), 7.30 (s, 1H), 7.61 (d, J=8.1 Hz, 1H), 8.15 (s, 1H), 9.2 (s, 1H). HRMS calcd for $C_{17}H_{22}N_5Cl$, 332.1642 m/z $(M+H)^+$; observed 332.1655 m/z.

$N^2$-(3-Methylphenyl)-$N^4$-(3-pyrrolidin-1-yl-propyl)-pyrimidine-2,4-diamine: $^1$H NMR (DMSO-d6, 300 MHz) δ 1.78-2.06 (m, 6H), 2.35 (s, 3H), 2.85-3.00 (m, 2H), 3.10-3.18 (m, 2H), 3.40-3.55 (m, 4H), 6.27 (d, J=7.5 Hz, 1H), 7.02 (d, J=7.2 Hz, 1H), 7.32 (t, J=7.5 Hz, 1H), 7.37-7.42 (m, 2H), 7.84 (d, J=7.2 Hz, 1H), 9.34 (bs, 1H), 10.59 (s, 1H), 10.77 (bs, 1H); HRMS calcd for $C_{18}H_{27}N_5Cl$, 312.2188 m/z $(M+H)^+$; observed 312.2191 m/z.

$N^2$-[3-Methoxyphenyl]-$N^4$-(3-pyrrolidin-1-yl-propyl)-pyrimidine-2,4-diamine: $^1$H NMR (DMSO-d6, 300 MHz) δ 1.80-2.10 (m, 6H), 2.87-3.02 (m, 2H), 3.10-3.20 (m, 2H), 3.40-3.55 (m, 4H), 3.79 (s, 3H), 6.27 (d, J=7.2 Hz, 1H), 6.76 (d, J=8.1 Hz, 1H), 7 (d, J=8.4 Hz, 1H), 7.12 (d, J=8.4 Hz, 1H), 7.28-7.34 (m, 2H), 7.85 (d, J=7.2 Hz, 1H), 9.29 (bs, 1H), 10.60 (s, 1H), 10.78 (bs, 1H); HRMS calcd for $C_{18}H_{25}N_5O$, 328.2137 m/z $(M+H)^+$; observed 328.2149 m/z.

$N^2$-[3-Trifluoromethyl-phenyl]-$N^4$-(3-pyrrolidin-1-yl-propyl)-pyrimidine-2,4-diamine $^1$H NMR (DMSO-d6, 300 MHz) δ 1.77-2.04 (m, 6H), 2.83-3.00 (m, 2H), 3.03-3.20 (m, 2H), 3.31-3.70 (m, 4H), 6.32 (d, J=6.3 Hz, 1H), 7.50 (d, J=7.2 Hz, 1H), 7.65 (t, J=6.6 Hz, 1H), 7.8 (d, J=7.0 Hz, 1H), 7.89 (d, J=7.0 Hz, 1H), 8.15 (s, 1H), 9.40 (bs, 1H), 10.73 (bs, 1H), 11.00 (s, 1H); HRMS calcd for $C_{18}H_{24}N_5F_3Cl$, 366.1906 m/z $(M+H)^+$; observed 366.1906 m/z.

$N^2$-(3-Chlorophenyl)-$N^4$-[3-(1-methylpiperidin-4-yl)-methyl]-pyrimidine-2,4-diamine hydrochloride. $^1$H NMR (CD$_3$OD, 300 MHz): δ 1.53-1.58 (m, 2H), 2.04-2.09 (m, 3H), 2.87 (s, 3H), 2.98-3.05 (m, 2H), 3.46-3.59 (m, 4H), 6.31 (d, 1H, J=7.2 Hz), 7.27-7.48 (m, 3H), 7.25 (d, 1H, J=7.2 Hz), 7.83 (s, 1H). MS (ESI, pos. ion) m/z: 332 (M+1).

$N^2$-(3-Isopropylphenyl)-$N^4$-(3-morpholin-4-yl-propyl)-pyrimidine-2,4-diamine: $^1$H NMR (CDCl$_3$, 300 MHz): δ(ppm) 1.20 (d, J=2.1 Hz, 3H), 1.22 (d, J=2.1 Hz, 3H), 1.69-1.77 (m, 2H), 2.34-2.37 (m, 6H), 2.78-2.85 (m, 1H), 3.34 (m, 2H), 3.55-3.58 (m, 4H), 5.91 (d, J=6.0 Hz, 1H), 6.75 (d, J=7.8 Hz, 1H), 7.09-7.15 (m, 2H), 7.53 (bs, 1H), 7.77 (bs, 2H), 8.84 (s, 1H). HRMS calcd for $C_{20}H_{29}N_5O$, 356.2450, m/z $(M+H)^+$; observed 356.2463 m/z.

$N^2$-(3,5-Bis-trifluoromethyl-phenyl)-$N^4$-(3-morpholin-4-yl-propyl)-pyrimidine-2,4-diamine: $^1$H NMR (CD$_3$OD, 300 MHz) δ 2.12-2.22 (m, 2H), 3.13-3.27 (m, 4H), 3.49 (d, J=12.3 Hz, 2H), 3.65 (t, J=6.3 Hz, 2H), 3.83 (t, J=12.3 Hz, 2H), 4.07 (d, J=12.3 Hz, 2H), 6.43 (d, J=7.2 Hz, 1H), 7.83 (d, J=7.2 Hz, 1H), 7.85 (s, 1H), 8.32 (s, 2H); HRMS calcd for $C_{19}H_{21}F_6N_5O$, 450.1729 m/z $(M+H)^+$; observed 450.1743 m/z.

$N^4$-(3-Morpholin-4-yl-propyl)-$N^2$-(3-trifluoromethoxy-phenyl)-pyrimidine-2,4-diamine: MS (ESI, pos. ion) m/z: 398 (M+1).

$N^4$-(3-Morpholin-4-yl-propyl)-$N^2$-[3-(1,1,2,2-tetrafluoro-ethoxy)-phenyl]-pyrimidine-2,4-diamine: MS (ESI, pos. ion) m/z: 430 (M+1).

Further compounds which are encompassed within the first aspect of Category I of the present invention but which are not fully exemplified include:

$N^2$-(3-Chlorophenyl)-$N^4$-(3-pyrrolidin-1-yl-propyl)-pyrimidine-2,4-diamine;

$N^2$-(3-Chlorophenyl)-$N^4$-(3-pyrrolin-1-yl-propyl)-pyrimidine-2,4-diamine;

$N^2$-(3-Chlorophenyl)-$N^4$-(3-imidazolidin-1-yl-propyl)-pyrimidine-2,4-diamine;

$N^2$-(3-Chlorophenyl)-$N^4$-(3-imidazolin-1-yl-propyl)-pyrimidine-2,4-diamine;

$N^2$-(3-Chlorophenyl)-$N^4$-(3-pyrazolidin-1-yl-propyl)-pyrimidine-2,4-diamine;

$N^2$-(3-Fluorophenyl)-$N^4$-(3-pyrrolidin-1-yl-propyl)-pyrimidine-2,4-diamine;

$N^2$-(3-Fluorophenyl)-$N^4$-(3-pyrrolin-1-yl-propyl)-pyrimidine-2,4-diamine;

$N^2$-(3-Fluorophenyl)-$N^4$-(3-imidazolidin-1-yl-propyl)-pyrimidine-2,4-diamine;

$N^2$-(3-Fluorophenyl)-$N^4$-(3-imidazolin-1-yl-propyl)-pyrimidine-2,4-diamine;

$N^2$-(3-Fluorophenyl)-$N^4$-(3-piperidin-1-yl-propyl)-pyrimidine-2,4-diamine;

$N^2$-(3-Fluorophenyl)-$N^4$-(3-piperazin-1-yl-propyl)-pyrimidine-2,4-diamine;

$N^2$-(3-Fluorophenyl)-$N^4$-(3-pyrazolidin-1-yl-propyl)-pyrimidine-2,4-diamine;

$N^2$-(3-Methylphenyl)-$N^4$-(3-pyrrolidin-1-yl-propyl)-pyrimidine-2,4-diamine;

$N^2$-(3-Methylphenyl)-$N^4$-(3-pyrrolin-1-yl-propyl)-pyrimidine-2,4-diamine;

$N^2$-(3-Methylphenyl)-$N^4$-(3-imidazolidin-1-yl-propyl)-pyrimidine-2,4-diamine;

$N^2$-(3-Methylphenyl)-$N^4$-(3-imidazolin-1-yl-propyl)-pyrimidine-2,4-diamine;

$N^2$-(3-Methylphenyl)-$N^4$-(3-pyrazolidin-1-yl-propyl)-pyrimidine-2,4-diamine;

$N^2$-(3-Methylphenyl)-$N^4$-(3-piperidin-1-yl-propyl)-pyrimidine-2,4-diamine;

$N^2$-(3-Methylphenyl)-$N^4$-(3-piperazin-1-yl-propyl)-pyrimidine-2,4-diamine;

$N^2$-(3-Methoxyphenyl)-$N^4$-(3-pyrrolidin-1-yl-propyl)-pyrimidine-2,4-diamine;

$N^2$-(3-Methoxyphenyl)-$N^4$-(3-pyrrolin-1-yl-propyl)-pyrimidine-2,4-diamine;

$N^2$-(3-Methoxyphenyl)-$N^4$-(3-imidazolidin-1-yl-propyl)-pyrimidine-2,4-diamine;

$N^2$-(3-Methoxyphenyl)-$N^4$-(3-imidazolin-1-yl-propyl)-pyrimidine-2,4-diamine;

$N^2$-(3-Methoxyphenyl)-$N^4$-(3-pyrazolidin-1-yl-propyl)-pyrimidine-2,4-diamine;

N²-(3-Methoxyphenyl)-N⁴-(3-piperidin-1-yl-propyl)-pyrimidine-2,4-diamine;
N²-(3-Methoxyphenyl)-N⁴-(3-piperazin-1-yl-propyl)-pyrimidine-2,4-diamine;
N²-(3-Trifluoromethylphenyl)-N⁴-(3-pyrrolidin-1-yl-propyl)-pyrimidine-2,4-diamine;
N²-(3-Trifluoromethylphenyl)-N⁴-(3-pyrrolin-1-yl-propyl)-pyrimidine-2,4-diamine;
N²-(3-Trifluoromethylphenyl)-N⁴-(3-imidazolidin-1-yl-propyl)-pyrimidine-2,4-diamine;
N²-(3-Trifluoromethylphenyl)-N⁴-(3-imidazolin-1-yl-propyl)-pyrimidine-2,4-diamine;
N²-(3-Trifluoromethylphenyl)-N⁴-(3-pyrazolidin-1-yl-propyl)-pyrimidine-2,4-diamine;
N²-(3-Trifluoromethylphenyl)-N⁴-(3-piperidin-1-yl-propyl)-pyrimidine-2,4-diamine; and
N²-(3-Trifluoromethylphenyl)-N⁴-(3-piperazin-1-yl-propyl)-pyrimidine-2,4-diamine.

The compounds which comprise the second aspect of Category I of the present invention are 2,4-di-aminopyrimidines having the formula:

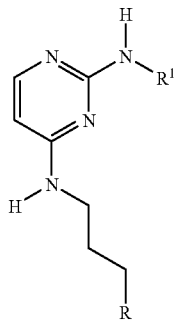

wherein $R^1$ phenyl units are substituted by one or more $R^5$ units chosen from:

x) substituted or unsubstituted $C_3$-$C_9$ heteroaryl units;

which are further exemplified herein below in Table II.

TABLE II

| No | R | R¹ |
|---|---|---|
| 121 | pyrrolidin-1-yl | 2-(pyridin-2-yl)phenyl |
| 122 | pyrrolin-1-yl | 2-(pyridin-2-yl)phenyl |
| 123 | imidazolin-1-yl | 2-(pyridin-2-yl)phenyl |
| 124 | imidazolin-1-yl | 2-(pyridin-2-yl)phenyl |
| 125 | pyrazolidin-1-yl | 2-(pyridin-2-yl)phenyl |
| 126 | pyrazolin-1-yl | 2-(pyridin-2-yl)phenyl |
| 127 | piperidin-1-yl | 2-(pyridin-2-yl)phenyl |
| 128 | piperazin-1-yl | 2-(pyridin-2-yl)phenyl |
| 129 | 4-methylpiperazin-1-yl | 2-(pyridin-2-yl)phenyl |
| 130 | morpholin-4-yl | 2-(pyridin-2-yl)phenyl |
| 131 | pyrrolidin-1-yl | 2-(pyridin-3-yl)phenyl |
| 132 | pyrrolin-1-yl | 2-(pyridin-3-yl)phenyl |
| 133 | imidazolidin-1-yl | 2-(pyridin-3-yl)phenyl |
| 134 | imidazolin-1-yl | 2-(pyridin-3-yl)phenyl |
| 135 | pyrazolidin-1-yl | 2-(pyridin-3-yl)phenyl |
| 136 | pyrazolin-1-yl | 2-(pyridin-3-yl)phenyl |
| 137 | piperidin-1-yl | 2-(pyridin-3-yl)phenyl |
| 138 | piperazin-1-yl | 2-(pyridin-3-yl)phenyl |
| 139 | 4-methylpiperazin-1-yl | 2-(pyridin-3-yl)phenyl |
| 140 | morpholin-4-yl | 2-(pyridin-4-yl)phenyl |
| 141 | pyrrolidin-1-yl | 2-(pyridin-4-yl)phenyl |
| 142 | pyrrolin-1-yl | 2-(pyridin-4-yl)phenyl |
| 143 | imidazolidin-1-yl | 2-(pyridin-4-yl)phenyl |
| 144 | imidazolin-1-yl | 2-(pyridin-4-yl)phenyl |
| 145 | pyrazolidin-1-yl | 2-(pyridin-4-yl)phenyl |
| 146 | pyrazolin-1-yl | 2-(pyridin-4-yl)phenyl |
| 147 | piperidin-1-yl | 2-(pyridin-4-yl)phenyl |
| 148 | piperazin-1-yl | 2-(pyridin-4-yl)phenyl |
| 149 | 4-methylpiperazin-1-yl | 2-(pyridin-4-yl)phenyl |
| 150 | morpholin-4-yl | 2-(pyridin-4-yl)phenyl |
| 151 | pyrrolidin-1-yl | 3-(pyridin-2-yl)phenyl |
| 152 | pyrrolin-1-yl | 3-(pyridin-2-yl)phenyl |
| 153 | imidazolidin-1-yl | 3-(pyridin-2-yl)phenyl |
| 154 | imidazolin-1-yl | 3-(pyridin-2-yl)phenyl |
| 155 | pyrazolidin-1-yl | 3-(pyridin-2-yl)phenyl |
| 156 | pyrazolin-1-yl | 3-(pyridin-2-yl)phenyl |
| 157 | piperidin-1-yl | 3-(pyridin-2-yl)phenyl |
| 158 | piperazin-1-yl | 3-(pyridin-2-yl)phenyl |
| 159 | 4-methylpiperazin-1-yl | 3-(pyridin-2-yl)phenyl |
| 160 | morpholin-4-yl | 3-(pyridin-2-yl)phenyl |
| 161 | pyrrolidin-1-yl | 3-(pyridin-3-yl)phenyl |
| 162 | pyrrolin-1-yl | 3-(pyridin-3-yl)phenyl |
| 163 | imidazolidin-1-yl | 3-(pyridin-3-yl)phenyl |
| 164 | imidazolin-1-yl | 3-(pyridin-3-yl)phenyl |
| 165 | pyrazolidin-1-yl | 3-(pyridin-3-yl)phenyl |
| 166 | pyrazolin-1-yl | 3-(pyridin-3-yl)phenyl |
| 167 | piperidin-1-yl | 3-(pyridin-3-yl)phenyl |
| 168 | piperazin-1-yl | 3-(pyridin-3-yl)phenyl |
| 169 | 4-methylpiperazin-1-yl | 3-(pyridin-3-yl)phenyl |
| 170 | morpholin-4-yl | 3-(pyridin-4-yl)phenyl |
| 171 | pyrrolidin-1-yl | 3-(pyridin-4-yl)phenyl |
| 172 | pyrrolin-1-yl | 3-(pyridin-4-yl)phenyl |
| 173 | imidazolidin-1-yl | 3-(pyridin-4-yl)phenyl |
| 174 | imidazolin-1-yl | 3-(pyridin-4-yl)phenyl |
| 175 | pyrazolidin-1-yl | 3-(pyridin-4-yl)phenyl |
| 176 | pyrazolin-1-yl | 3-(pyridin-4-yl)phenyl |
| 177 | piperidin-1-yl | 3-(pyridin-4-yl)phenyl |
| 178 | piperazin-1-yl | 3-(pyridin-4-yl)phenyl |
| 179 | 4-methylpiperazin-1-yl | 3-(pyridin-4-yl)phenyl |
| 180 | morpholin-4-yl | 3-(pyridin-4-yl)phenyl |
| 181 | pyrrolidin-1-yl | 4-(pyridin-2-yl)phenyl |
| 182 | pyrrolin-1-yl | 4-(pyridin-2-yl)phenyl |
| 183 | imidazolidin-1-yl | 4-(pyridin-2-yl)phenyl |
| 184 | imidazolin-1-yl | 4-(pyridin-2-yl)phenyl |
| 185 | pyrazolidin-1-yl | 4-(pyridin-2-yl)phenyl |
| 186 | pyrazolin-1-yl | 4-(pyridin-2-yl)phenyl |
| 187 | piperidin-1-yl | 4-(pyridin-2-yl)phenyl |
| 188 | piperazin-1-yl | 4-(pyridin-2-yl)phenyl |
| 189 | 4-methylpiperazin-1-yl | 4-(pyridin-2-yl)phenyl |
| 190 | morpholin-4-yl | 4-(pyridin-2-yl)phenyl |
| 191 | pyrrolidin-1-yl | 4-(pyridin-3-yl)phenyl |
| 192 | pyrrolin-1-yl | 4-(pyridin-3-yl)phenyl |
| 193 | imidazolidin-1-yl | 4-(pyridin-3-yl)phenyl |
| 194 | imidazolin-1-yl | 4-(pyridin-3-yl)phenyl |
| 195 | pyrazolidin-1-yl | 4-(pyridin-3-yl)phenyl |
| 196 | pyrazolin-1-yl | 4-(pyridin-3-yl)phenyl |
| 197 | piperidin-1-yl | 4-(pyridin-3-yl)phenyl |
| 198 | piperazin-1-yl | 4-(pyridin-3-yl)phenyl |
| 199 | 4-methylpiperazin-1-yl | 4-(pyridin-3-yl)phenyl |
| 200 | morpholin-4-yl | 4-(pyridin-4-yl)phenyl |
| 201 | pyrrolidin-1-yl | 4-(pyridin-4-yl)phenyl |
| 202 | pyrrolin-1-yl | 4-(pyridin-4-yl)phenyl |
| 203 | imidazolidin-1-yl | 4-(pyridin-4-yl)phenyl |
| 204 | imidazolin-1-yl | 4-(pyridin-4-yl)phenyl |
| 205 | pyrazolidin-1-yl | 4-(pyridin-4-yl)phenyl |
| 206 | pyrazolin-1-yl | 4-(pyridin-4-yl)phenyl |
| 207 | piperidin-1-yl | 4-(pyridin-4-yl)phenyl |
| 208 | piperazin-1-yl | 4-(pyridin-4-yl)phenyl |
| 209 | 4-methylpiperazin-1-yl | 4-(pyridin-4-yl)phenyl |
| 210 | morpholin-4-yl | 4-(pyridin-4-yl)phenyl |
| 211 | pyrrolidin-1-yl | 3-(pyrimidin-2-yl)phenyl |
| 212 | pyrrolin-1-yl | 3-(pyrimidin-2-yl)phenyl |
| 213 | imidazolidin-1-yl | 3-(pyrimidin-2-yl)phenyl |
| 214 | imidazolin-1-yl | 3-(pyrimidin-2-yl)phenyl |
| 215 | pyrazolidin-1-yl | 3-(pyrimidin-2-yl)phenyl |
| 216 | pyrazolin-1-yl | 3-(pyrimidin-2-yl)phenyl |
| 217 | piperidin-1-yl | 3-(pyrimidin-2-yl)phenyl |
| 218 | piperazin-1-yl | 3-(pyrimidin-2-yl)phenyl |
| 219 | 4-methylpiperazin-1-yl | 3-(pyrimidin-2-yl)phenyl |
| 220 | morpholin-4-yl | 3-(pyrimidin-2-yl)phenyl |
| 221 | pyrrolidin-1-yl | 3-(pyrimidin-3-yl)phenyl |
| 222 | pyrrolin-1-yl | 3-(pyrimidin-3-yl)phenyl |
| 223 | imidazolidin-1-yl | 3-(pyrimidin-3-yl)phenyl |
| 224 | imidazolin-1-yl | 3-(pyrimidin-3-yl)phenyl |

TABLE II-continued

| No  | R                    | R¹                       |
|-----|----------------------|--------------------------|
| 225 | pyrazolidin-1-yl     | 3-(pyrimidin-3-yl)phenyl |
| 226 | pyrazolin-1-yl       | 3-(pyrimidin-3-yl)phenyl |
| 227 | piperidin-1-yl       | 3-(pyrimidin-3-yl)phenyl |
| 228 | piperazin-1-yl       | 3-(pyrimidin-3-yl)phenyl |
| 229 | 4-methylpiperazin-1-yl | 3-(pyrimidin-3-yl)phenyl |
| 230 | morpholin-4-yl       | 3-(pyrimidin-4-yl)phenyl |
| 231 | pyrrolidin-1-yl      | 3-(pyrimidin-4-yl)phenyl |
| 232 | pyrrolin-1-yl        | 3-(pyrimidin-4-yl)phenyl |
| 233 | imidazolidin-1-yl    | 3-(pyrimidin-4-yl)phenyl |
| 234 | imidazolin-1-yl      | 3-(pyrimidin-4-yl)phenyl |
| 235 | pyrazolidin-1-yl     | 3-(pyrimidin-4-yl)phenyl |
| 236 | pyrazolin-1-yl       | 3-(pyrimidin-4-yl)phenyl |
| 237 | piperidin-1-yl       | 3-(pyrimidin-4-yl)phenyl |
| 238 | piperazin-1-yl       | 3-(pyrimidin-4-yl)phenyl |
| 239 | 4-methylpiperazin-1-yl | 3-(pyrimidin-4-yl)phenyl |
| 240 | morpholin-4-yl       | 3-(pyrimidin-4-yl)phenyl |

The compounds which comprise the second aspect of Category I of the present invention can be prepared by the procedure outlined herein below in Scheme II and Example 2.

Scheme II

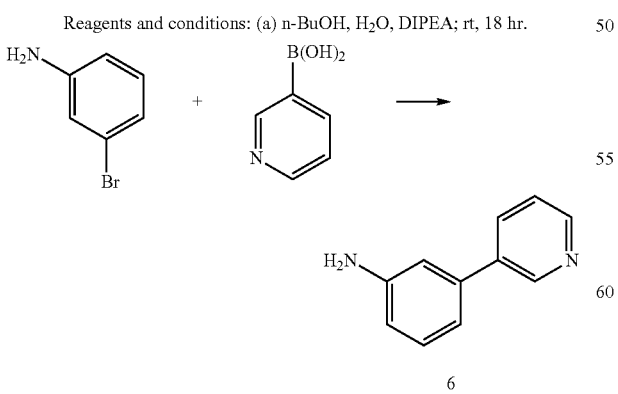

Reagents and conditions: (a) n-BuOH, H₂O, DIPEA; rt, 18 hr.

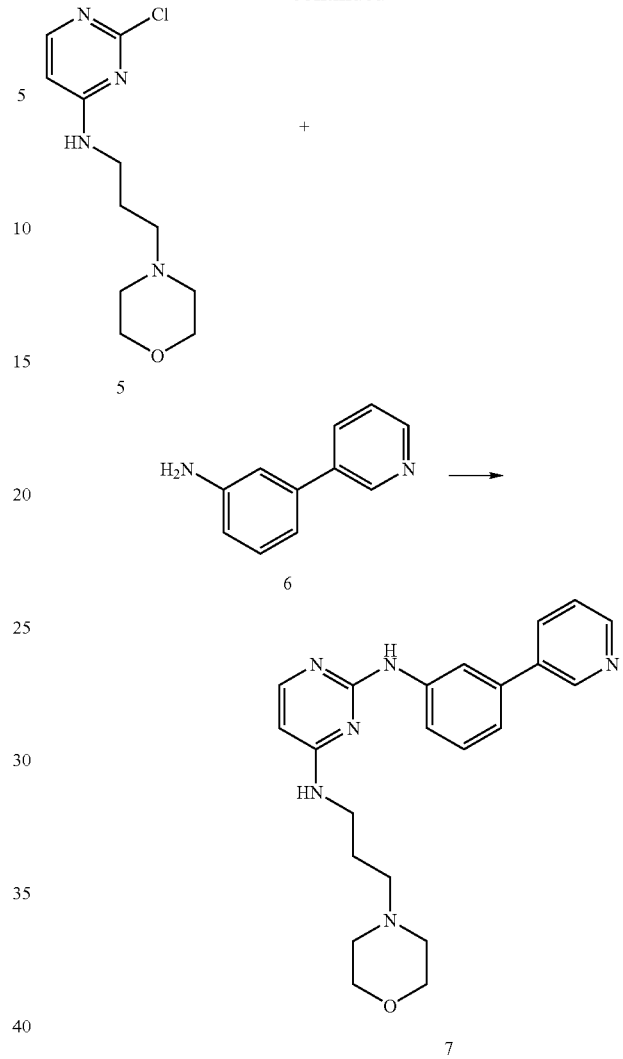

Reagents and conditions (b): NaCO₃, Pd(PPh₃)₄, EtOH/toluene/H₂O; 80° C., 18 hr.

Reagents and conditions (c): EtOH/H₂O, HCl; 80° C., 18 hr.

Example 2

$N^2$-[3-(Pyridin-3-yl)-phenyl]-$N^4$-(3-morpholin-4-yl-propyl)-pyrimidine-2,4-diamine (7)

Preparation of 2-chloro-N-(3-morpholinopropyl)pyrimidin-4-amine (5): To 2,4-dichloropyrimidine (5.0 g, 33.5 mmol), diisoproylethylamine (5.85 ml, 33.5 mmol) in 50 ml of a 1:1 mixture of n-butanol and water is added 3-morpholinopropan-1-amine (4.90 ml, 33.5 mmol). The resulting mixture was stirred for 18 hours at room temperature. The mixture is then concentrated in vacuo, diluted with 30 mL water and extracted with EtOAc (3×50 ml). Combined organic layers are washed with saturated NaHCO₃ (2×20 ml) and saturated NaCl (2×20 ml), then dried over magnesium sulfate. The residue is purified over silica (25% EtOAc in Hexanes) to afford 4.5 g (51% yield) of the desired product. $^1$H NMR (CDCl₃, 300 MHz): δ(ppm) 1.83 (q, J=2.0 Hz, 2H), 2.54 (m, 6H), 3.53 (bs, 2H), 3.79 (t, J=4.7 Hz, 4H), 6.24 (d, J=5.67 Hz, 1H), 6.92 (bs, 1H), 7.99 (bs, 1H). MS (ESI, pos. ion) m/z: 257 (M+1).

Preparation of 3-(pyridin-3-yl)benzenamine (6): To 3-bromoaniline (513.1 mg, 2.983 mmol) was added ethanol/toluene (1:1, 20 mL), 3-pyridinylboronic acid (397.3 mg, 3.232 mmol), sodium carbonate (1.85 g, 17.45 mmol) in 9 mL water, and tetrakis(triphenylphosphine)palladium (504.3 mg, 0.439 mmol). The resulting mixture is heated to 80° C. and stirred for 16 h. The reaction mixture is cooled, diluted with 10 mL of water and extracted with EtOAc (3×25 ml). The organics were combined and, washed with 10 mL of water and saturated aqueous NaCl (2×10 mL), then dried over magnesium sulfate and concentrated in vacuo to a brown oil. The oil is purified over silica (0-5% MeOH in $CH_2Cl_2$) to afford 345 mg (68% yield) of the desired compound. MS (ESI, pos. ion) m/z: 171 (M+1).

Preparation of $N^2$-(3-(pyridin-3-yl)-phenyl)-$N^4$-(3-morpholin-4-yl-propyl)pyrimidine-2,4-diamine(7): To 2-chloro-N-(3-morpholinopropyl)pyrimidin-4-amine, 5, (105.7 mg, 0.4117 mmol) in 3 mL of EtOH/water (1:1) is added 3-(pyridin-3-yl)benzenamine (84.0 mg, 0.4941 mmol) and 2 drops concentrated HCl. The resulting mixture is heated to 80° C. with stirring for 3 days. The reaction mixture is cooled to room temperature and concentrated in vacuo. The product was diluted with 5 mL of aqueous saturated sodium bicarbonate solution and extracted with EtOAc (3×10 ml). The combined organics are washed with 20 ml water and saturated aqueous NaCl (2×10 ml), then dried over magnesium sulfate and concentrated in vacuo. The residue is purified over silica (5-8% MeOH in $CH_2Cl_2$) to afford 61 mg (38% yield) of the desired compound. $^1H$ NMR (DMSO-$d_6$, 300 MHz): δ 1.63-1.77 (m, 2H), 2.20-2.40 (m, 6H), 3.30-3.47 (m, 2H), 3.54 (t, J=4.2 Hz, 4H), 5.96 (d, J=5.4 Hz, 1H), 7.12-7.28 (m, 2H), 7.36 (t, J=7.8 Hz, 1H), 7.50 (dd, J=4.8, 7.8 Hz, 1H), 7.78 (bs, 1H), 7.82 (d, J=7.8 Hz, 1H), 8.01 (d, J=7.8 Hz, 1H), 8.29 (bs, 1H), 8.58 (d, J=4.8 Hz, 1H), 8.85 (s, 1H), 9.10 (s, 1H). HRMS calcd for $C_{22}H_{26}N_6O$, 391.2246 m/z $(M+H)^+$; observed 391.2242 m/z.

The following are non-limiting examples of compounds which comprise the second aspect of Category I of the present invention, the characterization of which will assist the formulator in establishing the chemical formulae of compounds which are not specifically exemplified herein. Alternatively, these compounds may also be synthesized by the synthetic route or methods described earlier in Scheme I.

$N^2$-[3-(Benzo[d]thiazol-2-yl)-phenyl]-$N^4$-(3-morpholin-4-yl-propyl)-pyrimidine-2,4-diamine. $^1H$ NMR (DMSO-d6, 300 MHz): δ 1.71-1.76 (m, 2H), 2.25-2.34 (m, 6H), 2.52 (s, 2H), 3.51 (m, 4H), 6.00 (d, J=6.0 Hz, 1H), 7.29 (bs, 1H), 7.45 (m, 2H), 7.54 (m, 2H), 7.84 (m, 1H), 8.06 (d, J=8.1 Hz, 1H), 8.15 (d, J=7.5 Hz, 1H), 8.86 (bs, 1H), 9.28 (s, 1H). HRMS calcd for $C_{24}H_{26}N_6OS$, 447.1967 m/z $(M+H)^+$; observed 447.1976 m/z.

$N^2$-[3-(1H-Indol-2-yl)-phenyl]-$N^4$-(3-morpholin-4-yl-propyl)-pyrimidine-2,4-diamine: HRMS calcd for $C_{25}H_{28}N_6O$, 429.2397 m/z $(M+H)^+$; observed 429.2395 m/z.

$N^2$-[3-(1H-Indol-4-yl)-phenyl]-$N^4$-(3-morpholin-4-yl-propyl)-pyrimidine-2,4-diamine: HRMS calcd for $C_{25}H_{29}N_6O$, 429.2397 m/z $(M+H)^+$; observed 429.2406 m/z.

$N^2$-[3-(Pyridin-4-yl)-phenyl]-$N^4$-(3-morpholin-4-yl-propyl)-pyrimidine-2,4-diamine: HRMS calcd for $C_{22}H_{27}N_6O$, 391.2246 m/z $(M+H)^+$; observed 391.2255 m/z.

$N^2$-[3-(1H-Indol-6-yl)-phenyl]-$N^4$-(3-morpholin-4-yl-propyl)-pyrimidine-2,4-diamine: HRMS calcd for $C_{25}H_{29}N_6O$, 429.2403 m/z $(M+H)^+$; observed 429.2412 m/z.

Further compounds which are encompassed within the second aspect of Category II of the present invention but which are not fully exemplified include:

$N^2$-[3-(Pyridin-2-yl)-phenyl]-$N^4$-(3-morpholin-4-yl-propyl)-pyrimidine-2,4-diamine;

$N^2$-[3-(1H-Indol-3-yl)-phenyl]-$N^4$-(3-morpholin-4-yl-propyl)-pyrimidine-2,4-diamine;

$N^2$-[3-(1H-Indol-2-yl)-phenyl]-$N^4$-(3-pyrrolidin-1-yl-propyl)-pyrimidine-2,4-diamine;

$N^2$-[3-(1H-Indol-3-yl)-phenyl]-$N^4$-(3-pyrrolidin-1-yl-propyl)-pyrimidine-2,4-diamine;

$N^2$-[3-(Benzo[d]thiazol-2-yl)-phenyl]-$N^4$-(3-pyrrolidin-1-yl-propyl)-pyrimidine-2,4-diamine;

$N^2$-[3-(Pyridin-2-yl)-phenyl]-$N^4$-(3-pyrrolin-1-yl-propyl)-pyrimidine-2,4-diamine;

$N^2$-[3-(Pyridin-4-yl)-phenyl]-$N^4$-(3-pyrrolin-1-yl-propyl)-pyrimidine-2,4-diamine;

$N^2$-[3-(1H-Indol-2-yl)-phenyl]-$N^4$-(3-pyrrolin-1-yl-propyl)-pyrimidine-2,4-diamine;

$N^2$-[3-(1H-Indol-3-yl)-phenyl]-$N^4$-(3-pyrrolin-1-yl-propyl)-pyrimidine-2,4-diamine;

$N^2$-[3-(Benzo[d]thiazol-2-yl)-phenyl]-$N^4$-(3-pyrrolin-1-yl-propyl)-pyrimidine-2,4-diamine;

$N^2$-[3-(Pyridin-2-yl)-phenyl]-$N^4$-(3-imidazolidin-1-yl-propyl)-pyrimidine-2,4-diamine;

$N^2$-[3-(Pyridin-4-yl)-phenyl]-$N^4$-(3-imidazolidin-1-yl-propyl)-pyrimidine-2,4-diamine;

$N^2$-[3-(1H-Indol-2-yl)-phenyl]-$N^4$-(3-imidazolidin-1-yl-propyl)-pyrimidine-2,4-diamine;

$N^2$-[3-(1H-Indol-3-yl)-phenyl]-$N^4$-(3-imidazolidin-1-yl-propyl)-pyrimidine-2,4-diamine;

$N^2$-[3-(Benzo[d]thiazol-2-yl)-phenyl]-$N^4$-(3-imidazolidin-1-yl-propyl)-pyrimidine-2,4-diamine;

$N^2$-[3-(Pyridin-2-yl)-phenyl]-$N^4$-(3-imidazolin-1-yl-propyl)-pyrimidine-2,4-diamine;

$N^2$-[3-(Pyridin-4-yl)-phenyl]-$N^4$-(3-imidazolin-1-yl-propyl)-pyrimidine-2,4-diamine;

$N^2$-[3-(1H-Indol-2-yl)-phenyl]-$N^4$-(3-imidazolin-1-yl-propyl)-pyrimidine-2,4-diamine;

$N^2$-[3-(1H-Indol-3-yl)-phenyl]-$N^4$-(3-imidazolin-1-yl-propyl)-pyrimidine-2,4-diamine;

$N^2$-[3-(Benzo[d]thiazol-2-yl)-phenyl]-$N^4$-(3-imidazolin-1-yl-propyl)-pyrimidine-2,4-diamine;

$N^2$-[3-(Pyridin-2-yl)-phenyl]-$N^4$-(3-pyrazolidin-1-yl-propyl)-pyrimidine-2,4-diamine;

$N^2$-[3-(Pyridin-4-yl)-phenyl]-$N^4$-(3-pyrazolidin-1-yl-propyl)-pyrimidine-2,4-diamine;

$N^2$-[3-(1H-Indol-2-yl)-phenyl]-$N^4$-(3-pyrazolidin-1-yl-propyl)-pyrimidine-2,4-diamine;

$N^2$-[3-(1H-Indol-3-yl)-phenyl]-$N^4$-(3-pyrazolidin-1-yl-propyl)-pyrimidine-2,4-diamine;

$N^2$-[3-(Benzo[d]thiazol-2-yl)-phenyl]-$N^4$-(3-pyrazolidin-1-yl-propyl)-pyrimidine-2,4-diamine;

$N^2$-[3-(Pyridin-2-yl)-phenyl]-$N^4$-(3-pyrazolin-1-yl-propyl)-pyrimidine-2,4-diamine;

$N^2$-[3-(Pyridin-4-yl)-phenyl]-$N^4$-(3-pyrazolin-1-yl-propyl)-pyrimidine-2,4-diamine;

$N^2$-[3-(1H-Indol-2-yl)-phenyl]-$N^4$-(3-pyrazolin-1-yl-propyl)-pyrimidine-2,4-diamine;

$N^2$-[3-(1H-Indol-3-yl)-phenyl]-$N^4$-(3-pyrazolin-1-yl-propyl)-pyrimidine-2,4-diamine;

$N^2$-[3-(Benzo[d]thiazol-2-yl)-phenyl]-$N^4$-(3-pyrazolin-1-yl-propyl)-pyrimidine-2,4-diamine;

$N^2$-[3-(Pyridin-2-yl)-phenyl]-$N^4$-(3-piperidin-1-yl-propyl)-pyrimidine-2,4-diamine;

$N^2$-[3-(Pyridin-4-yl)-phenyl]-$N^4$-(3-piperidin-1-yl-propyl)-pyrimidine-2,4-diamine;

$N^2$-[3-(1H-Indol-2-yl)-phenyl]-$N^4$-(3-piperidin-1-yl-propyl)-pyrimidine-2,4-diamine;

$N^2$-[3-(1H-Indol-3-yl)-phenyl]-$N^4$-(3-piperidin-1-yl-propyl)-pyrimidine-2,4-diamine;

N²-[3-(Benzo[d]thiazol-2-yl)-phenyl]-N⁴-(3-piperidin-1-yl-propyl)-pyrimidine-2,4-diamine;
N²-[3-(Pyridin-2-yl)-phenyl]-N⁴-(3-piperazin-1-yl-propyl)-pyrimidine-2,4-diamine;
N²-[3-(Pyridin-4-yl)-phenyl]-N⁴-(3-piperazin-1-yl-propyl)-pyrimidine-2,4-diamine;
N²-[3-(1H-Indol-2-yl)-phenyl]-N⁴-(3-piperazin-1-yl-propyl)-pyrimidine-2,4-diamine;
N²-[3-(1H-Indol-3-yl)-phenyl]-N⁴-(3-piperazin-1-yl-propyl)-pyrimidine-2,4-diamine;
N²-[3-(Benzo[d]thiazol-2-yl)-phenyl]-N⁴-(3-piperazin-1-yl-propyl)-pyrimidine-2,4-diamine;
N²-[3-(Pyridin-2-yl)-phenyl]-N⁴-[3-(4-methylpiperazin-1-yl)-propyl]-pyrimidine-2,4-diamine;
N²-[3-(Pyridin-4-yl)-phenyl]-N⁴-[3-(4-methylpiperazin-1-yl)-propyl]-pyrimidine-2,4-diamine;
N²-[3-(1H-Indol-2-yl)-phenyl]-N⁴-[3-(4-methylpiperazin-1-yl)-propyl]-pyrimidine-2,4-diamine;
N²-[3-(1H-Indol-3-yl)-phenyl]-N⁴-[3-(4-methylpiperazin-1-yl)-propyl]-pyrimidine-2,4-diamine; and
N²-[3-(Benzo[d]thiazol-2-yl)-phenyl]-N⁴-[3-(4-methylpiperazin-1-yl)-propyl]-pyrimidine-2,4-diamine.

The third aspect of Category I of the present invention are 2,4-di-aminopyrimidines having the formula:

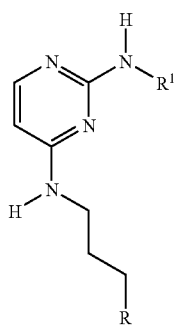

wherein R¹ phenyl units are substituted by one or more R⁵ units chosen from:
viii) substituted or unsubstituted phenyl;
which are further exemplified herein below in Table III.

TABLE III

| No | R | R¹ |
|---|---|---|
| 241 | pyrrolidin-1-yl | biphenyl-3-yl |
| 242 | pyrrolin-1-yl | biphenyl-3-yl |
| 243 | imidazolidin-1-yl | biphenyl-3-yl |
| 244 | imidazolin-1-yl | biphenyl-3-yl |
| 245 | pyrazolidin-1-yl | biphenyl-3-yl |
| 246 | pyrazolin-1-yl | biphenyl-3-yl |
| 247 | piperidin-1-yl | biphenyl-3-yl |
| 248 | piperazin-1-yl | biphenyl-3-yl |
| 249 | 4-methylpiperazin-1-yl | biphenyl-3-yl |
| 250 | morpholin-4-yl | biphenyl-3-yl |
| 251 | pyrrolidin-1-yl | biphenyl-4-yl |
| 252 | pyrrolin-1-yl | biphenyl-4-yl |
| 253 | imidazolidin-1-yl | biphenyl-4-yl |
| 254 | imidazolin-1-yl | biphenyl-4-yl |
| 255 | pyrazolidin-1-yl | biphenyl-4-yl |
| 256 | pyrazolin-1-yl | biphenyl-4-yl |
| 257 | piperidin-1-yl | biphenyl-4-yl |
| 258 | piperazin-1-yl | biphenyl-4-yl |
| 259 | 4-methylpiperazin-1-yl | biphenyl-4-yl |
| 260 | morpholin-4-yl | biphenyl-4-yl |
| 261 | pyrrolidin-1-yl | 4'-fluoro-biphenyl-3-yl |
| 262 | pyrrolin-1-yl | 4'-fluoro-biphenyl-3-yl |

TABLE III-continued

| No | R | R¹ |
|---|---|---|
| 263 | imidazolidin-1-yl | 4'-fluoro-biphenyl-3-yl |
| 264 | imidazolin-1-yl | 4'-fluoro-biphenyl-3-yl |
| 265 | pyrazolidin-1-yl | 4'-fluoro-biphenyl-3-yl |
| 266 | pyrazolin-1-yl | 4'-fluoro-biphenyl-3-yl |
| 267 | piperidin-1-yl | 4'-fluoro-biphenyl-3-yl |
| 268 | piperazin-1-yl | 4'-fluoro-biphenyl-3-yl |
| 269 | 4-methylpiperazin-1-yl | 4'-fluoro-biphenyl-3-yl |
| 270 | morpholin-4-yl | 4'-fluoro-biphenyl-3-yl |
| 271 | pyrrolidin-1-yl | 4'-chloro-biphenyl-3-yl |
| 272 | pyrrolin-1-yl | 4'-chloro-biphenyl-3-yl |
| 273 | imidazolidin-1-yl | 4'-chloro-biphenyl-3-yl |
| 274 | imidazolin-1-yl | 4'-chloro-biphenyl-3-yl |
| 275 | pyrazolidin-1-yl | 4'-chloro-biphenyl-3-yl |
| 276 | pyrazolin-1-yl | 4'-chloro-biphenyl-3-yl |
| 277 | piperidin-1-yl | 4'-chloro-biphenyl-3-yl |
| 278 | piperazin-1-yl | 4'-chloro-biphenyl-3-yl |
| 279 | 4-methylpiperazin-1-yl | 4'-chloro-biphenyl-3-yl |
| 280 | morpholin-4-yl | 4'-chloro-biphenyl-3-yl |

Scheme III

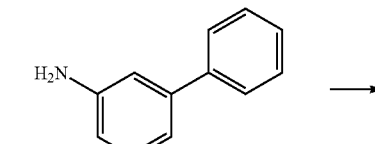

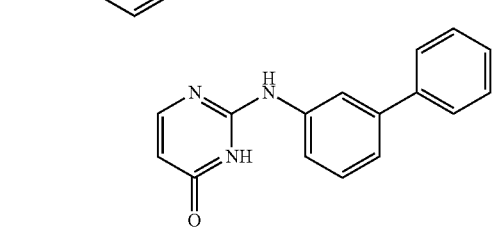

Reagents and conditions: (a) diglyme, reflux, 18 h.

8

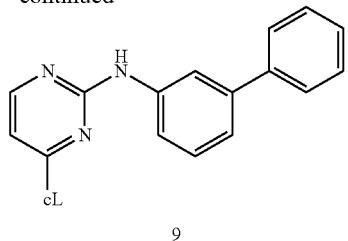

Reagents and conditions (b): POCl₃, N,N-dimethylaniline, reflux, 15 min.

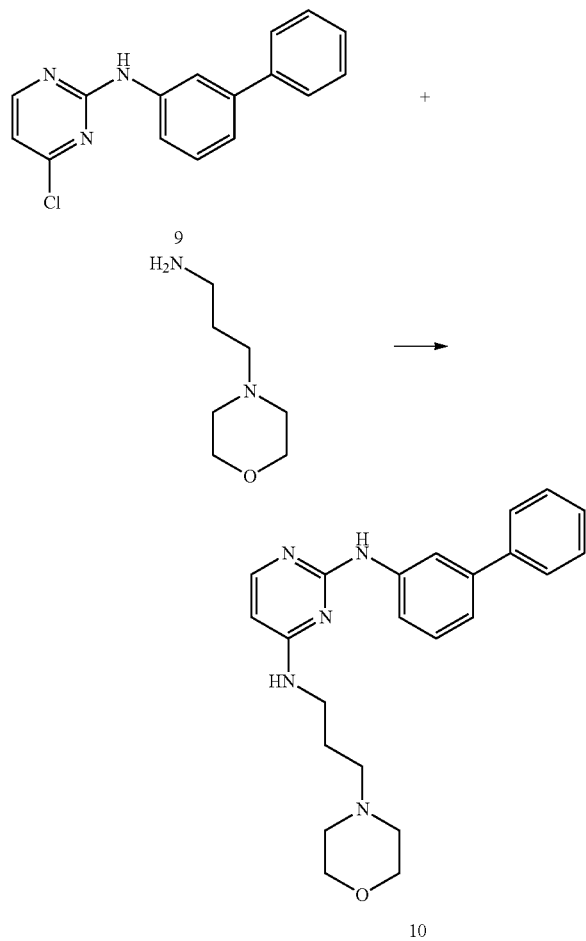

Reagents and conditions (c): DIPEA, THF, reflux, 18 h

Example 3

N²-Biphenyl-3-yl-N⁴-(3-morpholin-4-yl-propyl)-pyrimidine-2,4-diamine (10)

Preparation of 2-(3-biphenylamino)pyrimidin-4(3H)-one (8): To 2-(methylthio)-pyrimidine-4(3H)-one (790 mg, 5.5 mmol) in 5 mL of diglyme is added 3-amino-biphenyl (1.91 g, 11.2 mmol). The resulting mixture is stirred at reflux for 18 hours. The mixture is cooled to room temperature and hexanes are added to form a precipitate which is collected by filtration to afford 1.34 g (92% yield) of the desired compound which is used without purification. MS (ESI, pos. ion) m/z: 264 (M+1).

Preparation of 4-chloro-N-(3-biphenyl)pyrimidin-2-amine (9): To 2-(3-biphenylamino)pyrimidin-4(3H)-one (1.34 g, 5.0 mmol), and N,N-dimethylaniline (1.5 mL) is added 10 mL of phosphorus oxychloride. The resulting mixture is heated at reflux for 1 hour, cooled to room temperature and concentrated in vacuo. The residue is neutralized with 1M NaOH (aqueous). The organics are extracted t portions of EtOAc (2×50 mL). The combined organic layers are washed with brine, dried (MgSO₄), and concentrated in vacuo. The residue is purified over silica (5% EtOAc in hexanes) to afford 780 mg (54% yield) of the desired compound. MS (ESI, pos. ion) m/z: 282 (M+1).

Preparation of N²-biphenyl-3-yl-N⁴-(3-morpholin-4-yl-propyl)-pyrimidine-2,4-diamine (10): To 4-chloro-N-(3-biphenyl)pyrimidin-2-amine (301.0 mg, 1.07 mmol) in 5 mL THF is added potassium carbonate (396 mg, 2.15 mmol) followed by 3-morpholinopropyl-amine (0.3 mL, 2.05 mmol). The resulting mixture is heated at reflux for 96 hours. The reaction is cooled to room temperature and concentrated in vacuo. The residue is diluted with 15 mL of water and extracted with EtOAc (3×20 mL). The combined organic layers are washed with water and brine, dried (MgSO₄) and concentrated in vacuo. The crude product is purified over silica (5% MeOH in CH₂Cl₂) to afford 362 mg (87% yield) of the desired compound. $^1$H NMR (DMSO-$d_6$, 300 MHz): δ1.69 (m, 2H), 2.26-2.32 (m, 6H), 3.38 (m, 2H), 3.54 (t, J=4.2 Hz, 4H), 5.95 (d, J=6.0 Hz, 1H), 7.15 (d, J=7.5 Hz, 1H), 7.21 (bs, 1H), 7.29-7.39 (m, 2H), 7.47 (t, J=8.1 Hz, 2H), 7.62 (d, J=8.1 Hz, 2H), 7.73 (bs, 1H), 7.81 (d, J=6.0 Hz, 1H), 8.23 (bs, 1H), 9.05 (s, 1H). MS (ESI, pos. ion) m/z: 390 (M+1).

The following are non-limiting examples of compounds which comprise the third aspect of Category I of the present invention, the characterization of which will assist the formulator in establishing the chemical formulae of compounds which are not specifically exemplified herein. Alternatively, these compounds may also be synthesized by the synthetic route or methods described earlier in Scheme II.

N²-(3'-Nitrobiphenyl-3-yl)-10-(3-morpholin-4-yl-propyl)-pyrimidine-2,4-diamine: $^1$H NMR (CDCl₃, 300 MHz) δ 1.80-1.88 (m, 2H), 2.52 (t, J=4.5 Hz, 4H), 2.55 (t, J=6.3 Hz, 2H), 3.56 (bs, 2H), 3.76 (t, J=4.5 Hz, 4H), 5.90 (d, J=6.0 Hz, 1H), 7.28 (d, J=7.8 Hz, 1H), 7.29 (s, 1H), 7.44 (t, J=7.8 Hz, 1H), 7.47 (bs, 1H), 7.58 (bs, 1H), 7.64 (t, J=7.5 Hz, 1H), 7.93 (d, J=6.0 Hz, 1H), 7.97 (d, J=7.5 Hz, 1H), 8.15 (bs, 1H), 8.23 (d, J=7.5 Hz, 1H), 8.52 (bs, 1H); HRMS calcd for $C_{23}H_{26}N_6O_3$, 435.2145 m/z (M+H)⁺; observed 435.2125 m/z.

Further compounds which are encompassed within the third aspect of Category II of the present invention but which are not fully exemplified include:

N²-(3'-Nitro-biphenyl-3-yl)-N⁴-(3-pyrrolidin-1-yl-propyl)-pyrimidine-2,4-diamine;

N²-(3'-Nitro-biphenyl-3-yl)-N⁴-(3-pyrrolin-1-yl-propyl)-pyrimidine-2,4-diamine;

N²-(3'-Nitro-biphenyl-3-yl)-N⁴-(3-imidazolidin-1-yl-propyl)-pyrimidine-2,4-diamine;

N²-(3'-Nitro-biphenyl-3-yl)-N⁴-(3-imidazolin-1-yl-propyl)-pyrimidine-2,4-diamine;

N²-(3'-Nitro-biphenyl-3-yl)-N⁴-(3-pyrazolidin-1-yl-propyl)-pyrimidine-2,4-diamine;

N²-(3'-Nitro-biphenyl-3-yl)-N⁴-(3-piperidin-1-yl-propyl)-pyrimidine-2,4-diamine;

N²-(3'-Nitro-biphenyl-3-yl)-N⁴-(3-piperazin-1-yl-propyl)-pyrimidine-2,4-diamine;

N²-(3'-Nitro-biphenyl-3-yl)-N⁴-(3-pyrazolidin-1-yl-propyl)-pyrimidine-2,4-diamine;

N²-(3'-Chloro-biphenyl-3-yl)-N⁴-(3-pyrrolidin-1-yl-propyl)-pyrimidine-2,4-diamine;

N²-(3'-Chloro-biphenyl-3-yl)-N⁴-(3-pyrrolin-1-yl-propyl)-pyrimidine-2,4-diamine;
N²-(3'-Chloro-biphenyl-3-yl)-N⁴-(3-imidazolidin-1-yl-propyl)-pyrimidine-2,4-diamine;
N²-(3'-Chloro-biphenyl-3-yl)-N⁴-(3-imidazolin-1-yl-propyl)-pyrimidine-2,4-diamine;
N²-(3'-Chloro-biphenyl-3-yl)-N⁴-(3-pyrazolidin-1-yl-propyl)-pyrimidine-2,4-diamine;
N²-(3'-Chloro-biphenyl-3-yl)-N⁴-(3-piperidin-1-yl-propyl)-pyrimidine-2,4-diamine;
N²-(3'-Chloro-biphenyl-3-yl)-N⁴-(3-piperazin-1-yl-propyl)-pyrimidine-2,4-diamine;
N²-(3'-Chloro-biphenyl-3-yl)-N⁴-(3-pyrazolidin-1-yl-propyl)-pyrimidine-2,4-diamine;
N²-(3'-Chloro-biphenyl-3-yl)-N⁴-(3-morpholin-4-yl-propyl)-pyrimidine-2,4-diamine;
N²-(3'-Fluoro-biphenyl-3-yl)-N⁴-(3-pyrrolidin-1-yl-propyl)-pyrimidine-2,4-diamine;
N²-(3'-Fluoro-biphenyl-3-yl)-N⁴-(3-pyrrolin-1-yl-propyl)-pyrimidine-2,4-diamine;
N²-(3'-Fluoro-biphenyl-3-yl)-N⁴-(3-imidazolidin-1-yl-propyl)-pyrimidine-2,4-diamine;
N²-(3'-Fluoro-biphenyl-3-yl)-N⁴-(3-imidazolin-1-yl-propyl)-pyrimidine-2,4-diamine;
N²-(3'-Fluoro-biphenyl-3-yl)-N⁴-(3-pyrazolidin-1-yl-propyl)-pyrimidine-2,4-diamine;
N²-(3'-Fluoro-biphenyl-3-yl)-N⁴-(3-piperidin-1-yl-propyl)-pyrimidine-2,4-diamine;
N²-(3'-Fluoro-biphenyl-3-yl)-N⁴-(3-piperazin-1-yl-propyl)-pyrimidine-2,4-diamine;
N²-(3'-Fluoro-biphenyl-3-yl)-N⁴-(3-pyrazolidin-1-yl-propyl)-pyrimidine-2,4-diamine;
N²-(3'-Fluoro-biphenyl-3-yl)-N⁴-(3-morpholin-4-yl-propyl)-pyrimidine-2,4-diamine;
N²-(3'-Methyl-biphenyl-3-yl)-N⁴-(3-pyrrolidin-1-yl-propyl)-pyrimidine-2,4-diamine;
N²-(3'-Methyl-biphenyl-3-yl)-N⁴-(3-pyrrolin-1-yl-propyl)-pyrimidine-2,4-diamine;
N²-(3'-Methyl-biphenyl-3-yl)-N⁴-(3-imidazolidin-1-yl-propyl)-pyrimidine-2,4-diamine;
N²-(3'-Methyl-biphenyl-3-yl)-N⁴-(3-imidazolin-1-yl-propyl)-pyrimidine-2,4-diamine;
N²-(3'-Methyl-biphenyl-3-yl)-N⁴-(3-pyrazolidin-1-yl-propyl)-pyrimidine-2,4-diamine;
N²-(3'-Methyl-biphenyl-3-yl)-N⁴-(3-piperidin-1-yl-propyl)-pyrimidine-2,4-diamine;
N²-(3'-Methyl-biphenyl-3-yl)-N⁴-(3-piperazin-1-yl-propyl)-pyrimidine-2,4-diamine;
N²-(3'-Methyl-biphenyl-3-yl)-N⁴-(3-pyrazolidin-1-yl-propyl)-pyrimidine-2,4-diamine;
N²-(3'-Methyl-biphenyl-3-yl)-N⁴-(3-morpholin-4-yl-propyl)-pyrimidine-2,4-diamine;
N²-(3'-Methoxy-biphenyl-3-yl)-N⁴-(3-pyrrolidin-1-yl-propyl)-pyrimidine-2,4-diamine;
N²-(3'-Methoxy-biphenyl-3-yl)-N⁴-(3-pyrrolin-1-yl-propyl)-pyrimidine-2,4-diamine;
N²-(3'-Methoxy-biphenyl-3-yl)-N⁴-(3-imidazolidin-1-yl-propyl)-pyrimidine-2,4-diamine;
N²-(3'-Methoxy-biphenyl-3-yl)-N⁴-(3-imidazolin-1-yl-propyl)-pyrimidine-2,4-diamine;
N²-(3'-Methoxy-biphenyl-3-yl)-N⁴-(3-pyrazolidin-1-yl-propyl)-pyrimidine-2,4-diamine;
N²-(3'-Methoxy-biphenyl-3-yl)-N⁴-(3-piperidin-1-yl-propyl)-pyrimidine-2,4-diamine;
N²-(3'-Methoxy-biphenyl-3-yl)-N⁴-(3-piperazin-1-yl-propyl)-pyrimidine-2,4-diamine;
N²-(3'-Methoxy-biphenyl-3-yl)-N⁴-(3-pyrazolidin-1-yl-propyl)-pyrimidine-2,4-diamine;
N²-(3'-Methoxy-biphenyl-3-yl)-N⁴-(3-morpholin-4-yl-propyl)-pyrimidine-2,4-diamine;
N²-(3'-Dimethylamino-biphenyl-3-yl)-N⁴-(3-pyrrolidin-1-yl-propyl)-pyrimidine-2,4-diamine;
N²-(3'-Dimethylamino-biphenyl-3-yl)-N⁴-(3-pyrrolin-1-yl-propyl)-pyrimidine-2,4-diamine;
N²-(3'-Dimethylamino-biphenyl-3-yl)-N⁴-(3-imidazolidin-1-yl-propyl)-pyrimidine-2,4-diamine;
N²-(3'-Dimethylamino-biphenyl-3-yl)-N⁴-(3-imidazolin-1-yl-propyl)-pyrimidine-2,4-diamine;
N²-(3'-Dimethylamino-biphenyl-3-yl)-N⁴-(3-pyrazolidin-1-yl-propyl)-pyrimidine-2,4-diamine;
N²-(3'-Dimethylamino-biphenyl-3-yl)-N⁴-(3-piperidin-1-yl-propyl)-pyrimidine-2,4-diamine;
N²-[(-(3'-Dimethylamino-biphenyl-3-yl)-N⁴-(3-piperazin-1-yl-propyl)-pyrimidine-2,4-diamine;
N²-(3'-Dimethylamino-biphenyl-3-yl)-N⁴-(3-pyrazolidin-1-yl-propyl)-pyrimidine-2,4-diamine; and
N²-(3'-Dimethylamino-biphenyl-3-yl)-N'-(3-morpholin-4-yl-propyl)-pyrimidine-2,4-diamine.

The compounds which comprise Category II of the present invention are 2,4-diaminopyrimidines having the formula:

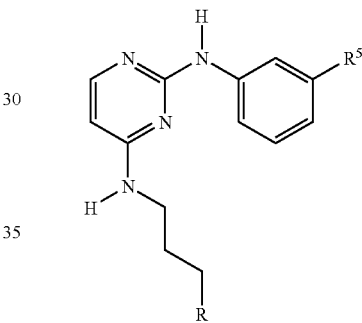

wherein R is a heterocyclic unit attached to the core scaffold by way of a nitrogen atom and $R^1$ is a phenyl unit substituted by different category of $R^5$ units having the formula:

-L¹-R⁶ and $L^1$ and $R^6$ are further defined herein below in Table IV.

TABLE IV

| No | R | L¹ | R⁶ |
|---|---|---|---|
| 281 | pyrrolidin-1-yl | —SO₂NH— | —H |
| 282 | pyrrolin-1-yl | —SO₂NH— | —H |
| 283 | imidazolidin-1-yl | —SO₂NH— | —H |
| 284 | imidazolin-1-yl | —SO₂NH— | —H |
| 285 | pyrazolidin-1-yl | —SO₂NH— | —H |
| 286 | pyrazolin-1-yl | —SO₂NH— | —H |
| 287 | piperidin-1-yl | —SO₂NH— | —H |
| 288 | piperazin-1-yl | —SO₂NH— | —H |
| 289 | 4-methylpiperazin-1-yl | —SO₂NH— | —H |
| 290 | morpholin-4-yl | —SO₂NH— | —H |
| 291 | pyrrolidin-1-yl | —SO₂NH— | —CH₃ |
| 292 | pyrrolin-1-yl | —SO₂NH— | —CH₃ |
| 293 | imidazolidin-1-yl | —SO₂NH— | —CH₃ |
| 294 | imidazolin-1-yl | —SO₂NH— | —CH₃ |
| 295 | pyrazolidin-1-yl | —SO₂NH— | —CH₃ |
| 296 | pyrazolin-1-yl | —SO₂NH— | —CH₃ |
| 297 | piperidin-1-yl | —SO₂NH— | —CH₃ |
| 298 | piperazin-1-yl | —SO₂NH— | —CH₃ |
| 299 | 4-methylpiperazin-1-yl | —SO₂NH— | —CH₃ |
| 300 | morpholin-4-yl | —SO₂NH— | —CH₃ |

TABLE IV-continued

| No | R | L¹ | R⁶ |
|---|---|---|---|
| 301 | pyrrolidin-1-yl | —SO₂NH— | phenyl |
| 302 | pyrrolin-1-yl | —SO₂NH— | phenyl |
| 303 | imidazolidin-1-yl | —SO₂NH— | phenyl |
| 304 | imidazolin-1-yl | —SO₂NH— | phenyl |
| 305 | pyrazolidin-1-yl | —SO₂NH— | phenyl |
| 306 | pyrazolin-1-yl | —SO₂NH— | phenyl |
| 307 | piperidin-1-yl | —SO₂NH— | phenyl |
| 308 | piperazin-1-yl | —SO₂NH— | phenyl |
| 309 | 4-methylpiperazin-1-yl | —SO₂NH— | phenyl |
| 310 | morpholin-4-yl | —SO₂NH— | phenyl |
| 311 | pyrrolidin-1-yl | —SO₂NH— | pyridin-3-yl |
| 312 | pyrrolin-1-yl | —SO₂NH— | pyridin-3-yl |
| 313 | imidazolidin-1-yl | —SO₂NH— | pyridin-3-yl |
| 314 | imidazolin-1-yl | —SO₂NH— | pyridin-3-yl |
| 315 | pyrazolidin-1-yl | —SO₂NH— | pyridin-3-yl |
| 316 | pyrazolin-1-yl | —SO₂NH— | pyridin-3-yl |
| 317 | piperidin-1-yl | —SO₂NH— | pyridin-3-yl |
| 318 | piperazin-1-yl | —SO₂NH— | pyridin-3-yl |
| 319 | 4-methylpiperazin-1-yl | —SO₂NH— | pyridin-3-yl |
| 320 | morpholin-4-yl | —SO₂NH— | pyridin-3-yl |
| 321 | pyrrolidin-1-yl | —NHC(O)— | phenyl |
| 322 | pyrrolin-1-yl | —NHC(O)— | phenyl |
| 323 | imidazolidin-1-yl | —NHC(O)— | phenyl |
| 324 | imidazolin-1-yl | —NHC(O)— | phenyl |
| 325 | pyrazolidin-1-yl | —NHC(O)— | phenyl |
| 326 | pyrazolin-1-yl | —NHC(O)— | phenyl |
| 327 | piperidin-1-yl | —NHC(O)— | phenyl |
| 328 | piperazin-1-yl | —NHC(O)— | phenyl |
| 329 | 4-methylpiperazin-1-yl | —NHC(O)— | phenyl |
| 330 | morpholin-4-yl | —NHC(O)— | phenyl |
| 331 | pyrrolidin-1-yl | —NHC(O)— | pyridin-3-yl |
| 332 | pyrrolin-1-yl | —NHC(O)— | pyridin-3-yl |
| 333 | imidazolidin-1-yl | —NHC(O)— | pyridin-3-yl |
| 334 | imidazolin-1-yl | —NHC(O)— | pyridin-3-yl |
| 335 | pyrazolidin-1-yl | —NHC(O)— | pyridin-3-yl |
| 336 | pyrazolin-1-yl | —NHC(O)— | pyridin-3-yl |
| 337 | piperidin-1-yl | —NHC(O)— | pyridin-3-yl |
| 338 | piperazin-1-yl | —NHC(O)— | pyridin-3-yl |
| 339 | 4-methylpiperazin-1-yl | —NHC(O)— | pyridin-3-yl |
| 340 | morpholin-4-yl | —NHC(O)— | pyridin-3-yl |
| 341 | pyrrolidin-1-yl | —C(O)NH— | pyridin-3-yl |
| 342 | pyrrolin-1-yl | —C(O)NH— | pyridin-3-yl |
| 343 | imidazolidin-1-yl | —C(O)NH— | pyridin-3-yl |
| 344 | imidazolin-1-yl | —C(O)NH— | pyridin-3-yl |
| 345 | pyrazolidin-1-yl | —C(O)NH— | pyridin-3-yl |
| 346 | pyrazolin-1-yl | —C(O)NH— | pyridin-3-yl |
| 347 | piperidin-1-yl | —C(O)NH— | pyridin-3-yl |
| 348 | piperazin-1-yl | —C(O)NH— | pyridin-3-yl |
| 349 | 4-methylpiperazin-1-yl | —C(O)NH— | pyridin-3-yl |
| 350 | morpholin-4-yl | —C(O)NH— | pyridin-3-yl |
| 351 | pyrrolidin-1-yl | —CH₂CH₂— | pyridin-3-yl |
| 352 | pyrrolin-1-yl | —CH₂CH₂— | pyridin-3-yl |
| 353 | imidazolidin-1-yl | —CH₂CH₂— | pyridin-3-yl |
| 354 | imidazolin-1-yl | —CH₂CH₂— | pyridin-3-yl |
| 355 | pyrazolidin-1-yl | —CH₂CH₂— | pyridin-3-yl |
| 356 | pyrazolin-1-yl | —CH₂CH₂— | pyridin-3-yl |
| 357 | piperidin-1-yl | —CH₂CH₂— | pyridin-3-yl |
| 358 | piperazin-1-yl | —CH₂CH₂— | pyridin-3-yl |
| 359 | 4-methylpiperazin-1-yl | —CH₂CH₂— | pyridin-3-yl |
| 360 | morpholin-4-yl | —CH₂CH₂— | pyridin-3-yl |

The compounds which comprise Category II of the present invention can be prepared by the procedure outlined herein below in Scheme IV and Example 4.

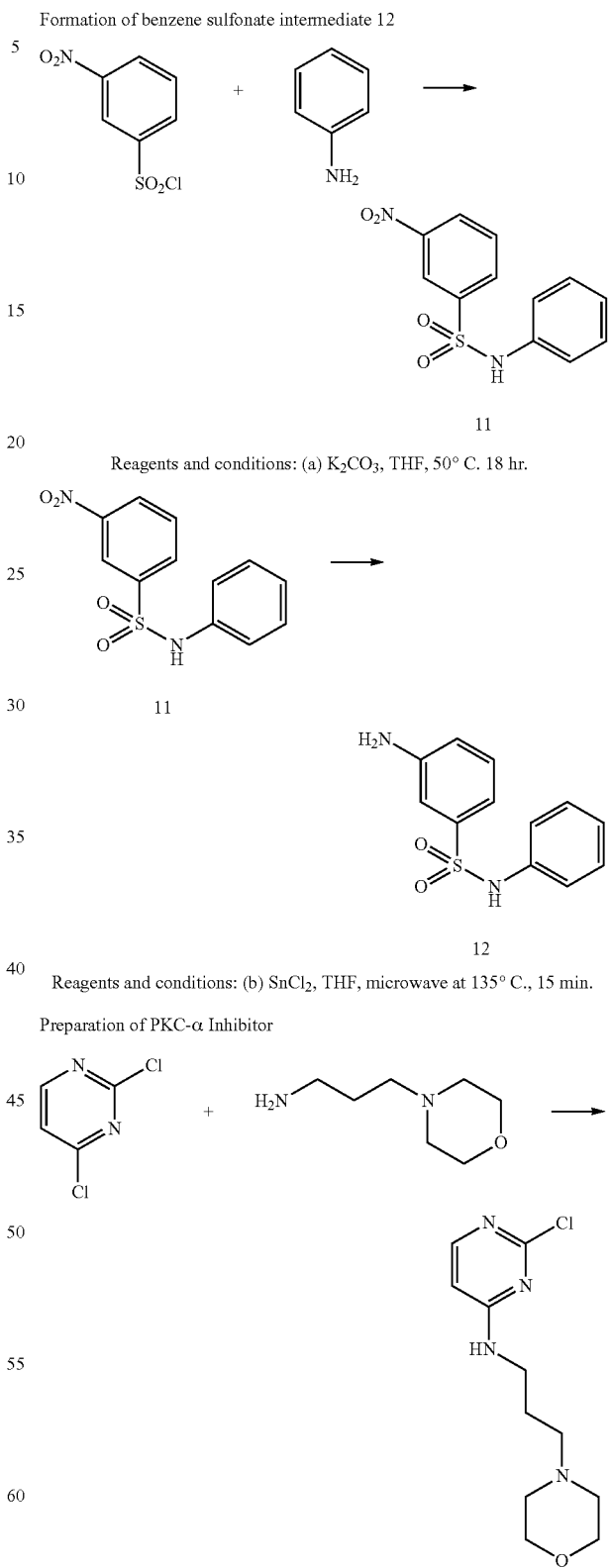

Scheme IV

Formation of benzene sulfonate intermediate 12

Reagents and conditions: (a) K₂CO₃, THF, 50° C. 18 hr.

Reagents and conditions: (b) SnCl₂, THF, microwave at 135° C., 15 min.

Preparation of PKC-α Inhibitor

Reagents and conditions: (c) n-BuOH, H₂O, DIPEA, rt, 18 hr.

-continued

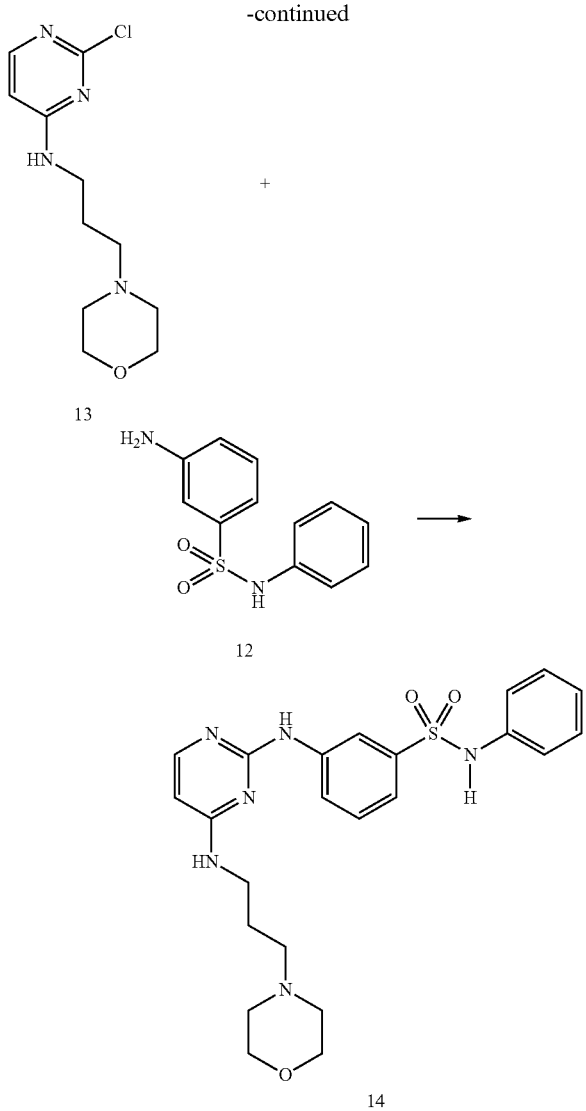

Reagents and conditions (d): EtOH/H₂O (1:1), HCl, 70° C. 18 hr.

Example 4

N-{3-[4-(3-Morpholin-4-yl-propylamino)-pyrimidin-2-ylamino]-phenyl}-benzenesulfonamide (14)

The intermediate, 3-amino-N-phenylbenzenesulfonamide (12), can be conveniently prepared by the following steps from aniline and 3-nitrobenzene-1-sulfonyl chloride. Other sulfonamide intermediates can be prepared in a like manner, the formulator making adjustments to the reaction conditions which are well known to those skilled in the art.

Preparation of 3-nitro-N-phenylbenzenesulfonamide (11): To 3-nitrobenzene-1-sulfonyl chloride (296.9 mg, 1.340 mmol) is added THF (20 mL), aniline (134.8 mg, 1.447 mmol) and potassium carbonate (408.5 mg, 2.955 mmol). The resulting mixture is heated at 50° C. for 16 hours. The reaction mixture is subsequently cooled and concentrated in vacuo after which the residue is treated with 10 ml of H₂O and extracted with EtOAc (75 mL). The organic layer is washed with saturated aqueous NaCl (2×75 mL), dried (MgSO₄), and concentrated in vacuo. The residue is purified over silica (CH₂Cl₂) to afford 257 mg (69% yield) of the desired compound. MS (ESI, pos. ion) m/z: 279 (M+1).

Preparation of 3-amino-N-phenylbenzenesulfonamide (12): To 3-nitro-N-phenylbenzenesulfonamide (255.5 mg, 0.919 mmol) in 4 mL of THF is added SnCl₂ dihydrate (1.015 g, 4.486 mmol). The resulting mixture is heated in a microwave reactor at a power of 75 Watts and 135° C. for 1 min then at 15 Watts and 135° C. for 14 min. The reaction is cooled to room temperature, diluted with EtOAc (20 mL), washed with saturated aqueous NaHCO₃ (10 mL) and allowed to stir for about 12 hours. The reaction mixture is then extracted with EtOAc (75 mL). The organic layer is washed with H₂O (75 mL), saturated aqueous NaCl (2×75 mL), dried (MgSO₄) and concentrated in vacuo to yield a yellow residue. This residue is purified over silica (0-4% MeOH in CH₂Cl₂) to afford 178 mg (78% yield) of the desired compound. $^1$H NMR (DMSO-$d_6$, 300 MHz): δ 5.57 (s, 2H), 6.69 (d, J=8.1 Hz, 1H), 6.84 (d, J=7.5 Hz, 1H), 6.95 (s, 1H), 6.99 (t, J=7.5 Hz, 1H), 7.07 (d, J=8.1 Hz, 2H), 7.12 (t, J=8.1 Hz, 1H), 7.21 (t, J=8.1 Hz, 2H), 10.12 (s, 1H). MS (ESI, pos. ion) m/z: 249 (M+1).

Preparation of 2-chloro-N-(3-morpholinopropyl)pyrimidin-4-amine (13): To 2,4-dichloropyrimidine (5.0 g, 33.5 mmol), diisopropylethylamine (5.85 ml, 33.5 mmol) in 50 mL of a 1:1 mixture of n-BuOH—H₂O (1:1) is added 3-morpholinopropan-1-amine (4.90 mL, 33.5 mmol). The resulting mixture is stirred for 18 hours at room temperature. The mixture is then concentrated in vacuo, diluted with 30 mL H₂O and extracted with EtOAc (3×75 mL). Combined organic layers are washed with saturated aqueous NaHCO₃ (2×75 mL), saturated aqueous NaCl (2×75 mL), and dried (MgSO₄). The residue is purified over silica (25% EtOAc in hexanes) to afford 4.5 g (53% yield) of the desired compound. $^1$H NMR (CDCl₃, 300 MHz): δ 1.81 (m, 2H), 2.43-2.62 (m, 6H), 3.30 (m, 2H), 3.79-3.94 (m, 4H), 6.23 (d, J=5.4 Hz, 1H), 6.92 (bs, 1H), 7.99 (bs, 1H). MS (ESI, pos. ion) m/z: 257 (M+1).

Preparation of N-{3-[4-(3-morpholin-4-yl-propylamino)-pyrimidin-2-ylamino]-phenyl}-benzenesulfonamide (14): To 2-chloro-N-(3-morpholinopropyl)pyrimidin-4-amine, 13, (103.1 mg, 0.4016 mmol) in 30 mL of EtOH—H₂O (1:1) is added 3-amino-N-phenylbenzenesulfonamide, 12, (116.5 mg, 0.4697 mmol) and 4 drops concentrated HCl. The resulting mixture is heated at 70° C. with sufficient stirring for 16 hours. The reaction mixture is then cooled to room temperature and concentrated in vacuo. The product is extracted with EtOAc (100 mL). The combined organic layers are washed with H₂O (2×75 mL) and saturated aqueous NaCl (2×75 mL), dried (MgSO₄), and concentrated in vacuo. The resulting residue is purified over silica (5-10% MeOH in CH₂Cl₂) to afford 157 mg (83% yield) of the desired compound. $^1$H NMR (DMSO-$d_6$, 300 MHz): δ 1.72 (m, 2H), 2.34-2.39, (m, 6H), 3.30-3.41 (m, 2H), 3.55-59 (m, 4H), 5.99 (d, J=5.7 Hz, 1H), 7.00 (t, J=7.5 Hz, 1H), 7.11 (d, J=7.5 Hz, 2H), 7.18-7.28 (m, 4H), 7.36 (t, J=7.8 Hz, 1H), 7.81 (bs, 2H), 8.56 (s, 1H), 9.33 (s, 1H), 10.24 (bs, 1H). HRMS calcd for $C_{23}H_{28}N_6O_3$, 469.2022 m/z (M+H)$^+$; observed 469.2020 m/z.

The following are non-limiting examples of compounds which comprise Category II of the present invention, the characterization of which will assist the formulator in establishing the chemical formulae of compounds which are not specifically exemplified herein. Alternatively, these compounds may also be synthesized by the synthetic route or methods described earlier in Scheme I.

$N^2$-[3-(1H-Imidazol-1-ylmethyl)-phenyl]-$N^4$-(3-morpholin-4-yl-propyl)-pyrimidine-2,4-diamine: $^1$H NMR (CDCl₃, 300 MHz) δ 1.84 (q, J=6.3 Hz, 2H), 2.27-2.37 (m, 2H), 2.48-2.56 (m, 4H), 3.36-3.44 (m, 2H), 3.77 (t, J=4.5 Hz, 4H), 5.14 (s, 2H), 5.86 (d, J=6.0 Hz, 1H), 6.27 (bs, 1H), 6.80 (d, J=7.5 Hz, 1H), 6.96 (s, 1H), 7.11 (s, 1H), 7.24-7.31 (m, 2H), 7.45 (d, J=7.8 Hz, 1H), 7.60 (d, J=5.4 Hz, 2H), 7.90 (d, J=5.7 Hz, 1H); HRMS calcd for $C_{21}H_{27}N_7O$, 394.2355 m/z $(M+H)^+$; observed 394.2371 m/z.

3-[4-(3-Morpholin-4-yl-propylamino)-pyrimidin-2-ylamino]-N-(pyridin-3-ylmethyl)-benzenesulfonamide. $^1$H NMR (DMSO-$d_6$, 300 MHz): δ 1.62-1.77 (m, 2H), 2.28-2.40 (m, 6H), 3.35-3.42 (m, 2H), 3.52-3.57 (m, 4H), 4.05 (d, J=5.4 Hz, 2H), 6.00 (d, J=5.4 Hz, 1H), 7.28-7.34 (m, 3H), 7.42 (t, J=7.8 Hz, 1H), 7.67 (d, J=7.8 Hz, 1H), 7.75-7.95 (m, 2H), 8.15 (t, J=6.0 Hz, 1H), 8.44 (d, J=6.0 Hz, 1H), 8.45 (s, 1H), 8.59 (s, 1H), 9.33 (s, 1H). HRMS calcd for $C_{23}H_{29}N_7O_3S$, 484.2131 m/z $(M+H)^+$; observed 484.2148 m/z.

$N^2$-[3-(1H-Indol-2-ylmethyl)-phenyl]-$N^4$-(3-morpholin-4-yl-propyl)-pyrimidine-2,4-diamine.

3-[4-(3-Morpholin-4-yl-propylamino)-pyrimidin-2-ylamino]-benzenesulfonamide $^1$H NMR (DMSO-$d_6$, 300 MHz) δ 2.01-2.12 (m, 2H), 2.96-3.12 (m, 2H), 3.14-3.19 (m, 2H), 3.36-3.43 (m, 2H), 3.48-3.56 (m, 2H), 3.79-4.10 (m, 4H), 6.32 (d, J=7.2 Hz, 1H), 7.49 (s, 2H), 7.58-7.65 (m, 3H), 7.92 (d, J=7.2 Hz, 1H), 8.49 (s, 1H), 9.34 (bs, 1H), 11.01 (s, 1H); HRMS calcd for $C_{17}H_{24}N_6O_3S$, 393.1709 m/z $(M+H)^+$; observed 393.1719 m/z. N-(3-Chlorophenyl)-3-[4-(3-pyrrolidin-1-yl-propylamino)-pyrimidin-2-ylamino]-benzamide: HRMS calcd for $C_{24}H_{27}N_6OCl$, 451.2013 m/z $(M+H)^+$; observed 451.2016 m/z.

N-{3-[4-(3-Morpholin-4-yl-propylamino)-pyrimidin-2-ylamino]-phenyl}-benzamide $^1$H NMR (DMSO-$d_6$, 300 MHz): 1.67 (m, 2H), 2.18-2.34 (m, 6H), 3.29-3.42 (m, 2H), 3.53 (t, J=4.5 Hz, 4H), 5.93 (d, J=5.7 Hz, 1H), 7.08-7.25 (m, 3H), 7.45 (bs, 1H), 7.50-7.59 (m, 3H), 7.74-7.85 (m, 1H), 7.96 (d, J=6.9 Hz, 2H), 8.29 (bs, 1H), 8.96 (s, 1H), 10.15 (s, 1H). HRMS calcd for $C_{24}H_{28}N_6O_2$, 433.2352 m/z $(M+H)^+$; observed 433.2357 m/z.

N-Isopropyl-3-[4-(3-pyrrolidin-1-yl-propylamino)-pyrimidin-2-ylamino]-benzamide: HRMS calcd for $C_{21}H_{30}N_6O$, 383.2559 m/z $(M+H)^+$; observed 383.2564 m/z.

$N^2$-[3-(4-Methyl-piperazine-1-sulfonyl)phenyl]-$N^4$-(3-morpholin-4-ylpropyl)-pyrimidine-2,4-diamine. $^1$H NMR (DMSO-$d_6$, 300 MHz): δ 1.67-1.78 (m, 2H), 2.15 (s, 3H), 2.28-2.45 (m, 10H), 2.85-2.98 (m, 4H), 3.32-3.47 (m, 2H), 3.58 (t, J=4.5 Hz, 4H), 6.08 (d, J=5.7 Hz, 1H), 7.19 (d, J=8.1 Hz, 1H), 7.30 (s, 1H), 7.49 (t, J=8.1 Hz, 1H), 7.83 (d, J=5.7 Hz, 1H), 7.92 (bs, 1H), 8.53 (s, 1H), 9.40 (s, 1H). HRMS calcd for, $C_{22}H_{33}N_7O_3S$ 476.2444 m/z $(M+H)^+$; observed 476.2449 m/z.

N-{3-[4-(3-Morpholin-4-yl-propylamino)-pyrimidin-2-ylamino]-phenyl}-nicotinamide. $^1$H NMR (DMSO-$d_6$, 300 MHz): δ 1.62-1.73 (m, 2H), 2.20-2.33 (m, 6H), 3.29-3.40 (m, 2H), 3.53 (t, J=4.5 Hz, 4H), 5.93 (d, J=6.0 Hz, 1H), 7.08-7.24 (m, 3H), 7.46 (bs, 1H), 7.56 (dd, J=4.8, 8.1 Hz, 1H), 7.80 (d, J=6.0 Hz, 1H), 8.29 (d, J=8.1 Hz, 2H), 8.76 (d, J=4.8 Hz, 1H), 8.99 (s, 1H), 9.10 (s, 1H), 10.35 (s, 1H). HRMS calcd for $C_{23}H_{27}N_7O_2$, 434.2304 m/z $(M+H)^+$; observed 434.2300 m/z.

N-(3-Chloro-phenyl)-3-[4-(3-pyrrolidin-1-yl-propylamino)-pyrimidin-2-ylamino]-benzamide: HRMS calcd for $C_{24}H_{28}N_6OCl$, 451.2013 m/z $(M+H)^+$; observed 451.2016 m/z.

N-Benzyl-3-[4-(3-pyrrolidin-1-yl-propylamino)-pyrimidin-2-ylamino]-benzamide: HRMS calcd for $C_{25}H_{31}N_6O$, 431.2559 m/z $(M+H)^+$; observed 431.2561 m/z.

4-Dimethylamino-N-{3-[4-(3-morpholin-4-yl-propylamino)-pyrimidin-2-ylamino]-phenyl}-benzamide: HRMS calcd for $C_{26}H_{34}N_7O_2$, 476.2774 m/z $(M+H)^+$; observed 476.2787 m/z.

[4-(3-Morpholin-4-yl-propylamino)-pyrimidin-2-ylamino]-N-phenylbenzenesulfonamide: HRMS calcd for $C_{23}H_{29}N_6O_3S$, 469.2022 m/z $(M+H)^+$; observed 469.2020 m/z.

3-[4-(3-Morpholin-4-yl-propylamino)-pyrimidin-2-ylamino]-N-(2-pyridin-3-yl-ethyl)-benzenesulfonamide: HRMS calcd for $C_{24}H_{32}N_7O_3S$, 498.2287 m/z $(M+H)^+$; observed 498.2300 m/z.

N-{3-[4-(3-Morpholin-4-yl-propylamino)-pyrimidin-2-ylamino]-phenyl}-isonicotinamide: HRMS calcd for $C_{23}H_{28}N_7O_2$, 434.2304 m/z $(M+H)^+$; observed 434.2317 m/z.

$N^2$-[3-(Morpholine-4-sulfonyl)-phenyl]-$N^4$-(3-morpholin-4-yl-propyl)-pyrimidine-2,4-diamine: HRMS calcd for $C_{21}H_{31}N_6O_4S$, 463.2128 m/z $(M+H)^+$; observed 463.2135 m/z.

The compounds which comprise Category III of the present invention are 2,4-di-aminopyrimidines having the formula:

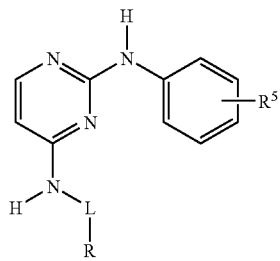

wherein R is a heterocyclic unit chosen from:

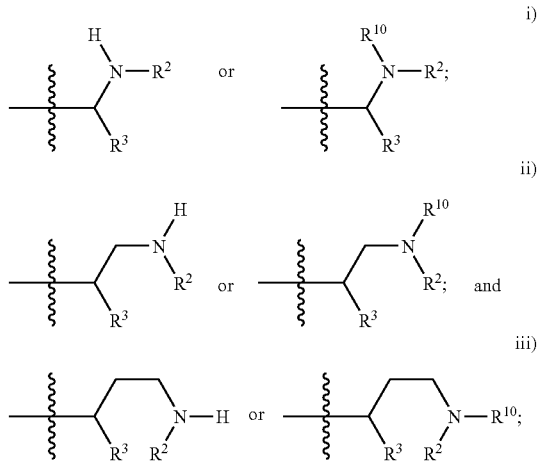

wherein $R^2$, $R^3$, and $R^{10}$ are each defined herein above. The first aspect of Category III relates to $R^1$ units which are phenyl units substituted by one or more $R^5$ units chosen from:
  ii) halogen; —F, —Cl, —Br, and —I;
  iii) nitro; —$NO_2$;
  iv) hydroxy; —OH;
  v) amino or mono- or di-substituted ($C_1$-$C_4$ linear or branched alkyl)amino; inter alia, —$NH_2$, —$NH(CH_3)$, and —$N(CH_3)_2$, vi) substituted or unsubstituted $C_1$-$C_4$ linear or branched alkyl;

vii) substituted or unsubstituted $C_1$-$C_4$ linear or branched alkoxy;

which are further exemplified herein below in Table V and in the following examples.

TABLE V

| No. | L | R | $R^5$ |
|---|---|---|---|
| 361 | —CH$_2$— | piperidine-2-yl | 3-chloro |
| 362 | —CH$_2$— | N-methylpiperidine-2-yl | 3-chloro |
| 363 | —CH$_2$— | piperidine-3-yl | 3-chloro |
| 364 | —CH$_2$— | N-methylpiperidine-3-yl | 3-chloro |
| 365 | —CH$_2$— | piperidine-4-yl | 3-chloro |
| 366 | —CH$_2$— | N-methylpiperidine-4-yl | 3-chloro |
| 367 | —CH$_2$— | pyrrolidin-2-yl | 3-chloro |
| 368 | —CH$_2$— | N-methylpyrrolidin-2-yl | 3-chloro |
| 369 | —CH$_2$— | pyrrolidin-3-yl | 3-chloro |
| 370 | —CH$_2$— | N-methylpyrrolidin-3-yl | 3-chloro |
| 371 | —CH$_2$— | morpholin-2-yl | 3-chloro |
| 372 | —CH$_2$— | morpholin-3-yl | 3-chloro |
| 373 | —CH$_2$CH$_2$— | piperidine-2-yl | 3-chloro |
| 374 | —CH$_2$CH$_2$— | N-methylpiperidine-2-yl | 3-chloro |
| 375 | —CH$_2$CH$_2$— | piperidine-3-yl | 3-chloro |
| 376 | —CH$_2$CH$_2$— | N-methylpiperidine-3-yl | 3-chloro |
| 377 | —CH$_2$CH$_2$— | piperidine-4-yl | 3-chloro |
| 378 | —CH$_2$CH$_2$— | N-methylpiperidine-4-yl | 3-chloro |
| 379 | —CH$_2$CH$_2$— | pyrrolidin-2-yl | 3-chloro |
| 380 | —CH$_2$CH$_2$— | N-methylpyrrolidin-2-yl | 3-chloro |
| 381 | —CH$_2$CH$_2$— | pyrrolidin-3-yl | 3-chloro |
| 382 | —CH$_2$CH$_2$— | N-methylpyrrolidin-3-yl | 3-chloro |
| 383 | —CH$_2$CH$_2$— | morpholin-2-yl | 3-chloro |
| 384 | —CH$_2$CH$_2$— | morpholin-3-yl | 3-chloro |
| 385 | —CH$_2$— | piperidine-2-yl | 3-fluoro |
| 386 | —CH$_2$— | N-methylpiperidine-2-yl | 3-fluoro |
| 387 | —CH$_2$— | piperidine-3-yl | 3-fluoro |
| 388 | —CH$_2$— | N-methylpiperidine-3-yl | 3-fluoro |
| 389 | —CH$_2$— | piperidine-4-yl | 3-fluoro |
| 390 | —CH$_2$— | N-methylpiperidine-4-yl | 3-fluoro |
| 391 | —CH$_2$— | pyrrolidin-2-yl | 3-fluoro |
| 392 | —CH$_2$— | N-methylpyrrolidin-2-yl | 3-fluoro |
| 393 | —CH$_2$— | pyrrolidin-3-yl | 3-fluoro |
| 394 | —CH$_2$— | N-methylpyrrolidin-3-yl | 3-fluoro |
| 395 | —CH$_2$— | morpholin-2-yl | 3-fluoro |
| 396 | —CH$_2$— | morpholin-3-yl | 3-fluoro |
| 397 | —CH$_2$CH$_2$— | piperidine-2-yl | 3-fluoro |
| 398 | —CH$_2$CH$_2$— | N-methylpiperidine-2-yl | 3-fluoro |
| 399 | —CH$_2$CH$_2$— | piperidine-3-yl | 3-fluoro |
| 400 | —CH$_2$CH$_2$— | N-methylpiperidine-3-yl | 3-fluoro |
| 401 | —CH$_2$CH$_2$— | piperidine-4-yl | 3-fluoro |
| 402 | —CH$_2$CH$_2$— | N-methylpiperidine-4-yl | 3-fluoro |
| 403 | —CH$_2$CH$_2$— | pyrrolidin-2-yl | 3-fluoro |
| 404 | —CH$_2$CH$_2$— | N-methylpyrrolidin-2-yl | 3-fluoro |
| 405 | —CH$_2$CH$_2$— | pyrrolidin-3-yl | 3-fluoro |
| 406 | —CH$_2$CH$_2$— | N-methylpyrrolidin-3-yl | 3-fluoro |
| 407 | —CH$_2$CH$_2$— | morpholin-2-yl | 3-fluoro |
| 408 | —CH$_2$CH$_2$— | morpholin-3-yl | 3-fluoro |
| 409 | —CH$_2$— | piperidine-2-yl | 3-methyl |
| 410 | —CH$_2$— | N-methylpiperidine-2-yl | 3-methyl |
| 411 | —CH$_2$— | piperidine-3-yl | 3-methyl |
| 412 | —CH$_2$— | N-methylpiperidine-3-yl | 3-methyl |
| 413 | —CH$_2$— | piperidine-4-yl | 3-methyl |
| 414 | —CH$_2$— | N-methylpiperidine-4-yl | 3-methyl |
| 415 | —CH$_2$— | pyrrolidin-2-yl | 3-methyl |
| 416 | —CH$_2$— | N-methylpyrrolidin-2-yl | 3-methyl |
| 417 | —CH$_2$— | pyrrolidin-3-yl | 3-methyl |
| 418 | —CH$_2$— | N-methylpyrrolidin-3-yl | 3-methyl |
| 419 | —CH$_2$— | morpholin-2-yl | 3-methyl |
| 420 | —CH$_2$— | morpholin-3-yl | 3-methyl |
| 421 | —CH$_2$CH$_2$— | piperidine-2-yl | 3-methyl |
| 422 | —CH$_2$CH$_2$— | N-methylpiperidine-2-yl | 3-methyl |
| 423 | —CH$_2$CH$_2$— | piperidine-3-yl | 3-methyl |
| 424 | —CH$_2$CH$_2$— | N-methylpiperidine-3-yl | 3-methyl |
| 425 | —CH$_2$CH$_2$— | piperidine-4-yl | 3-methyl |
| 426 | —CH$_2$CH$_2$— | N-methylpiperidine-4-yl | 3-methyl |
| 427 | —CH$_2$CH$_2$— | pyrrolidin-2-yl | 3-methyl |
| 428 | —CH$_2$CH$_2$— | N-methylpyrrolidin-2-yl | 3-methyl |
| 429 | —CH$_2$CH$_2$— | pyrrolidin-3-yl | 3-methyl |

TABLE V-continued

| No. | L | R | $R^5$ |
|---|---|---|---|
| 430 | —CH$_2$CH$_2$— | N-methylpyrrolidin-3-yl | 3-methyl |
| 431 | —CH$_2$CH$_2$— | morpholin-2-yl | 3-methyl |
| 432 | —CH$_2$CH$_2$— | morpholin-3-yl | 3-methyl |
| 433 | —CH$_2$— | piperidine-2-yl | 3-methoxy |
| 434 | —CH$_2$— | N-methylpiperidine-2-yl | 3-methoxy |
| 435 | —CH$_2$— | piperidine-3-yl | 3-methoxy |
| 436 | —CH$_2$— | N-methylpiperidine-3-yl | 3-methoxy |
| 437 | —CH$_2$— | piperidine-4-yl | 3-methoxy |
| 438 | —CH$_2$— | N-methylpiperidine-4-yl | 3-methoxy |
| 439 | —CH$_2$— | pyrrolidin-2-yl | 3-methoxy |
| 440 | —CH$_2$— | N-methylpyrrolidin-2-yl | 3-methoxy |
| 441 | —CH$_2$— | pyrrolidin-3-yl | 3-methoxy |
| 442 | —CH$_2$— | N-methylpyrrolidin-3-yl | 3-methoxy |
| 443 | —CH$_2$— | morpholin-2-yl | 3-methoxy |
| 444 | —CH$_2$— | morpholin-3-yl | 3-methoxy |
| 445 | —CH$_2$CH$_2$— | piperidine-2-yl | 3-methoxy |
| 446 | —CH$_2$CH$_2$— | N-methylpiperidine-2-yl | 3-methoxy |
| 447 | —CH$_2$CH$_2$— | piperidine-3-yl | 3-methoxy |
| 448 | —CH$_2$CH$_2$— | N-methylpiperidine-3-yl | 3-methoxy |
| 449 | —CH$_2$CH$_2$— | piperidine-4-yl | 3-methoxy |
| 450 | —CH$_2$CH$_2$— | N-methylpiperidine-4-yl | 3-methoxy |
| 451 | —CH$_2$CH$_2$— | pyrrolidin-2-yl | 3-methoxy |
| 452 | —CH$_2$CH$_2$— | N-methylpyrrolidin-2-yl | 3-methoxy |
| 453 | —CH$_2$CH$_2$— | pyrrolidin-3-yl | 3-methoxy |
| 454 | —CH$_2$CH$_2$— | N-methylpyrrolidin-3-yl | 3-methoxy |
| 455 | —CH$_2$CH$_2$— | morpholin-2-yl | 3-methoxy |
| 456 | —CH$_2$CH$_2$— | morpholin-3-yl | 3-methoxy |

The compounds which comprise the first aspect of Category III of the present invention can be prepared by the procedure outlined herein below in Scheme V and Example 5.

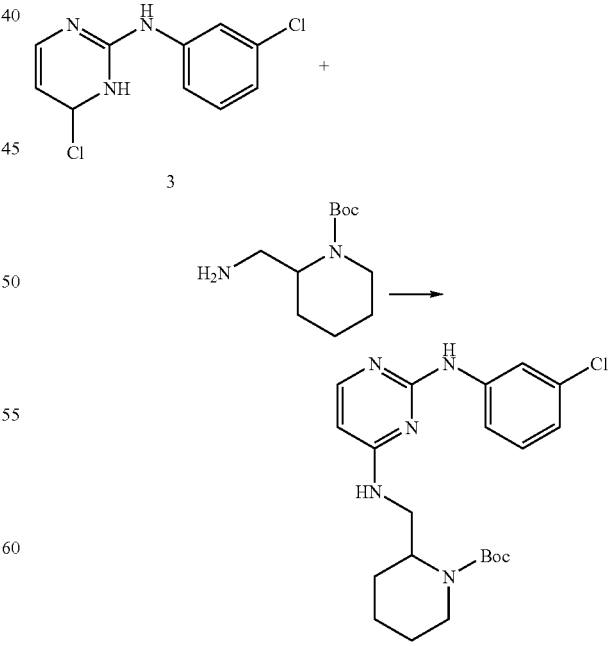

Reagents and conditions (a): DIPEA, THF, reflux, 18 h

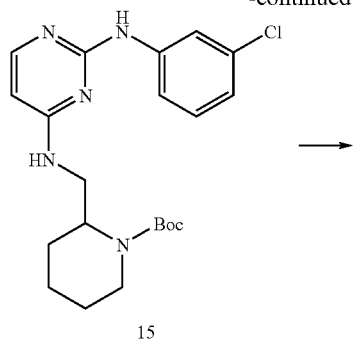

15

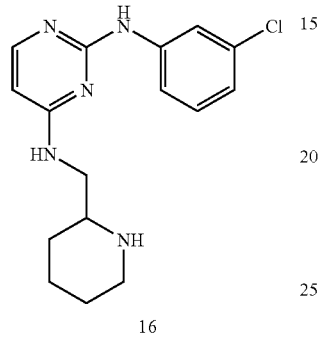

16

Example 5

N²-(3-Chlorophenyl)-N⁴-piperidin-2-ylmethyl-pyrimidine-2,4-diamine (16)

Preparation of 2-{[2-(3-chlorophenylamino)pyrimidin-4-ylamino]methyl}-piperidine-1-carboxylic acid tert-butyl ester (15): To a solution of 4-chloro-N-(3-chlorophenyl)pyrimidin-2-amine (300 mg, 1.25 mmol) and tert-butyl 2-(aminomethyl)-piperidine-1-carboxylate (540 mg, 2.50 mmol) in THF (10 mL) is added diisopropylethyl-amine (0.43 mL, 2.50 mmol). The reaction is heated at reflux for 18 hours and then cooled to room temperature. The crude reaction is partitioned between EtOAc and sat. NaHCO₃. The organic layer is dried (MgSO₄), concentrated in vacuo, and purified over silica (MeOH/CH₂Cl₂) to afford 268 mg (51% yield) of the desired compound: MS (ESI, pos. ion) m/z: 418 (M+1).

Preparation of N²-(3-chlorophenyl)-N⁴-piperidin-2-ylmethyl-pyrimidine-2,4-diamine (16): 2-{[2-(3-chlorophenylamino)pyrimidin-4-ylamino]methyl}-piperidine-1-carboxylic acid tert-butyl ester, 15, is dissolved in neat trifluoroacetic acid (3 mL) and stirred at room temperature for 3 hours. The reaction is concentrated in vacuo and the residue partitioned between EtOAc and sat. NaHCO₃. The organic layer is dried (MgSO₄), concentrated in vacuo, and purified over silica (MeOH/CH₂Cl₂) to afford 7 mg (7% yield) of the desired compound: $^1$H NMR (CDCl₃, 300 MHz) δ 1.50-1.63 (m, 1H), 1.70-1.92 (m, 4H), 1.95-2.10 (m, 2H), 2.88 (dt, J=12.0, 3.6 Hz, 1H), 3.30-3.40 (m, 1H), 3.52 (d, J=12.0 Hz, 1H), 3.61-3.70 (m, 1H), 3.87 (d, J=15.3 Hz, 1H) 6.01 (d, J=6.6 Hz, 1H), 7.02 (dt, J=7.5, 1.8 Hz, 1H), 7.22 (t, J=7.8 Hz, 1H), 7.25 (t, J=1.8 Hz, 1H), 7.75 (d, J=6.6 Hz, 1H), 7.96 (t, J=1.8 Hz, 1H); HRMS calcd for C₁₆H₂₀ClN₅, 318.1485 m/z (M+H)⁺; observed 318.1481 m/z.

The following are non-limiting examples of compounds which comprise first aspect of Category III of the present invention, the characterization of which will assist the formulator in establishing the chemical formulae of compounds which are not specifically exemplified herein. Alternatively, these compounds may also be synthesized by the synthetic route or methods described earlier in Scheme II.

N²-(3-Chlorophenyl)-N⁴-(1-methylpiperidin-2-ylmethyl)-pyrimidine-2,4-diamine: $^1$H NMR (CD₃OD, 300 MHz) δ 1.31-1.50 (m, 2H), 1.60-1.70 (m, 2H), 1.75-1.88 (m, 2H), 2.28-2.40 (m, 2H), 2.47 (s, 3H), 2.96 (dt, J=11.7, 2.7 Hz, 1H), 3.42-3.49 (m, 1H), 3.79 (d, J=12.6 Hz, 1H), 6.03 (d, J=6.3 Hz, 1H), 6.95 (ddd, J=8.1, 1.8, 0.9 Hz, 1H), 7.24 (t, J=7.8 Hz, 1H), 7.47 (d, J=8.1 Hz, 1H), 7.80 (d, J=5.7 Hz, 1H), 7.88 (t, J=1.8 Hz, 1H); HRMS calcd for C₁₇H₂₂ClN₅, 332.1642 m/z (M+H)⁺; observed 332.1631 m/z.

N²-(3-Chlorophenyl)-N⁴-piperidin-3-ylmethyl-pyrimidine-2,4-diamine: $^1$H NMR (CDCl₃, 300 MHz) δ 1.26-1.44 (m, 2H), 1.66-1.80 (m, 1H), 1.95-2.04 (m, 2H), 2.14-2.28 (m, 1H), 2.76 (t, J=12.0 Hz, 1H), 2.90 (dt, J=12.9, 3.3 Hz, 1H), 3.36-3.45 (m, 2H), 3.51 (dd, J=13.8, 6.0 Hz, 1H), 6.14 (d, J=6.6 Hz, 1H), 7.10 (d, J=7.2 Hz, 1H), 7.33 (t, J=7.8 Hz, 1H), 7.38 (d, J=7.2 Hz, 1H), 7.77 (d, J=6.6 Hz, 1H), 7.98 (s, 1H); HRMS calcd for C₁₆H₂₀ClN₅, 318.1485 m/z (M+H)⁺; observed 318.1483 m/z.

N²-(3-Chlorophenyl)-N⁴-(1-methylpiperidin-3-ylmethyl)-pyrimidine-2,4-diamine: $^1$H NMR (CD₃OD, 300 MHz) δ 1.00-1.17 (m, 1H), 1.58-1.73 (m, 1H), 1.78-1.85 (m, 1H), 1.85-2.20 (m, 5H), 2.38 (s, 3H), 2.95 (d, J=11.1 Hz, 1H), 3.08 (d, J=9.9 Hz, 1H), 3.30-3.39 (m, 1H), 6.00 (d, J=5.7 Hz, 1H), 6.95 (ddd, J=7.8, 1.8, 0.9 Hz, 1H), 7.24 (t, J=8.1 Hz, 1H), 7.38 (d, J=8.1 Hz, 1H), 7.77 (d, J=6.0 Hz, 1H), 8.09 (s, 1H); HRMS calcd for C₁₇H₂₂ClN₅, 332.1642 m/z (M+H)⁺; observed 332.1637 m/z.

N²-(3-Chlorophenyl)-N⁴-(1-methylpiperidin-4-yl-methyl)-pyrimidine-2,4-diamine hydrochloride salt. $^1$H NMR (CD₃OD, 300 MHz): δ 1.53-1.58 (m, 2H), 2.04-2.09 (m, 3H), 2.87 (s, 3H), 2.98-3.05 (m, 2H), 3.46-3.59 (m, 4H), 6.31 (d, 1H, J=7.2 Hz), 7.27-7.48 (m, 3H), 7.25 (d, 1H, J=7.2 Hz), 7.83 (s, 1H). MS (ESI, pos. ion) m/z: 332 (M+1).

N²-(3-Chlorophenyl)-N⁴-[2-(1-methylpyrrolidin-2-yl)-ethyl]-pyrimidine-2,4-diamine: HRMS calcd for C₁₇H₂₂N₅Cl, 332.1642 m/z (M+H)⁺; observed 332.1638 m/z.

N²-(3-Chlorophenyl)-N⁴-morpholin-2-ylmethyl-pyrimidine-2,4-diamine trifluoroacetate salt: $^1$H NMR (DMSO-d6, 300 MHz) δ 2.82-2.88 (m, 1H), 2.98-3.03 (m, 1H), 3.14-3.30 (m, 4H), 3.71 (t, J=12.0 Hz, 2H), 3.87-3.93 (m, 1H), 4.01 (d, J=12.3 Hz, 1H), 7.11 (d, J=8.1 Hz, 1H), 7.37 (t, J=7.8 Hz, 1H), 7.53 (d, J=8.1 Hz, 1H), 7.90 (d, J=6.0 Hz, 1H), 9.33 (s, 3H), 8.58 (bs, 1H), 9.07 (bs, 2H), 10.30 (bs, 1H); HRMS calcd for C₁₅H₁₈N₅ClO, 320.1278 m/z (M+H)⁺; observed 320.1277 m/z.

N²-(3-Chlorophenyl)-N⁴-(8-methyl-8-azabicyclo[3.2.1]oct-3-yl)-pyrimidine-2,4-diamine $^1$H NMR (CDCl₃, 300 MHz) δ 1.63-1.70 (m, 2H), 1.78-1.90 (m, 2H), 1.95-2.08 (m, 2H), 2.11-2.20 (m, 2H), 3.27-3.33 (m, 2H), 4.56-4.63 (m, 1H), 5.85 (d, J=5.7 Hz, 1H), 6.95 (bs, 1H), 6.98 (dd, J=7.5, 0.6 Hz, 1H), 7.23 (t, J=7.8 Hz, 1H), 7.35 (dd, J=8.1, 1.2 Hz, 1H), 7.86 (t, J=1.8 Hz, 1H), 7.90 (d, J=5.1 Hz, 1H); HRMS calcd for C₁₈H₂₂N₅Cl, 344.1642 m/z (M+H)⁺; observed 344.1644 m/z.

N²-(3-Chloro-phenyl)-N⁴-(2,2,6,6-tetramethyl-piperidin-4-yl)-pyrimidine-2,4-diamine: (ESI, neg. ion) m/z: 395 (M−1).

N²-(3-Chloro-phenyl)-N⁴-piperidin-4-ylmethyl-pyrimidine-2,4-diamine.

N²-(3-Chloro-phenyl)-N⁴-(1-isopropyl-piperidin-3-ylmethyl)-pyrimidine-2,4-diamine: (ESI, pos. ion) m/z: 360 (M+1).

The second aspect of Category III relates to R units which comprise a chiral carbon atom. Scheme VI herein below and the following examples illustrate this second aspect of Category III of the present invention.

Scheme VI

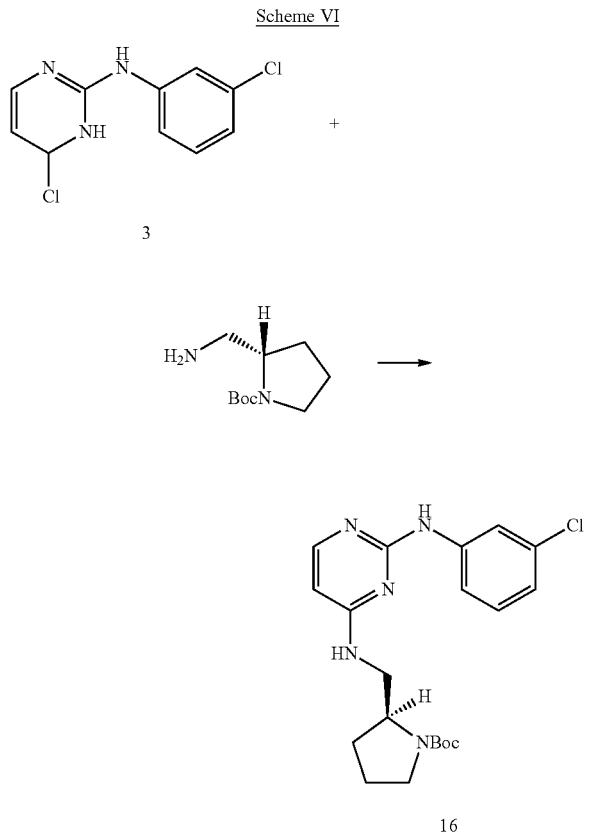

Reagents and conditions (a): DIPEA, THF, reflux, 18 h

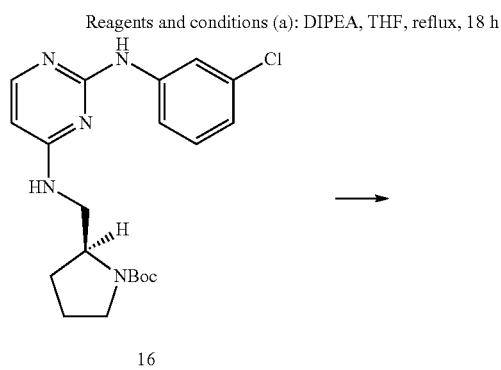

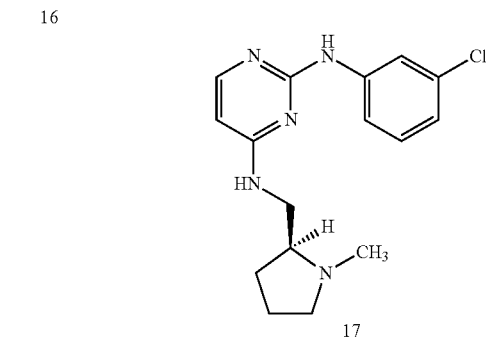

Reagents and conditions (b): LAH, THF, rt, 24 h

Example 6

N²-(3-Chlorophenyl)-N⁴-{[(2S)-1-methylpyrrolidin-2-yl]methyl}pyrimidine-2,4-diamine (17)

Preparation of tert-butyl (2S)-2-[({2-[(3-chlorophenyl)amino]pyrimidin-4-yl}amino)methyl]pyrrolidine-1-carboxylate (16): To a solution of 4-chloro-N-(3-chlorophenyl)pyrimidin-2-amine, 3, (300 mg, 1.25 mmol) and tert-butyl (2S)-2-(aminomethyl)pyrrolidine-1-carboxylate (500 mg, 2.50 mmol) in THF (10 mL) is added diisopropylethylamine (0.43 mL, 2.50 mmol). The reaction was heated at reflux for 18 hours and then cooled to room temperature. The crude reaction is then partitioned between EtOAc and sat. NaHCO₃. The organic layer is dried (MgSO₄), concentrated in vacuo, and purified over silica (MeOH/CH₂Cl₂) to afford 160 mg (32% yield) of the desired product: MS (ESI, pos. ion) m/z: 404 (M+1).

Preparation of N²-(3-chlorophenyl)-N⁴-{[(2S)-1-methylpyrrolidin-2-yl]methyl}pyrimidine-2,4-diamine (17): To a solution of tert-butyl (2S)-2-[({2-[(3-chlorophenyl)amino]pyrimidin-4-yl}amino)methyl]pyrrolidine-1-carboxylate (160 mg, 0.40 mmol) in THF (3 mL) is added lithium aluminum hydride (2 M in THF, 0.6 mL, 1.19 mmol). The reaction is stirred at room temperature for 24 hours and then quenched with NaOH (1 N, 2 mL) and stirred for an additional hour. The reaction solution is partitioned between EtOAc and sat. NaHCO₃. The organic layer is dried (MgSO₄), concentrated in vacuo, and purified over silica (MeOH/CH₂Cl₂) to afford 22 mg (17% yield) of the desired compound: ¹H NMR (CDCl₃, 300 MHz) δ 1.58-1.68 (m, 1H), 1.70-1.83 (m, 2H), 1.99-2.11 (m, 1H), 2.29 (q, J=8.7 Hz, 1H), 2.43 (s, 3H), 2.48-2.58 (m, 1H), 3.04-3.12 (m, 1H), 3.29 (t, J=6.3 Hz, 1H), 3.77 (d, J=11.7 Hz, 1H), 6.01 (d, J=6.0 Hz, 1H), 6.94 (ddd, J=8.1, 2.4, 0.9 Hz, 1H), 7.23 (t, J=7.8 Hz, 1H), 7.49 (ddd, J=8.4, 2.1, 0.9 Hz, 1H), 7.78 (d, J=6.0 Hz, 1H), 7.89 (t, J=2.1 Hz, 1H); HRMS calcd for C₁₆H₂₀ClN₅, 318.1485 m/z (M+H)⁺; observed 318.1491 m/z.

The (2R) enantiomer can be prepared in the same manner as described herein above.

Scheme VII

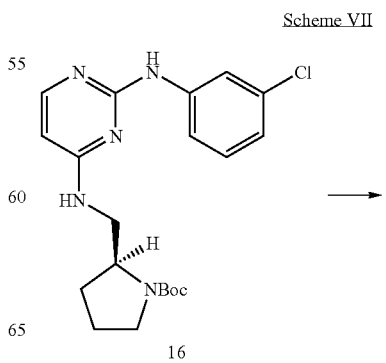

-continued

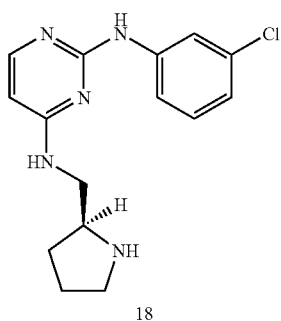

18

Reagents and conditions (a): TFA, CH₂Cl₂, rt, 24 h

Example 7

N²-(3-Chlorophenyl)-N⁴-[(2S)-pyrrolidin-2-ylmethyl]pyrimidine-2,4-diamine (18)

Preparation of N²-(3-chlorophenyl)-N⁴-[(2S)-pyrrolidin-2-ylmethyl]pyrimidine-2,4-diamine (18): To a solution of tert-butyl (2S)-2-[({2-[(3-chlorophenyl)amino]-pyrimidin-4-yl}amino)methyl]pyrrolidine-1-carboxylate, 15, (150 mg, 0.37 mmol) in CH₂Cl₂ (5 mL) is added trifluoroacetic acid (3 mL). The reaction is stirred at room temperature for 24 hours then partitioned between EtOAc and sat. NaHCO₃. The organic layer is dried (MgSO₄), concentrated in vacuo, and purified over silica (MeOH/CH₂Cl₂) to afford 36 mg (32% yield) of the desired material: ¹H NMR (CDCl₃, 300 MHz) δ 1.43-1.56 (m, 1H), 1.70-1.91 (m, 2H), 1.93-2.06 (m, 1H), 2.97 (t, J=6.9 Hz, 2H), 3.16-3.29 (m, 1H), 3.41-3.52 (m, 1H), 3.54-3.66 (m, 1H), 5.71 (t, J=5.1 Hz, 1H), 5.91 (d, J=6.0 Hz, 1H), 6.96 (ddd, J=7.8, 5.7, 0.9 Hz, 1H), 7.20 (t, J=8.1 Hz, 1H), 7.26-7.32 (m, 1H), 7.57 (bs, 1H), 7.91 (d, J=5.7 Hz, 1H), 7.99 (s, 1H); HRMS calcd for C₁₅H₁₈ClN₅, 304.1329 m/z (M+H)⁺; observed 304.1319 m/z.

Scheme VIII

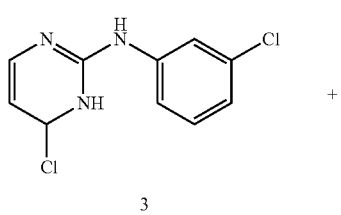

3

+

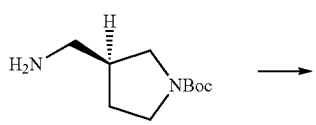

-continued

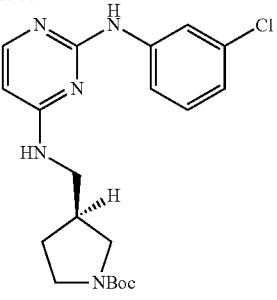

19

Reagents and conditions (a): DIPEA, THF, reflux, 18 h

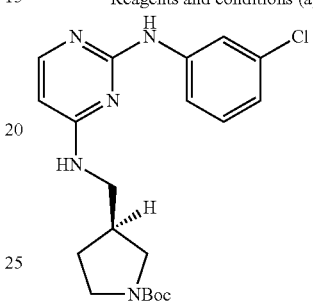

19

→

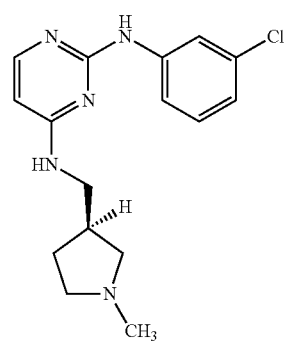

20

Reagents and conditions (b): LAH, THF, rt, 24 h

Example 8

N²-(3-Chlorophenyl)-N⁴-{[(3S)-1-methylpyrrolidin-3-yl]methyl}pyrimidine-2,4-diamine (20)

Preparation of tert-butyl (3S)-3-[({2-[(3-chlorophenyl)amino]pyrimidin-4-yl}amino)methyl]pyrrolidine-1-carboxylate (19): To a solution of 4-chloro-N-(3-chlorophenyl)pyrimidin-2-amine (500 mg, 2.08 mmol) and tert-butyl (3S)-3-(aminomethyl)pyrrolidine-1-carboxylate (625 mg, 3.12 mmol) in THF (10 mL) is added diisopropylethylamine (0.73 mL, 4.16 mmol). The reaction is heated at reflux for 18 hours and then cooled to room temperature. The crude reaction is partitioned between EtOAc and sat. NaHCO₃. The organic layer is dried (MgSO₄), concentrated in vacuo, and purified over silica (MeOH/CH₂Cl₂) to afford 356 mg (42% yield) of the desired compound: MS (ESI, pos. ion) m/z: 404 (M+1).

Preparation of N²-(3-chlorophenyl)-N⁴-{[(3S)-1-methylpyrrolidin-3-yl]methyl}pyrimidine-2,4-diamine (20): To a solution of tert-butyl (3S)-3-[({2-[(3-chlorophenyl)-amino]pyrimidin-4-yl}amino)methyl]pyrrolidine-1-carboxylate, 19, (356 mg, 0.88 mmol) in THF (2 mL) is added lithium aluminum hydride (2 M in THF, 1.32 mL, 2.64 mmol). The reaction is heated to 50° C. for 3 days, cooled to room temperature, quenched with NaOH (1 N, 2 mL) and stirred for an additional hour. The reaction mixture is extracted with EtOAc (2×25 mL) and the combined organic layers are dried (MgSO$_4$), concentrated in vacuo, and purified over silica (MeOH/CH$_2$Cl$_2$) to afford 190 mg (68% yield) of the desired product: $^1$H NMR (DMSO, 300 MHz) δ 1.40-1.50 (m, 1H), 1.86-1.96 (m, 1H), 2.23 (s, 3H), 2.25-2.33 (m, 1H), 2.34-2.41 (m, 1H), 2.42-2.54 (m, 5H), 5.96 (d, J=5.7 Hz, 1H), 6.89 (dt, J=7.5, 0.9 Hz, 1H), 7.22 (t, J=8.4 Hz, 1H), 7.39 (bs, 1H), 7.57 (d, J=7.8 Hz, 1H), 7.74-7.85 (m, 2H), 8.15 (bs, 1H), 9.21 (s, 1H); HRMS calcd for C$_{16}$H$_{20}$ClN$_5$, 318.1485 m/z (M+H)$^+$; observed 318.1485 m/z.

In some instances the formulator will find it necessary to synthesize various R units encompassed within the scope of the present invention. Schemes IX and X and Examples 9 and 10 herein below disclose examples of compounds having substituted heterocyclic units for R.

Scheme IX

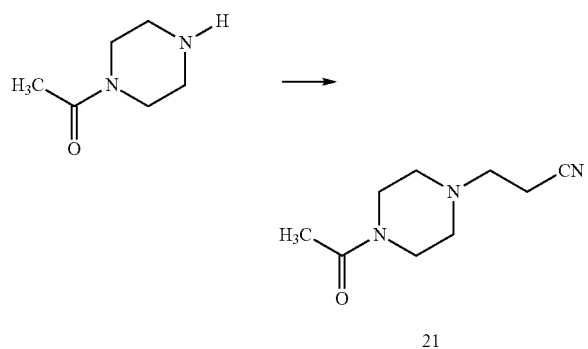

Reagents and conditions: (a) CH$_2$=CHCN, MeOH, 0° C. to rt.

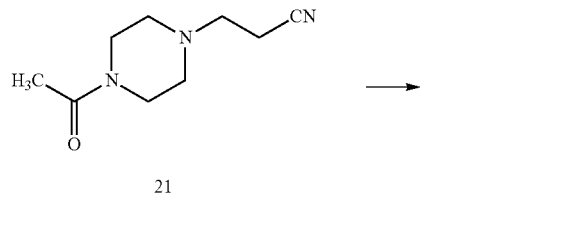

Reagents and conditions: (b) H$_2$/Raney Ni, NH$_3$, NH$_4$OH, EtOH; rt, 18 hr.

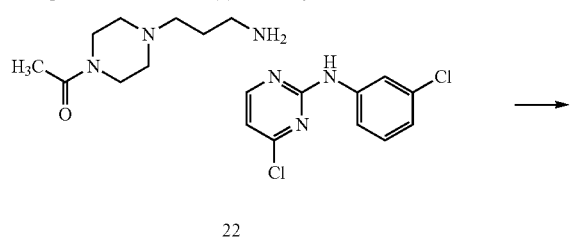

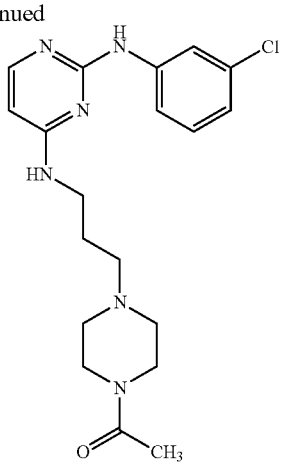

Reagents and conditions: (c) THF, DIPEA; reflux, 12 hr.

Example 9

1-(4-{3-[2-(3-Chloro-phenylamino)-pyrimidin-4-ylamino]-propyl}-piperazin-1-yl)-ethanone (23)

Preparation of 3-(4-acetylpiperazin-1-yl)propanenitrile (21): To 1-(piperazin-1-yl)ethanone (5 g, 39 mmol) in MeOH (50 mL) at 0° C. is added acrylonitrile (2.57 mL, 39 mmol) in one portion. The resulting reaction is stirred for 12 hours while allowing the reaction to warm to room temperature. The reaction mixture is concentrated in vacuo and the resulting residue diluted with 5 mL of water and extracted with EtOAc (3×25 mL). The combined organic layers are dried (MgSO$_4$) and concentrated in vacuo. The residue is purified over silica (2% MeOH in CH$_2$Cl$_2$) to afford 6.4 g (91% yield) of the desired compound. $^1$H NMR (CDCl$_3$, 300 MHz) δ2.08 (s, 3H), 2.46 (t, J=5.1 Hz, 2H), 2.51-2.53 (m, 4H), 2.71 (t, J=6.9 Hz, 2H), 3.48 (t, J=5.1 Hz, 2H), 3.26 (t, J=5.1 Hz, 2H). MS (ESI, pos. ion) m/z: 182 (M+1).

Preparation of 1-(4-(3-aminopropyl)piperazin-1-yl)ethanone (22): A Parr hydrogenation vessel is charged with ethanol (200 mL) and purged with nitrogen for 10 minutes. Raney nickel catalyst (20 g), 3-(4-acetylpiperazin-1-yl)propanenitrile, 21, (4.12 g, 22.64 mmol) dissolved in ethanol (138 mL), and NH$_4$OH (98 mL) are added. The flask is then cooled to 0° C. and purged with ammonia gas for 15 minutes. Hydrogen gas is then introduced and the reaction vessel shaken for 18 hours at 40 psi of hydrogen. Once complete, the reaction solution is filtered through celite, and the solute concentrated in vacuo and used without further purification. MS (ESI, pos. ion) m/z: 186 (M+1).

Preparation of 1-(4-{3-[2-(3-chloro-phenylamino)-pyrimidin-4-ylamino]-propyl}-piperazin-1-yl)-ethanone (23): To 4-chloro-N-(3-chlorophenyl)pyrimidin-2-amine (0.5 g, 2.09 mmol) in THF (13 mL) is added DIPEA (0.73 mL, 4.18 mmol) followed by 1-(4-(3-aminopropyl)-piperazin-1-yl) ethanone, 22, (0.77 g, 4.18 mmol). The resulting mixture is refluxed for 12 hours after which the reaction mixture is cooled to room temperature and the solvent removed in vacuo. To the resulting residue is added water (50 mL) and the solution is washed with EtOAc (3×100 mL). The combined organic layers are dried (MgSO$_4$) and concentrated in vacuo. The residue which is obtained is purified over silica (10% MeOH in CH$_2$Cl$_2$) to afford 0.173 g (10% yield) of the desired compound. $^1$H NMR (DMSO-d$_6$, 300 MHz) δ1.67-1.75 (m, 2H), 1.97 (s, 3H), 2.27-2.40 (m, 6H), 3.37-3.42 (m, 6H), 5.96 (d, J=6.0 Hz, 1H), 6.87 (d, J=8.1 Hz, 1H), 7.21 (t, J=8.1 Hz, 1H), 7.28 (bs, 1H), 7.58 (d, J=7.2 Hz, 1H), 7.80 (bs, 1H), 8.13 (bs, 1H), 9.19 (s, 1H). MS (ESI, pos. ion) m/z: 389 (M+1). HRMS calcd for $C_{19}H_{25}ClN_6O$, 389.1857 m/z (M+H)$^+$; observed 389.1851 m/z.

Scheme X

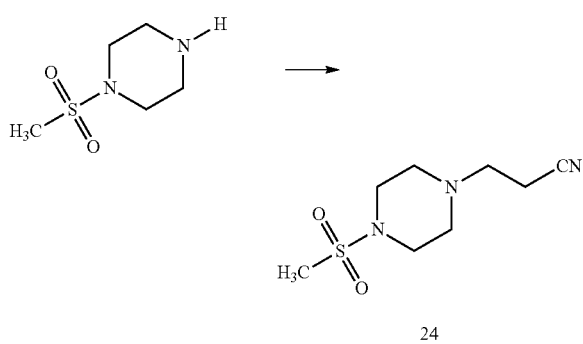

24

Reagents and conditions: (a) $CH_2$=CHCN, MeOH, 0° C. to rt.

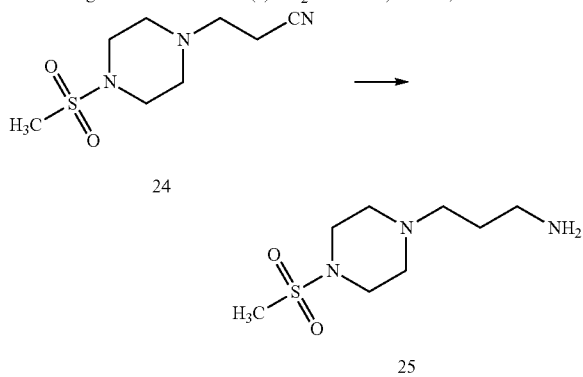

Reagents and conditions: (b) $H_2$/Raney Ni, $NH_3$, $NH_4OH$, EtOH; rt, 18 hr.

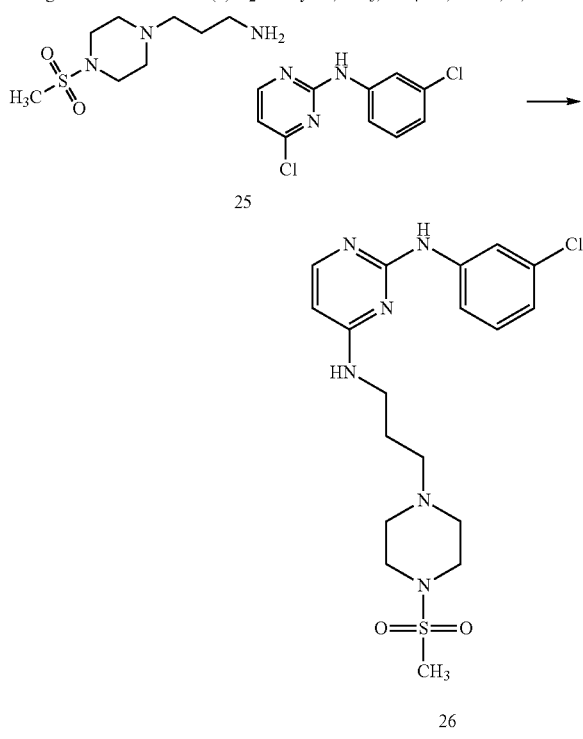

Reagents and conditions: (c) THF, DIPEA; reflux, 12 hr.

Example 10

$N^2$-(3-Chloro-phenyl)-$N^4$-[3-(4-methanesulfonyl-piperazin-1-yl)-propyl]-pyrimidine-2,4-diamine (26)

Preparation of 3-(4-(methylsulfonyl)piperazin-1-yl)propanenitrile (24): To 1-(methylsulfonyl)piperazine (1 g, 6.09 mmol) in MeOH (11 mL) at 0° C. is added acrylonitrile (0.402 mL, 6.09 mmol). The reaction mixture is concentrated in vacuo and the resulting residue diluted with 5 mL of water and extracted with EtOAc (3×25 mL). The combined organic layers are dried ($MgSO_4$) and concentrated in vacuo. The residue is purified over silica (2% MeOH in $CH_2Cl_2$) to afford 1.1 g (99% yield) of the desired compound. $^1$H NMR ($CDCl_3$, 300 MHz) δ2.56 (t, J=6.9 Hz, 2H), 2.66 (t, J=4.8 Hz, 4H), 2.76 (t, J=6.9 Hz, 2H), 2.81 (s, 3H), 3.30 (t, J=4.8 Hz, 4H). MS (ESI, pos. ion) m/z: 218 (M+1).

Preparation of 3-(4-(methylsulfonyl)piperazin-1-yl)propan-1-amine (25): A Parr hydrogenation vessel is charged with ethanol (200 mL) and purged with nitrogen for 10 minutes. Raney nickel catalyst (4.5 g), 3-(4-(methylsulfonyl)piperazin-1-yl)propanenitrile, 24, (1.1 g, 5.07 mmol) dissolved in ethanol (50 mL), and $NH_4OH$ (98 mL) are added. The flask is then cooled to 0° C. and purged with ammonia gas for 15 minutes. Hydrogen gas is then introduced and the reaction vessel shaken for 18 hours at 40 psi of hydrogen. Once complete, the reaction solution is filtered through celite, and the solute concentrated in vacuo and used without further purification. $^1$H NMR (MeOD, 300 MHz) δ 1.70 (m, 2H), 2.48 (t, J=7.2 Hz, 2H), 2.59 (t, J=4.2 Hz, 4H), 2.71 (t, J=6.6 Hz, 2H), 2.86 (s, 3H), 3.25 (t, J=4.8, 4H).

Preparation of $N^2$-(3-Chloro-phenyl)-$N^4$-[3-(4-methanesulfonyl-piperazin-1-yl)-propyl]-pyrimidine-2,4-diamine (26): To 4-chloro-N-(3-chlorophenyl)pyrimidin-2-amine (0.2 g, 0.837 mmol) in THF (10 mL) is added DIPEA (0.29 mL, 1.67 mmol) followed by 3-(4-(methylsulfonyl)piperazin-1-yl)propan-1-amine, 25, (0.0.369 g, 1.67 mmol). The resulting mixture is refluxed for 12 hours after which the reaction mixture is cooled to room temperature and the solvent removed in vacuo. To the resulting residue is added water (50 mL) and the solution is washed with EtOAc (3×100 mL). The combined organic layers are dried ($MgSO_4$) and concentrated in vacuo. The residue which is obtained is purified over silica (10% MeOH in $CH_2Cl_2$) to afford 0.129 g (50% yield) of the desired compound. $^1$H NMR (DMSO-$d_6$, 300 MHz) δ1.71 (m, 2H), 2.39-2.45 (m, 6H), 2.84 (s, 3H), 3.08 (m, 4H), 3.38 (m, 2H), 5.96 (d, J=5.7 Hz, 1H), 6.87 (d, J=7.8 Hz, 1H), 7.18-7.27 (m, 2H), 7.58 (d, J=7.5 Hz, 1H), 7.81 (bs, 1H), 8.12 (bs, 1H), 9.18 (s, 1H). MS (ESI, pos. ion) m/z: 425 (M+1). HRMS calcd for $C_{18}H_{25}ClN_6O_2S$, 425.1526 m/z (M+H)$^+$; observed 425.1512 m/z.

The compounds of the present invention are inhibitors of Protein Kinase C-alpha (PKC-α), therefore, they are PKC-α inhibitors which are capable of improving myocardial contraction and relaxation performance and slow the progression of heart failure. Certain exemplified compounds may also potentially inhibit additional isoforms of conventional PKC, such as PKC-β or PKC-γ. This is not undesirable and can lead to increased pharmacological effects.

The level of disease, for example, the relative degree of heart failure due to PKC-α activity will vary from patient to patient and be predicated by other exacerbating circumstances, inter alia, presence of other disease conditions (diabetes, high blood pressure, and the like) or patients may suffer from other conditions such as obesity. Therefore, the formulator may be required to employ differing levels or amounts of the compounds described herein to obtain a therapeutic level. The formulator can determine this amount by any of the known testing procedures known to the artisan.

Formulations

The present invention also relates to compositions or formulations which comprise the PKC-α inhibitors according to the present invention. In general, the compositions of the present invention comprise:
a) an effective amount of one or more 2-arylamino-4-(heterocyclic)aminopyrimidines or salts thereof according to the present invention which are effective for inhibiting PKC-α; and
b) one or more excipients.

For the purposes of the present invention the term "excipient" and "carrier" are used interchangeably throughout the description of the present invention. One aspect of excipient and carrier relate to their definition in terms of a medicament, said terms are defined in that respect as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Non-limiting examples of compositions according to the present invention include:
a) from about 0.001 mg to about 1000 mg of one or more PKC-α inhibitors according to the present invention; and
b) one or more excipient.

Another embodiment according to the present invention relates to the following compositions:
a) from about 0.01 mg to about 100 mg of one or more PKC-α inhibitors according to the present invention; and
b) one or more excipient.

A further embodiment according to the present invention relates to the following compositions:
a) from about 0.1 mg to about 10 mg of one or more PKC-α inhibitors according to the present invention; and
b) one or more excipient.

The term "effective amount" as used herein means "an amount of one or more PKC-α inhibitors, effective at dosages and for periods of time necessary to achieve the desired result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present invention can be administered as frequently as necessary to achieve a therapeutic amount.

Method of Use

The present invention also relates to a method for improving cardiac contraction/relaxation parameters in heart failure patients and/or attenuating adverse cardiac remodeling and prevent or slow the progression of worsening heart failure. The present method comprises the step of administering to a human or higher mammal an effective amount of a composition comprising one or more of the PKC-α inhibitors according to the present invention.

The present method comprised a method for treating or preventing a disease or medical condition selected from diabetes, numerous forms of cancer, microalbinuria, endothelial dysfunction, cerebrovascular disease, stroke, coronary heart disease, cardiovascular disease and sequela (e.g. arrhythmia, sudden death, increased infarct size, congestive heart failure, angina), myocardial ischemic states, hypertension, lipid disorders, ischemia-reperfusion injury, atherosclerosis, peripheral artery/vascular disease, microvascular complications of diabetes (neuropathy, nephropathy, retinopathy), restenosis, renal disease, blood coagulation disorders, inflammatory diseases, cardiac hypertrophy, dilated cardiomyopathy, ischemic injury and suboptimal mitogen stimulation said method comprised of the steps of administering to a patient in need thereof a therapeutic amount of a PKC-α inhibitor as disclosed herein.

The present invention also relates to the use of the 2-arylamino-4-(heterocyclic)-amino-pyrimidines or salts thereof, according to the present invention in the manufacture of a medicament for the treatment of heart disease wherein inhibition of PKC-α provides a benefit.

Procedures

Assessment of PKC-α Inhibitory Activity

Measurement of PKCα enzyme activity is performed using full-length human PKCα enzyme (Upstate Biotechnology) at a final concentration of 0.12 μg/ml in a kinase assay buffer (0.09 mg/ml bovine serum albumin (BSA), 210 μM ethylenediaminetetraacetic acid (EDTA), 360 μM $CaCl_2$, 1 mM Tris-HCl, pH=7.5, 0.5 mM $MgCl_2$, 0.015 mg/ml phosphatidylserine and 0.015 mg/ml diacylglycerol). The reaction is initiated by addition of adenosine triphosphate (ATP; final concentration 45 μM) and a peptide substrate consisting of amino acids 28-43 (Ala-Ala-Lys-Ile-Gln-Ala-Ser-Phe-Arg-Gly-His-Met-Ala-Arg-Lys-Lys) of neurogranin (Promega; final concentration 22 μM). After a 30 minute incubation at 24° C. the reaction is terminated by adding 5 μL of the reaction mixture into 50 μL of MALDI matrix solution (5 mg/ml α-cyano-4-hydroxycinnamic acid in 50% Acetonitrile/$H_2O$, 0.1% TFA, 5 mM ammonium phosphate). Two microliters of the stopped reaction mixture is transferred onto a MALDI-TOF mass spectrometer target plate.

All spectra are collected on an Applied Biosystems 4700 Proteomics Analyzer MALDI-TOF MS equipped with a Nd:YAG laser (355 nm, 3 ns pulse width, 200 Hz repetition rate) in negative ion reflector mode. The system is operated with 4700 Explorer software, version 3.0. Automated acquisition parameters are adjusted to capture and average only those individual spectra within defined success criteria. Specifically, signal intensities for the substrate peptide are set to a minimum threshold of 3000 counts and a maximum intensity of 65,000 counts. This ensured that neither null spectra nor saturated spectra are averaged into the final readout. Between 1000 and 1500 laser shots are averaged for each sample. Data are collected in triplicate from 3 successive days to capture the maximum variability related to preparation of enzyme reaction, transfer of samples to MALDI target plates, data collection, and data extraction.

The isotope cluster areas for each peptide substrate and product peaks are extracted into a Microsoft Excel worksheet from the 10×10 array of spectral data simultaneously using the automated analysis function provided within the 4700 Explore software. The isotope cluster area is defined by the software algorithm based on the molecular weight and the general elemental composition of the peptides. The percent conversion (% C) of substrate to product is calculated as the cluster area of the product (P) divided by the sum of the cluster areas of the substrate (S) and the product multiplied by 100 as represented by the following equation:

$$\% \ C = \frac{P}{P+S} \times 100.$$

For dose-dependent inhibition studies, the inhibition is plotted as a % Maximal Activity (% MA). Equation one is a measure of the ratio of product to substrate then solving for the % C. However, to measure inhibition of the enzyme activity, one must measure the degree to which that activity (% C) is curtailed. Thus the dose-dependant inhibition data is plotted as % MA where the maximal activity is the % C measured in control reactions with no inhibitor as represented by the following equation:

$$\% \ MA = \frac{\% \ C \text{ with inhibitor}}{\% \ C \text{ with no inhibitor}} \times 100.$$

Evaluation of PKCα Inhibitors in Cardiomyocytes

Determination of PKCα activity in cells is determined using murine HL-1 atrial cardiac muscle cells. On day 1, HL-1 cells are plated at 18,000 cells/well in a 96-well tissue culture plate. Cells are cultured in 0.1 ml Claycomb growth medium (without norepinephrine) supplemented with 10% fetal bovine serum, 200 mM glutamine and 1% antibiotic/antimycotic. On day 2, cells are washed 1× with 100 µl of phosphate buffered saline (PBS) and the medium is replaced with 100 µl serum free Claycomb medium supplemented with 200 mM glutamine. For compound testing, the medium is removed and replaced with serum free Claycomb medium supplemented with 200 mM glutamine containing different concentrations of compound at a final volume of 50 µl. Compounds are dissolved in 100% dimethylsulfoxide (DMSO) and final DMSO concentrations are maintained at 0.5%. Plates are then incubated for 30 minutes at 37° C. in a 5% $CO_2$ incubator. The medium is then removed and the plates are rinsed 1× with ice-cold 100 µl PBS. The PBS is removed and replaced with 10 µl of ice-cold lysis buffer consisting of B-PERII detergent (Pierce) diluted 1:1 in distilled water and including a final concentration of 0.3% β-mercaptoethanol, 50 µg/ml phenylmethylsulfonylfluoride (PMSF) 10 mM benzamidine, 10 nM okadaic acid, 20 µg/ml leupeptin and 20 µg/ml soybean trypsin inhibitor. The plates are gently mixed for 10-20 minutes at 4° C. Next, 90 µl of coactivation buffer, consisting of 0.1 mg/ml BSA, 250 µM EDTA, 400 µM $CaCl_2$, is added to each well. Twenty-five microliters of the cell lysate/coactivation buffer solution is removed from each well and the enzyme activity measured by addition of 25 µl of substrate solution, consisting of 0.1 mg/ml bovine serum albumin, 235 µM EDTA, 400 µM $CaCl_2$, 1 mM Tris-HCl, pH=7.5, 0.5 mM $MgCl_2$, 0.015 mg/ml phosphatidylserine and 0.015 mg/ml diacylglycerol, 20 µM ATP and 2 µM of an octapeptide fragment of the EGF receptor (Arg-Lys-Arg-Thr-Leu-Arg-Arg-Leu). After a 30 minute incubation at 24° C. the reaction is terminated by adding 5 µL of the reaction mixture into 50 µL of MALDI matrix solution (5 mg/ml α-cyano-4-hydroxycinnamic acid in 50% Acetonitrile/$H_2O$, 0.1% TFA, 5 mM ammonium phosphate). Two microliters of the stopped reaction mixture is transferred onto a MALDI-TOF mass spectrometer target plate. Dose-dependent inhibition is measured by mass spectrometry as % maximal activity as described above for the isolated PKCα inhibition assays.

In Vivo Evaluation of PKCα Inhibitors in the Anesthetized Rat

Selected PKCα inhibitors are evaluated in rats with acute heart failure (HF) after myocardial infarction (MI) for effects on cardiac contractility and hemodynamics. Male, Sprague-Dawley rats are anesthetized with isoflurane, intubated, placed on ventilators and maintained at a surgical plane of anesthesia during the course of the experiment. The animals are instrumented, for the measurement of left ventricular function (+dP/dt, LVDP), arterial blood pressure, and the ECG is monitored for the incidence of arrhythmias. A thoracotomy is performed at the fourth intercostal space to visualize the heart, the pericardium is opened and a suture is placed around the left anterior descending (LAD) coronary artery approximately 3-4 mm from its origin. When hemodynamic values are stabilized, the LAD is permanently ligated to induce a myocardial infarction. Severe arrhythmia are treated with the administration of lidocaine. Typically, cardiac function stabilized approximately 40-60 min after ligation and baseline hemodynamic values are measured. $N^2$-(3-chlorophenyl)-$N^4$-(3-(dimethylamino)propyl)pyrimidine-2,4-diamine, 100 and 300 nmol/kg/min for 10 min each dose, and hemodynamic parameters are measured after each dose. The effects of treatment are normalized to pre-treatment baseline values and expressed as a percentage. Statistical significance (p<0.05) is evaluated using one-way ANOVA and Dunnett's multiple comparison test.

In Vivo Evaluation of PKCα Inhibitors in the Anesthetized Rat

Selected PKCα inhibitors are evaluated in rats with myocardial infarction (MI) for effects on cardiac contractility and hemodynamics.

Male, Sprague-Dawley or Lewis rats weighing between 225-500 gm are anesthetized with isoflurane and an MI is induced as follows. A thoracotomy is performed at the fourth intercostal space to visualize the heart, the pericardium is opened and a suture is placed around the left anterior descending (LAD) coronary artery approximately 3-4 mm from its origin. When hemodynamic values are stabilized, the LAD is permanently ligated to induce a myocardial infarction. Severe arrhythmias are treated with the administration of lidocaine. Typically, cardiac function stabilized approximately 40-60 min after ligation and baseline hemodynamic values are measured.

The effects of inhibitors on cardiac contractility and hemodynamics are evaluated in MI rats as follows. The animals are anesthetized with isoflurane. A femoral artery is isolated and cannulated for the measurement of systemic blood pressure. A jugular vein is isolated and cannulated for the intravenous infusion of inhibitor. The right carotid artery is isolated and a Millar conductance catheter is inserted to the left ventricle (LV) of the heart. The LV systolic pressure, end-diastolic pressure, +dP/dt$_{max}$, −dP/dt$_{min}$, and heart rate are derived from the LV pressure waveform. Mean arterial blood pressure is derived from the systemic blood pressure waveform. Data are recorded continuously and derived using computerized data acquisition software (Notocord or Powerlab).

After a period of stabilization, PKC-α inhibitors are infused at the following infusion doses in MI rats: 10, 30, 100, 300 and 1000 nmol/kg/min. The infusion of each dose is allowed to run for at least five minutes. At the end of the test infusions, 5.0 μg/kg/min of dobutamine is infused. The effects of treatment are normalized to pretreatment baseline values and expressed as a percentage. Statistical significance (p<0.05) is evaluated using a one-way ANOVA and Dunnett's multiple comparison test.

Table VI provides non-limiting examples of PKC-α IC$_{50}$ values for representative compounds of the present invention.

TABLE VI

| Compound | PKC-α IC$_{50}$ (nM) |
|---|---|
| N$^2$-(3-Chlorophenyl)-N$^4$-(3-morpholin-4-yl-propyl)-pyrimidine-2,4-diamine | 2 |
| N$^2$-(3-Chlorophenyl)-N$^4$-[3-(4-methylpiperazin-1-yl)-propyl]-pyrimidine-2,4-diamine | 5 |
| 1-{3-[2-(3-Chlorophenylamino)-pyrimidin-4-ylamino]-propyl}-pyrrolidin-2-one | 710 |
| N$^2$-[3-Trifluoromethyl-phenyl]-N$^4$-(3-pyrrolidin-1-yl-propyl)-pyrimidine-2,4-diamine | 0.5 |
| N$^4$-(3-Pyrrolidin-1-yl-propyl)-N$^2$-[3-methylphenyl]-pyrimidine-2,4-diamine | 40 |
| N$^4$-(3-Pyrrolidin-1-yl-propyl)-N$^2$-[3-methoxyphenyl]-pyrimidine-2,4-diamine | 16 |
| N$^2$-(3-Chlorophenyl)-N$^4$-[2-(1-methylpyrrolidin-2-yl)-ethyl]-pyrimidine-2,4-diamine | 0.4 |
| N$^2$-(3-Chlorophenyl)-N$^4$-morpholin-2-ylmethyl-pyrimidine-2,4-diamine | 23 |
| N$^2$-(3-Chlorophenyl)-N$^4$-(3-pyrrolidin-1-yl-propyl)-pyrimidine-2,4-diamine | 3 |
| N$^2$-(3-Chlorophenyl)-N$^4$-(1-methylpiperidin-4-ylmethyl)-pyrimidine-2,4-diamine | 30 |
| N$^2$-(3-Chlorophenyl)-N$^4$-(8-methyl-8-azabicyclo[3.2.1]oct-3-yl)-pyrimidine-2,4-diamine | 4 |
| N$^2$-(4-(Benzyloxy)-3-chlorophenyl)-N$^4$-(3-pyrrolidin-1-yl-propyl)-pyrimidine-2,4-diamine | 40 |
| N$^2$-(3-Nitrophenyl)-N$^4$-(3-morpholin-4-yl-propyl)-pyrimidine-2,4-diamine | 1 |
| N$^2$-(3-Nitrophenyl)-N$^4$-(3-pyrrolidin-1-yl-propyl)-pyrimidine-2,4-diamine | 2 |
| N$^2$-(3-Bromophenyl)-N$^4$-(3-morpholin-4-yl-propyl)-pyrimidine-2,4-diamine | 1 |
| N$^2$-(3-Isopropylphenyl)-N$^4$-(3-morpholin-4-yl-propyl)-pyrimidine-2,4-diamine | 80 |
| N$^2$-Biphenyl-3-yl-N$^4$-(3-morpholin-4-yl-propyl)-pyrimidine-2,4-diamine | 3 |
| N$^2$-(3,5-Bis-trifluoromethyl-phenyl)-N$^4$-(3-morpholin-4-yl-propyl)-pyrimidine-2,4-diamine | 21 |
| N$^2$-[3-(Pyridin-3-yl)-phenyl]-N$^4$-(3-morpholin-4-yl-propyl)-pyrimidine-2,4-diamine | 28 |
| N-{3-[4-(3-Morpholin-4-yl-propylamino)-pyrimidin-2-ylamino]-phenyl}-benzenesulfonamide | 23 |
| N$^2$-[3-(N,N-dimethylamino)-phenyl]-N$^4$-(3-morpholin-4-yl-propyl)-pyrimidine-2,4-diamine | 53 |
| N$^2$-(3-Fluorophenyl)-N$^4$-(3-morpholin-4-yl-propyl)-pyrimidine-2,4-diamine | 64 |
| N$^2$-(3-Nitro-biphenyl-3-yl)-N$^4$-(3-morpholin-4-yl-propyl)-pyrimidine-2,4-diamine | 182 |
| 3-[4-(3-Morpholin-4-ylpropylamino)-pyrimidin-2-ylamino]-N-(pyridin-3-ylmethyl)-benzenesulfonamide | 52 |
| N$^2$-[3-(1H-Indol-2-ylmethyl)-phenyl]-N$^4$-(3-morpholin-4-yl-propyl)-pyrimidine-2,4-diamine | 18 |
| {3-[4-(3-Morpholin-4-yl-propylamino)-pyrimidin-2-ylamino]-phenyl}-methanol | 465 |
| N$^2$-(3-(Benzo[d]thiazol-2-yl)-phenyl)-N$^4$-(3-morpholin-4-yl-propyl)-pyrimidine-2,4-diamine | 40 |
| 3-[4-(3-Morpholin-4-yl-propylamino)-pyrimidin-2-ylamino]-benzenesulfonamide | 14 |
| N-(3-Chlorophenyl)-3-[4-(3-pyrrolidin-1-yl-propylamino)-pyrimidin-2-ylamino]-benzamide | 12 |
| N-{3-[4-(3-Morpholin-4-yl-propylamino)-pyrimidin-2-ylamino]-phenyl}-benzamide | 25 |
| N-Isopropyl-3-[4-(3-Pyrrolidin-1-yl-propylamino)-pyrimidin-2-ylamino]-benzamide | 344 |
| N$^2$-(3-Phenoxyphenyl)-N$^4$-(3-morpholin-4-yl-propyl)-pyrimidine-2,4-diamine | 50 |
| N$^2$-(3-Chlorophenyl)-N$^4$-piperidin-4-ylmethyl-pyrimidine-2,4-diamine | 37 |
| N$^2$-(3-Chlorophenyl)-N$^4$-(1-methylpiperidin-3-ylmethyl)-pyrimidine-2,4-diamine | 4 |
| N$^2$-(3-Chlorophenyl)-N$^4$-piperidin-3-ylmethyl-pyrimidine-2,4-diamine | 25 |
| N$^2$-(3-Chlorophenyl)-N$^4$—[(3S)-1-methylpyrrolidin-3-ylmethyl]-pyrimidine-2,4-diamine | 13 |
| N$^2$-(3-Chlorophenyl)-N$^4$—[(3R)-1-methylpyrrolidin-3-ylmethyl]-pyrimidine-2,4-diamine | 7 |
| N$^2$-[3-(4-Methyl-piperazine-1-sulfonyl)phenyl]-N$^4$-(3-morpholin-4-ylpropyl)-pyrimidine-2,4-diamine | 83 |
| N-{3-[4-(3-Morpholin-4-yl-propylamino)-pyrimidin-2-ylamino]-phenyl}-nicotinamide | 112 |
| N$^2$-[3-(1H-Indol-4-yl)-phenyl]-N$^4$-(3-morpholin-4-yl-propyl)-pyrimidine-2,4-diamine | 12 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound having the formula:

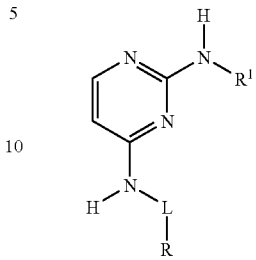

wherein R is morpholinyl;

L is a unit chosen from —CH$_2$CH$_2$—, —CH$_2$CH$_2$CH$_2$—, and —CH$_2$CH$_2$CH$_2$CH$_2$—;

R$^1$ is chosen from 3-chlorophenyl, 4-chlorophenyl, 3,4-dichlorophenyl, 3-chloro-4-methylphenyl, 3-chloro-4-fluorophenyl, 3,4-difluorophenyl, 3-trifluoromethylphenyl, 3-trifluoromethyl-4-chlorophenyl, 3-methoxyphenyl, 3-methylphenyl, 3-ethylphenyl, or 3-isopropylphenyl.

2. A compound having the formula:

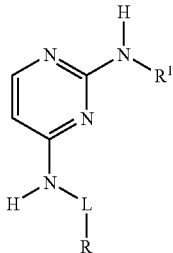

wherein R is morpholinyl;
L is a unit chosen from —CH$_2$CH$_2$—, —CH$_2$CH$_2$CH$_2$—, and —CH$_2$CH$_2$CH$_2$CH$_2$—;
R$^1$ is chosen from 2-fluorophenyl, 3-fluorophenyl, 4-fluorophenyl, 2,3-difluorophenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 2,3-dichlorophenyl, 2,4-dichlorophenyl, 2,5-dichlorophenyl, 2,6-dichlorophenyl, 2,3,4-trichlorophenyl, 2,3,5-trichlorophenyl, 2,3,6-trichlorophenyl, 2,4,5-trichlorophenyl, or 2,4,6-trichlorophenyl.

3. A compound having the formula:

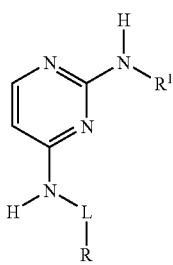

wherein R is morpholinyl;
L is a unit chosen from —CH$_2$CH$_2$—, —CH$_2$CH$_2$CH$_2$—, and —CH$_2$CH$_2$CH$_2$CH$_2$—;
R$^1$ is chosen from 2-methylphenyl, 4-methylphenyl, 2,3-dimethylphenyl, 2,4-dimethylphenyl, 2,5-dimethylphenyl, 2,6-dimethylphenyl, 3,4-dimethyl-phenyl, 2,3,4-trimethylphenyl, 2,3,5-trimethyl-phenyl, 2,3,6-trimethylphenyl, 2,4,5-trimethylphenyl, 2,4,6-trimethylphenyl, 2-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, or 2,4,6-triethylphenyl.

4. A compound having the formula:

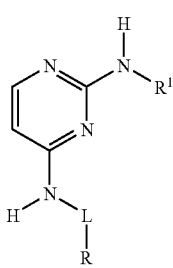

wherein R is morpholinyl;
L is a unit chosen from —CH$_2$CH$_2$—, —CH$_2$CH$_2$CH$_2$—, and —CH$_2$CH$_2$CH$_2$CH$_2$—;
R$^1$ is chosen from 2-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 2,3,4-trimethoxyphenyl, 2,3,5-trimethoxyphenyl, 2,3,6-trimethoxy-phenyl, 2,4,5-trimethoxyphenyl, 2,4,6-trimethoxyphenyl, 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,4-dihydroxyphenyl, 2,3,4-trihydroxyphenyl, 2,3,5-trihydroxy-phenyl, 2,3,6-trihydroxyphenyl, 2,4,5-trihydroxyphenyl, or 2,4,6-trihydroxyphenyl.

5. A compound having the formula:

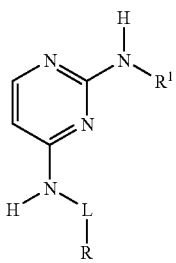

wherein R is morpholinyl;
L is a unit chosen from —CH$_2$CH$_2$—, —CH$_2$CH$_2$CH$_2$—, and —CH$_2$CH$_2$CH$_2$CH$_2$—;
R$^1$ is chosen from 3-(pyridin-2-yl)phenyl, 3-(pyridin-3-yl)phenyl, 3-(pyridin-4-yl)phenyl, 3-(pyridin-2-yl)phenyl, biphenyl-3-yl, or 3-(piperidin-1-ylmethyl)phenyl.

6. A compound having the formula:

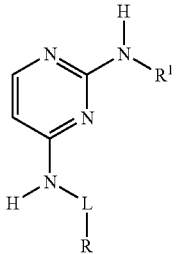

wherein R is morpholinyl;
L is a unit chosen from —CH$_2$CH$_2$—, —CH$_2$CH$_2$CH$_2$—, and —CH$_2$CH$_2$CH$_2$CH$_2$—;
R$^1$ is chosen from benzene-sulfonamide, N-methyl-benzenesulfonamide, N-ethyl-benzenesulfonamide, N-(n-propyl)-benzenesulfonamide, N-(iso-propyl)-benzenesulfonamide, N-(n-butyl)-benzenesulfonamide, N-(sec-butyl)-benzenesulfonamide, N-(iso-butyl)-benzenesulfonamide, and N-(tert-butyl)-benzenesulfonamide.

7. A compound having the formula:

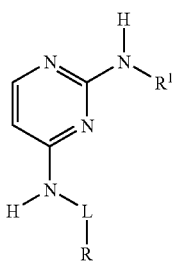

wherein R is morpholinyl;

L is a unit chosen from —CH$_2$CH$_2$—, —CH$_2$CH$_2$CH$_2$—, and —CH$_2$CH$_2$CH$_2$CH$_2$—;

R$^1$ is chosen from N-phenyl-benzene-sulfonamide, N-(pyrimidin-2-yl)-benzenesulfonamide, N-(pyrimidin-4-yl)-benzenesulfonamide, N-(pyrimidin-5-yl)-benzenesulfonamide, N-(pyridin-2-yl)-benzenesulfonamide, N-(pyridin-3-yl)-benzenesulfonamide, and N-(pyridin-4-yl)-benzenesulfonamide.

8. A compound having the formula:

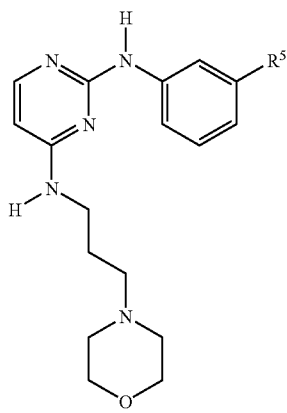

wherein R$^5$ has the formula:

-(L$^1$)$_y$-R$^6$

R$^6$ is a unit chosen from:
i) hydrogen;
ii) halogen;
iii) nitro;
iv) hydroxy;
v) amino or mono- or di-substituted (C$_1$-C$_4$ linear or branched alkyl)amino;
vi) substituted or unsubstituted C$_1$-C$_4$ linear or branched alkyl;
vii) substituted or unsubstituted C$_1$-C$_4$ linear or branched alkoxy;
viii) substituted or unsubstituted phenyl;
ix) substituted or unsubstituted C$_2$-C$_5$ heterocyclic; and
x) substituted or unsubstituted C$_3$-C$_9$ heteroaryl;
xi) cyano; or
xii) CH$_m$X$_{3-m}$ wherein X is halogen and m is from 0 to 2;

L$^1$ is a linking unit chosen from:
i) —[CH$_2$]$_j$—;
ii) —O[CH$_2$]$_k$—;
iii) —SO$_2$NH—;
iv) —NHC(O)—; or
v) —C(O)NH—;

the index j is 0, 1 or 2, the index k is 0 or 1.

9. A compound having the formula:

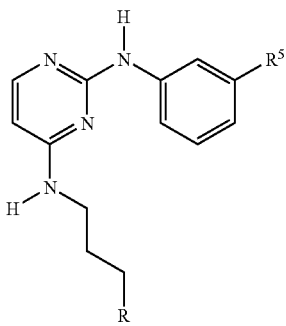

wherein R is a unit having the formula:

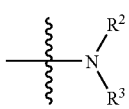

R$^2$ and R$^3$ are taken together to form a morpholinyl ring;
R$^5$ has the formula:

-(L$^1$)$_y$-R$^6$

R$^6$ is a unit chosen from:
i) hydrogen;
ii) halogen;
iii) nitro;
iv) hydroxy;
v) amino or mono- or di-substituted (C$_1$-C$_4$ linear or branched alkyl)amino;
vi) substituted or unsubstituted C$_1$-C$_4$ linear or branched alkyl;
vii) substituted or unsubstituted C$_1$-C$_4$ linear or branched alkoxy;
viii) substituted or unsubstituted phenyl;
ix) substituted or unsubstituted C$_2$-C$_5$ heterocyclic;
x) substituted or unsubstituted C$_3$-C$_9$ heteroaryl;
xi) cyano; or
xii) CH$_m$X$_{3-m}$ wherein X is halogen and m is from 0 to 2;

L$^1$ is a linking unit chosen from:
i) —[CH$_2$]$_j$—;
ii) —O[CH$_2$]$_k$—;
iii) —SO$_2$NH—;
iv) —NHC(O)—; or
v) —C(O)NH—;

the index j is 0, 1 or 2, the index k is 0 or 1.

10. A compound having the formula:

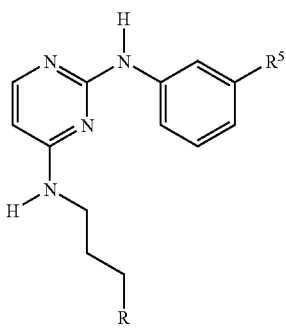

wherein R is a unit having the formula:

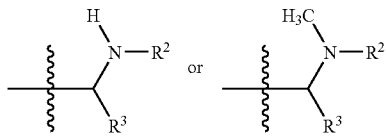

$R^2$ and $R^3$ are taken together to form a morpholinyl ring;
$R^5$ has the formula:

-$(L^1)_y$-$R^6$ $R^6$ is a unit chosen from:
i) hydrogen;
ii) halogen;
iii) nitro;
iv) hydroxy;
v) amino or mono- or di-substituted ($C_1$-$C_4$ linear or branched alkyl)amino;
vi) substituted or unsubstituted $C_1$-$C_4$ linear or branched alkyl;
vii) substituted or unsubstituted $C_1$-$C_4$ linear or branched alkoxy;
viii) substituted or unsubstituted phenyl;
ix) substituted or unsubstituted $C_2$-$C_5$ heterocyclic; and
x) substituted or unsubstituted $C_3$-$C_9$ heteroaryl;
xi) cyano; or
xii) $CH_mX_{3-m}$ wherein X is halogen and m is from 0 to 2;
$L^1$ is a linking unit chosen from:
i) —[$CH_2$]$_j$—;
ii) —O[$CH_2$]$_k$—;
iii) —$SO_2$NH—;
iv) —NHC(O)—; or
v) —C(O)NH—;
the index j is 0, 1 or 2, the index k is 0 or 1.

11. A compound having the formula:

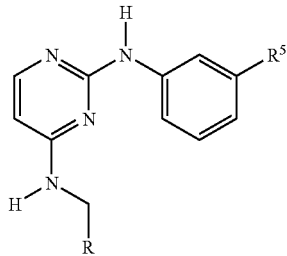

wherein R is a heterocyclic unit chosen from:

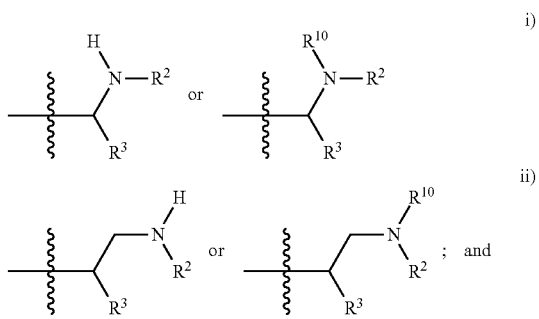

iii) $R^2$ and $R^3$ are taken together to form a morpholinyl ring;
$R^5$ has the formula:

-$(L^1)_y$-$R^6$ $R^6$ is a unit chosen from:
i) hydrogen;
ii) halogen;
iii) nitro;
iv) hydroxy;
v) amino or mono- or di-substituted ($C_1$-$C_4$ linear or branched alkyl)amino;
vi) substituted or unsubstituted $C_1$-$C_4$ linear or branched alkyl;
vii) substituted or unsubstituted $C_1$-$C_4$ linear or branched alkoxy;
viii) substituted or unsubstituted phenyl;
ix) substituted or unsubstituted $C_2$-$C_5$ heterocyclic;
x) substituted or unsubstituted $C_3$-$C_9$ heteroaryl;
xi) cyano; or
xii) $CH_mX_{3-m}$ wherein X is halogen and m is from 0 to 2;
$L^1$ is a linking unit chosen from:
i) —[$CH_2$]$_j$—;
ii) —O[$CH_2$]$_k$—;
iii) —$SO_2$NH—;
iv) —NHC(O)—; or
v) —C(O)NH—;
the index j is 0, 1 or 2, the index k is 0 or 1;
$R^{10}$ is methyl, ethyl, 1-propyl, 2-propyl, or phenyl.

\* \* \* \* \*